(12) United States Patent
Winslow

(10) Patent No.: US 7,101,846 B2
(45) Date of Patent: Sep. 5, 2006

(54) METHODS AND COMPOSITIONS FOR OPTIMIZATION OF OXYGEN TRANSPORT BY CELL-FREE SYSTEMS

(75) Inventor: Robert M. Winslow, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/917,223

(22) Filed: Aug. 11, 2004

(65) Prior Publication Data

US 2005/0009736 A1    Jan. 13, 2005

Related U.S. Application Data

(63) Continuation of application No. 10/199,269, filed on Jul. 18, 2002, now abandoned, which is a continuation of application No. 09/544,656, filed on Apr. 5, 2000, now Pat. No. 6,432,918, which is a continuation of application No. 09/032,342, filed on Feb. 27, 1998, now Pat. No. 6,054,427, which is a continuation-in-part of application No. 08/810,694, filed on Feb. 28, 1997, now Pat. No. 5,814,601.

(51) Int. Cl.
*A61K 38/16* (2006.01)
*A61K 35/14* (2006.01)

(52) U.S. Cl. ................ 514/6; 514/21; 514/832; 514/833; 530/385; 530/402; 530/813; 530/815; 530/829; 424/529

(58) Field of Classification Search ............ 514/6, 514/21, 832, 833; 530/385, 402, 813, 815; 530/829; 424/529
See application file for complete search history.

(56) References Cited

U.S. PATENT DOCUMENTS

| | | | |
|---|---|---|---|
| 3,925,344 A | 12/1975 | Mazur | |
| 3,956,259 A | 5/1976 | Garcia et al. | |
| 4,001,200 A | 1/1977 | Bonsen et al. | |
| 4,001,401 A | 1/1977 | Bonsen et al. | |
| 4,053,590 A | 10/1977 | Bonsen et al. | |
| 4,061,736 A | 12/1977 | Morris et al. | |
| 4,064,118 A | 12/1977 | Wong | |
| 4,113,853 A | 9/1978 | Funakoshi et al. | |
| 4,133,874 A | 1/1979 | Miller et al. | |
| 4,179,337 A | 12/1979 | Davis et al. | |
| 4,301,144 A | 11/1981 | Iwashita et al. | |
| 4,316,093 A | 2/1982 | Broers et al. | |
| 4,336,248 A | 6/1982 | Bonhard et al. | |
| 4,377,512 A | 3/1983 | Ajisaka et al. | |
| 4,401,652 A | 8/1983 | Simmonds et al. | |
| 4,412,989 A | 11/1983 | Iwashita et al. | |
| 4,439,357 A | 3/1984 | Bonhard et al. | |
| 4,473,494 A | 9/1984 | Tye | |
| 4,473,496 A | 9/1984 | Scannon | |
| 4,526,715 A | 7/1985 | Kothe et al. | |
| 4,529,719 A | 7/1985 | Tye | |
| 4,532,130 A | 7/1985 | Djordjevich et al. | |
| 4,584,130 A | 4/1986 | Bucci et al. | |
| 4,598,064 A | 7/1986 | Walder | |
| 4,600,531 A | 7/1986 | Walder | |
| 4,650,786 A | 3/1987 | Wong | |
| 4,670,417 A | 6/1987 | Iwasaki et al. | |
| 4,710,488 A | 12/1987 | Wong | |
| 4,730,936 A | 3/1988 | Thorjusen, Jr. | |
| 4,738,952 A | 4/1988 | Ecanow et al. | |
| 4,777,244 A | 10/1988 | Bonhard et al. | |
| 4,826,811 A | 5/1989 | Sehgal et al. | |
| 4,831,012 A | 5/1989 | Estep | |
| 4,857,636 A | 8/1989 | Hsia | |
| 4,861,867 A | 8/1989 | Estep | |
| 4,900,780 A | 2/1990 | Cerny | |
| 4,911,929 A | 3/1990 | Farmer et al. | |
| 4,920,194 A | 4/1990 | Feller et al. | |
| 4,987,154 A | 1/1991 | Long, Jr. | |
| 5,028,588 A | 7/1991 | Hoffman et al. | |
| 5,041,615 A | 8/1991 | Hai et al. | |
| 5,061,688 A | 10/1991 | Beissinger et al. | |
| 5,077,036 A | 12/1991 | Long, Jr. | |
| 5,080,885 A | 1/1992 | Long, Jr. | |
| 5,084,558 A | 1/1992 | Rausch et al. | |
| 5,114,932 A | 5/1992 | Runge | |
| 5,115,100 A | 5/1992 | Wu et al. | |
| 5,128,452 A | 7/1992 | Hai et al. | |
| 5,194,590 A | 3/1993 | Sehgal et al. | |
| 5,200,323 A | 4/1993 | Chang et al. | |
| 5,217,648 A | 6/1993 | Beissinger et al. | |
| 5,234,903 A | 8/1993 | Nho et al. | |
| 5,239,061 A | 8/1993 | Fronticelli et al. | |

(Continued)

FOREIGN PATENT DOCUMENTS

EP    0361 719 A1    4/1990

(Continued)

OTHER PUBLICATIONS

Guyton, *Human Physiology And Mechanisms Of Disease* (3rd. ed.; W.B. Saunders Co., Philadelphia, PA), pp. 228-229 (1982).

(Continued)

*Primary Examiner*—Jon Weber
*Assistant Examiner*—Abdel A. Mohamed
(74) *Attorney, Agent, or Firm*—Medlen & Carroll LLP

(57) ABSTRACT

Compositions, and methods of use thereof, for use as blood substitute products comprise aqueous mixtures of oxygen-carrying and non-oxygen carrying plasma expanders and methods for the use thereof. The oxygen-carrying component may consist of any hemoglobin-based oxygen carrier, while the non-oxygen carrying plasma expander my consist of any suitable diluent.

13 Claims, 23 Drawing Sheets

U.S. PATENT DOCUMENTS

| | | |
|---|---|---|
| 5,248,766 A | 9/1993 | Nelson et al. |
| 5,250,665 A | 10/1993 | Kluger et al. |
| 5,252,714 A | 10/1993 | Harris et al. |
| 5,264,555 A | 11/1993 | Shorr et al. |
| 5,281,579 A | 1/1994 | Estep |
| 5,295,944 A | 3/1994 | Teicher et al. |
| 5,296,465 A | 3/1994 | Rausch et al. |
| 5,312,808 A | 5/1994 | Shorr et al. |
| 5,334,705 A | 8/1994 | Bonaventura et al. |
| 5,334,706 A | 8/1994 | Przybelski |
| 5,344,393 A | 9/1994 | Roth et al. |
| 5,349,054 A | 9/1994 | Bonaventura et al. |
| 5,352,773 A | 10/1994 | Kandler et al. |
| 5,386,014 A | 1/1995 | Nho et al. |
| 5,407,428 A | 4/1995 | Segall et al. |
| 5,438,041 A | 8/1995 | Zheng et al. |
| 5,439,591 A | 8/1995 | Pliura et al. |
| 5,449,759 A | 9/1995 | Hoffman et al. |
| 5,451,205 A | 9/1995 | Roth et al. |
| 5,464,814 A | 11/1995 | Sehgal et al. |
| 5,478,805 A | 12/1995 | Shorr et al. |
| 5,478,806 A | 12/1995 | Nho |
| 5,480,866 A | 1/1996 | Bonaventura et al. |
| 5,510,464 A | 4/1996 | Przybelski |
| 5,525,630 A | 6/1996 | Hoffman |
| 5,532,352 A | 7/1996 | Pliura et al. |
| 5,545,328 A | 8/1996 | Pliura et al. |
| 5,545,727 A | 8/1996 | Hoffman et al. |
| 5,554,638 A | 9/1996 | Dewhirst et al. |
| 5,563,254 A | 10/1996 | Hoffman et al. |
| 5,571,801 A | 11/1996 | Segall et al. |
| 5,574,019 A | 11/1996 | Segall et al. |
| 5,578,564 A | 11/1996 | Chivers et al. |
| 5,585,484 A * | 12/1996 | Acharya et al. ............ 540/145 |
| 5,591,710 A | 1/1997 | Hsia |
| 5,595,723 A | 1/1997 | Quay |
| 5,599,907 A | 2/1997 | Anderson et al. |
| 5,613,944 A | 3/1997 | Segall et al. |
| 5,614,490 A | 3/1997 | Przybelski |
| 5,618,919 A | 4/1997 | Rausch et al. |
| 5,628,930 A | 5/1997 | Weers et al. |
| 5,631,219 A | 5/1997 | Rosenthal et al. |
| 5,635,538 A | 6/1997 | Weers et al. |
| 5,635,539 A | 6/1997 | Clark, Jr. et al. |
| 5,650,388 A | 7/1997 | Shorr et al. |
| 5,661,124 A * | 8/1997 | Hoffman et al. ............... 514/6 |
| 5,814,601 A | 9/1998 | Winslow et al. |
| 5,985,825 A | 11/1999 | Winslow et al. |
| 6,054,427 A | 4/2000 | Winslow |
| 6,432,918 B1 | 8/2002 | Winslow |

FOREIGN PATENT DOCUMENTS

| | | |
|---|---|---|
| WO | WO87/07832 | 12/1987 |
| WO | WO90/13309 | 11/1990 |
| WO | WO91/07190 | 5/1991 |

OTHER PUBLICATIONS

Hannon et al., "Blood and Acid-base Status of Conscious Pigs subjected to Fixed-volume Hemorrhage and Resuscitated with Hypertonic Saline Dextran," *Circulatory Shock* 32:19-29 (1990).

Intaglietta, "Whitaker Lecture 1996: Microcirculation, Biomedical Engineering, and Artificial Blood," *Ann. Biomed. Engineer.* 25:593-603 (1997).

Iwasaki and Iwashita, "Preparation and Evaluation of Hemoglobin-Polyethylene Glycol Conjugate (Pyridoxalated Polyethylene Glycol Hemoglobin) as an Oxygen-Carrying Resuscitation Fluid," *Artif. Organs* 10:411-416 (1986).

Kerger et al., "Systemic and subcutaneous microvascular oxygen tension in conscious Syrian golden hamsters," *Am. J. Physiol.* 267 (*Heart. Circ. Physiol.* 37):H802-810 (1995).

Mirhashemi et al., "Model analysis of the enhancement of tissue oxygenation by hemodilution due to increased microvascular flow velocity," *Microvasc. Res.* 34:290-301 (1987).

Mirhashemi et al., "Effects of hemodilution on skin microcirculation," *Am. J. Physiol.* 254:H411-H416 (1988).

Papenfuss et al., "A transparent access chamber for the rat dorsal skin fold," *Microvasc. Res.* 18:311-318 (1979).

Prouchayret et al., "A Potential Blood Substitute from Carboxylic Dextran and Oxyhemoglobin. I. Preparation, Purification and Characterization," *Biomat. ARt. Cells & Immolb. Biotech.* 20: 319-322 (1992).

Reinhart et al., "Rheologic Measurements on Small Samples with a New Capillary Viscometer," *J. Lab. Clin. Med.* 104:921-31 (1984).

Simoni et al., "An Improved Blood Substitute," *In Vivo* Evaluation of its Hemodynamic Effects, *ASAIO J.*, 42:M773-782 (1996).

Sherwood (ed.), *Fundamentals of Physiology*, 2nd edition, West Publishing Company: St. Paul, MN, pp. 256-258 & 339-344 (1995).

Stetter et al., "Influence of a Recombinant Hemoglobin Solution on Blood Rheology," *Transfusion* 37:1149-1155 (1997).

Tai and Intaglietta, "Local tissue oxygenation by statistically distributed sources," *Microvasc. Res.* 44:200-213 (1992).

Tsai et al., "Microcirculatory consequences of blood substitution with α α -hemoglobin," in Winslow et al., (eds)., *Blood Substitutes. Physiological Basis of Efficacy*, Birkhäuser, Boston, MA, pp. 155-174 (1995).

Vandegriff and Shrager, "Hemoglobin-Oxygen Equilibrium Binding: Rapid-Scanning Spectrophotometry and Singular Value Decomposition," *Meth. Enzymol.* 232:460-485 (1994).

Winslow et al., "Oxygen Equilibrium Curve of Normal Human Blood and Its Evaluation by Adair's Equation," *J. Biol. Chem.* 252(7):2331-2337 (1977).

* cited by examiner

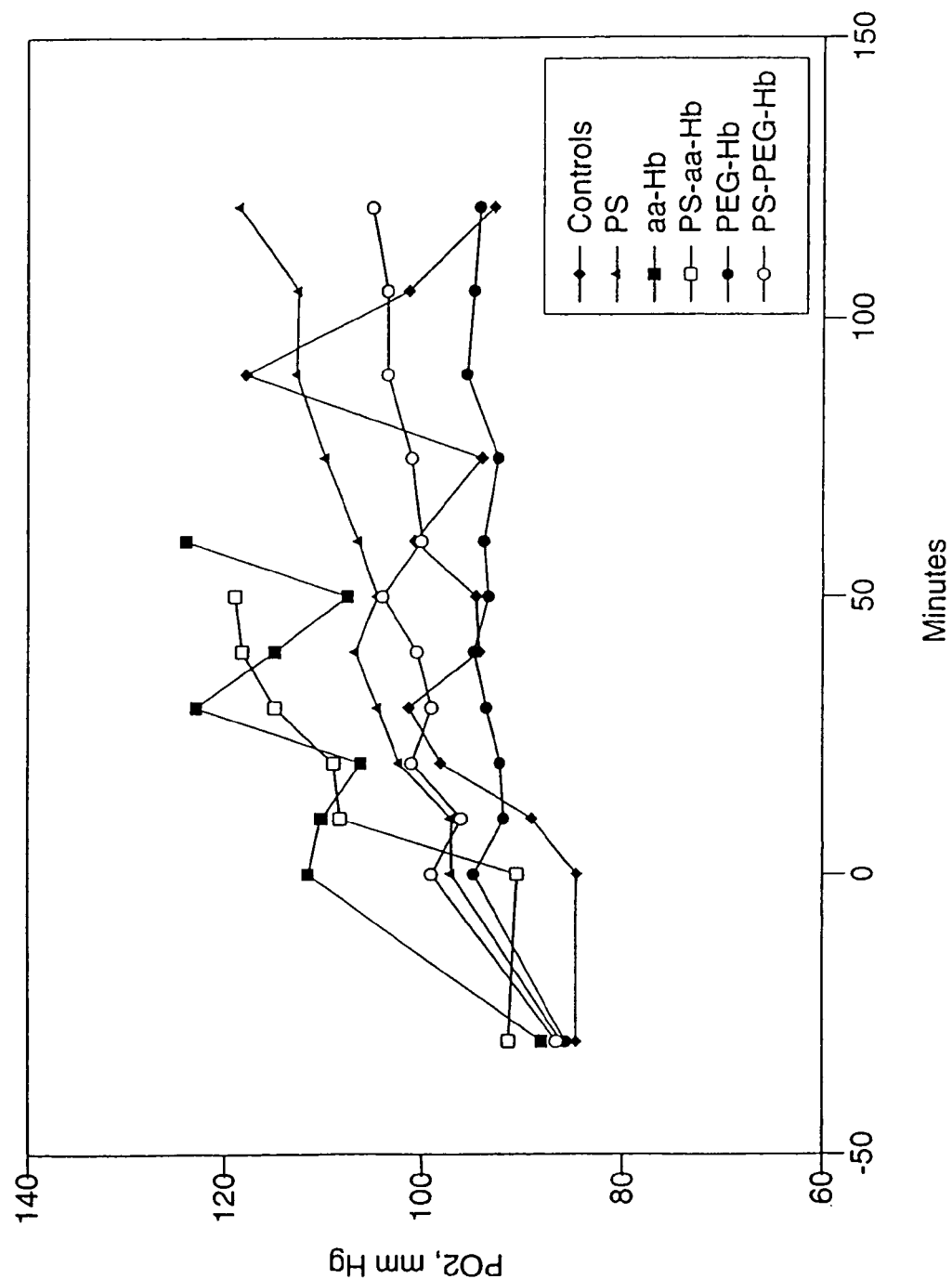

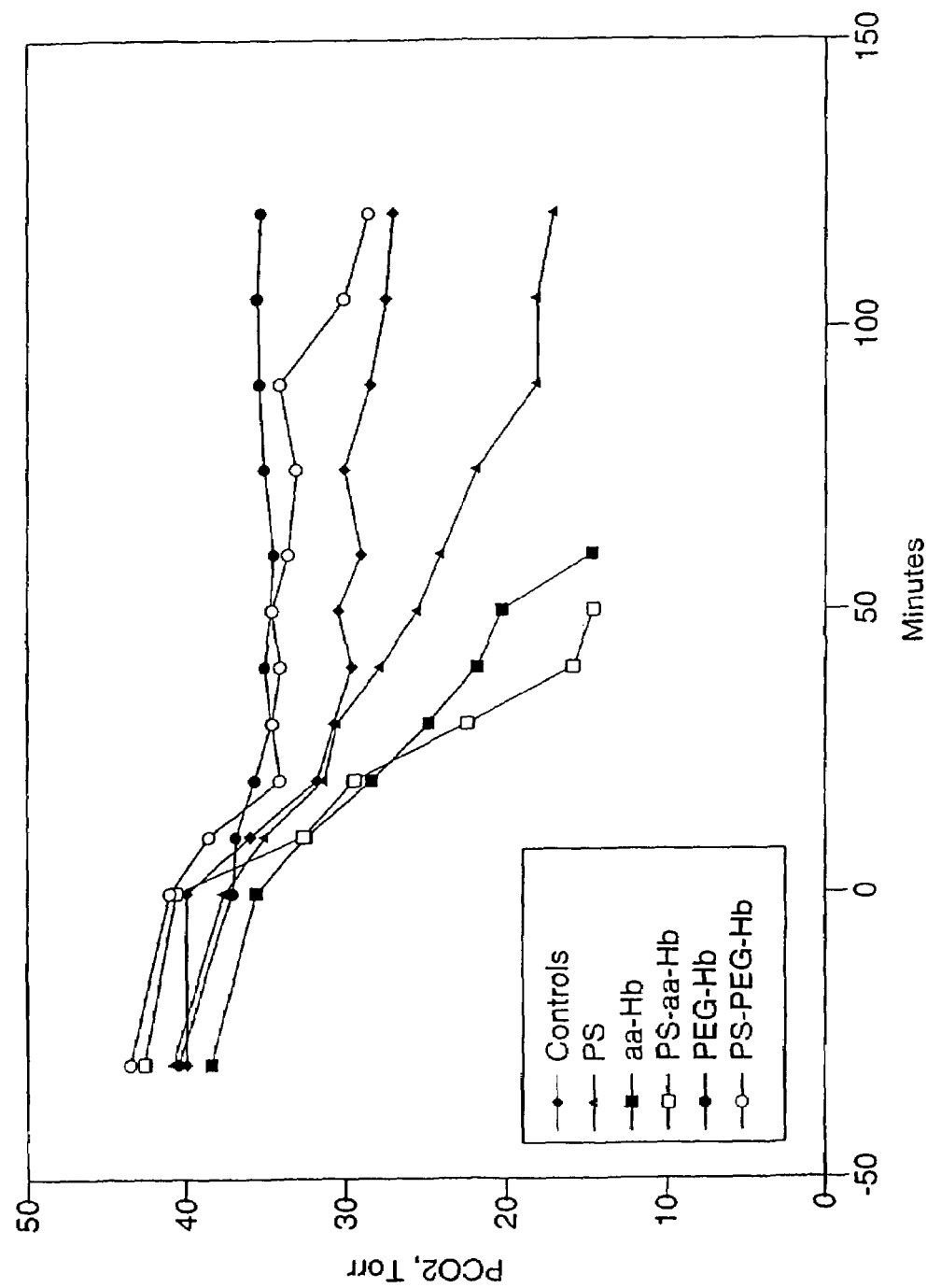

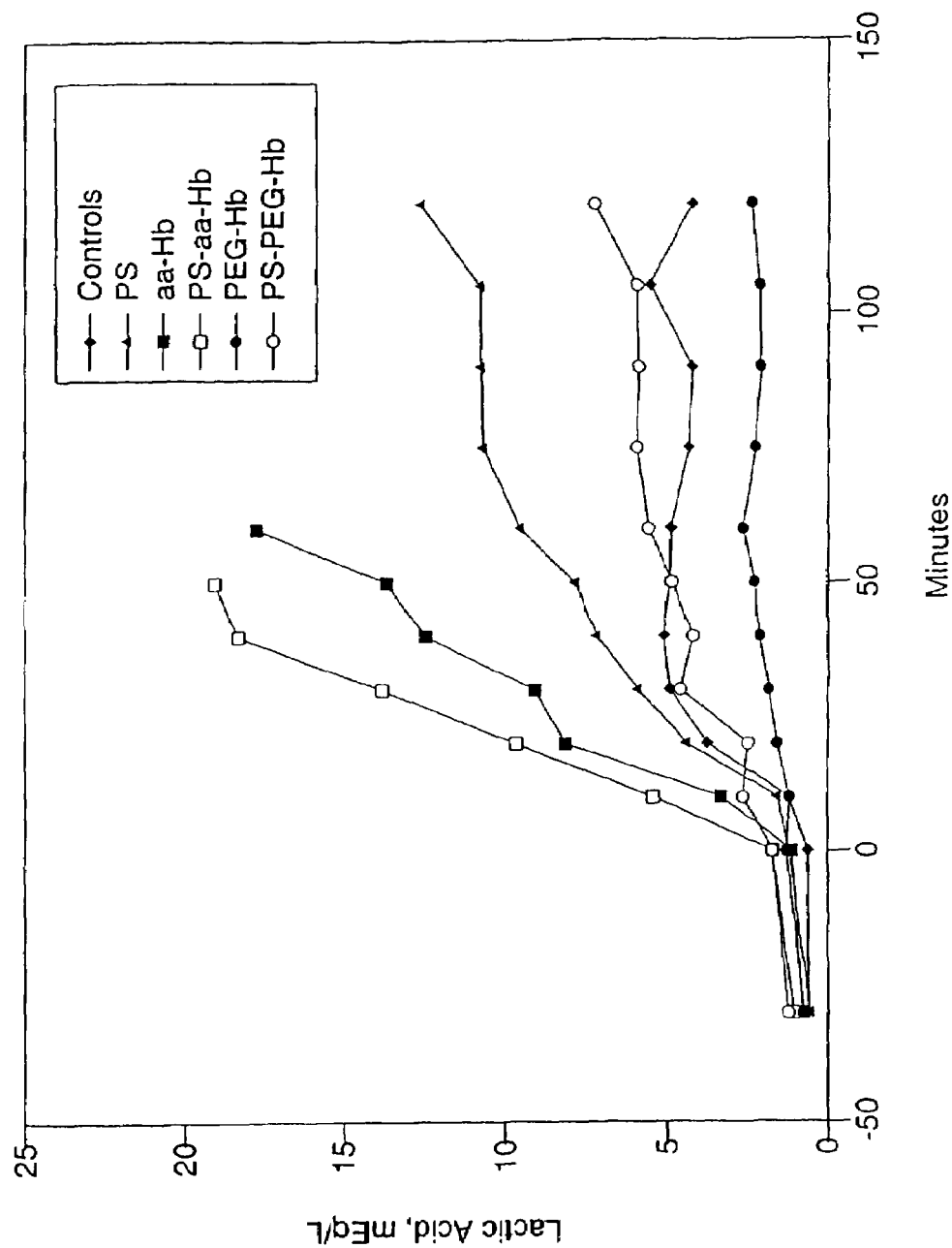

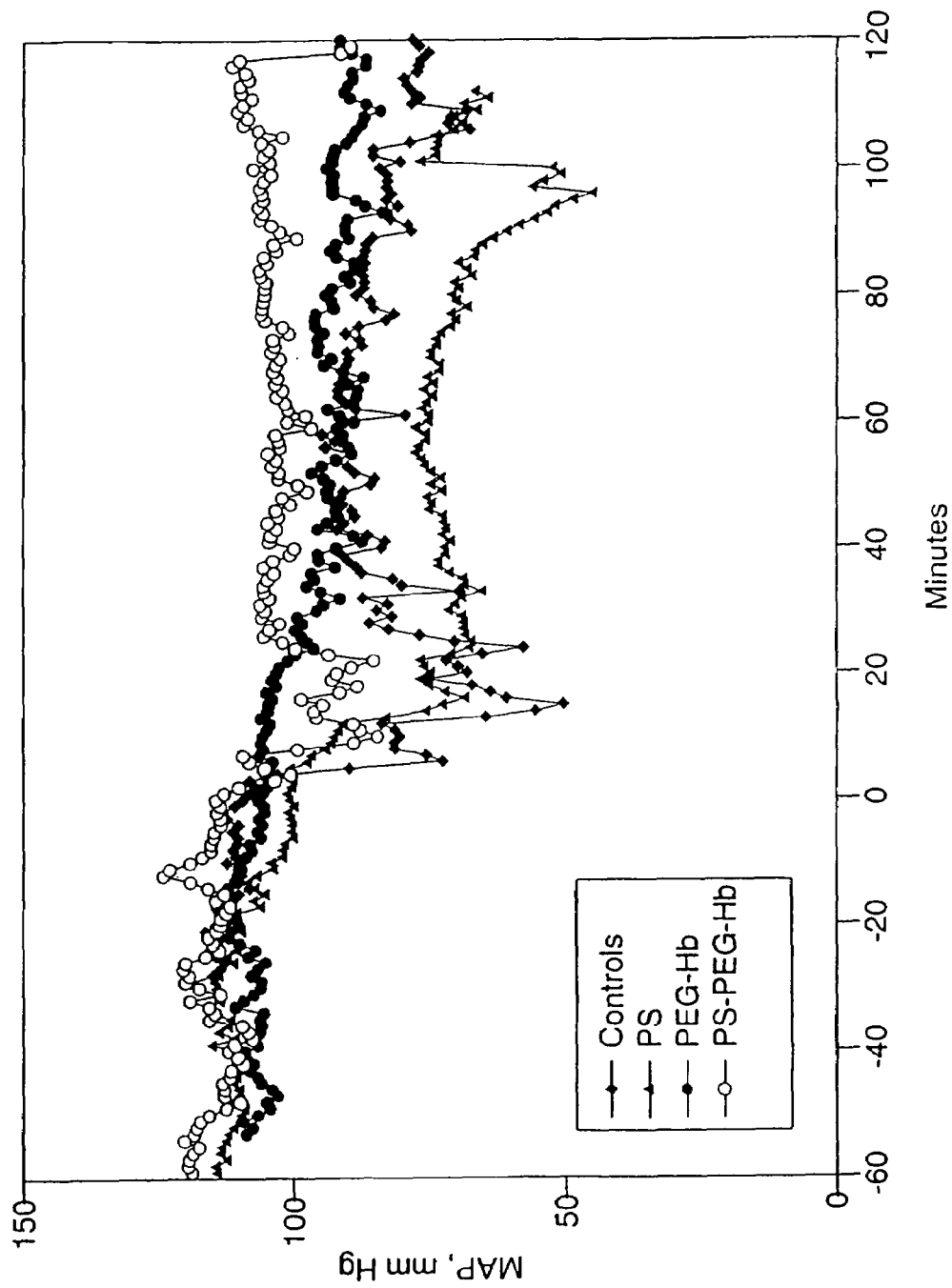

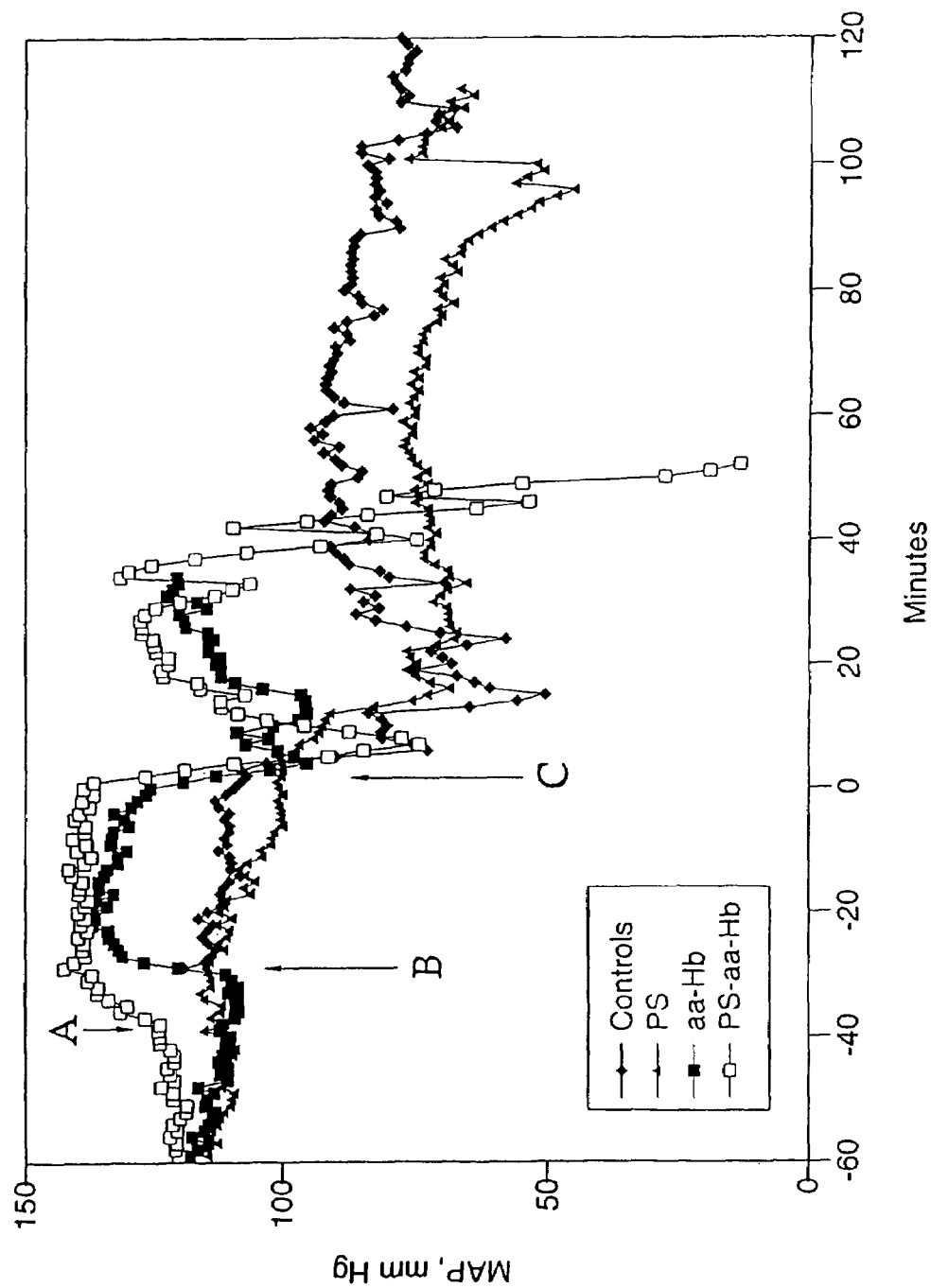

METHODS AND COMPOSITIONS FOR OPTIMIZATION OF OXYGEN TRANSPORT BY CELL-FREE SYSTEMS

The present application is a continuation of application Ser. No. 10/199,269, filed Jul. 18, 2002, now abadoned, which is a continuation of application Ser. No. 09/544,656, filed Apr. 5, 2000, and issued as U.S. Pat. No.6,432,918 on Aug. 13, 2002, which is a continuation of application Ser. No. 09/032,342, filed Feb. 27, 1998, and issued as U.S. Pat. No. 6,054,427 on Apr. 25, 2000, which is a continuation-in-part of application Ser. No. 08/810,694, filed Feb. 28, 1997, and issued as U.S. Pat. No. 5,814,601 on Sep. 29, 1998.

This invention was made with Government support under the National Institutes of Health (NIH) awarded by contract P01 HL48018. The Government has certain rights in this invention.

FIELD OF THE INVENTION

The present invention relates generally to blood products, and more particularly to compositions comprising mixtures of oxygen-carrying and non-oxygen carrying plasma expanders and methods for their use.

BACKGROUND OF THE INVENTION

A. The Circulatory System and the Nature of Hemoglobin

The blood is the means for delivering nutrients to the tissues and removing waste products from the tissues for excretion. The blood is composed of plasma in which red blood cells (RBCs or erythrocytes), white blood cells (WBCs), and platelets are suspended. Red blood cells comprise approximately 99% of the cells in blood, and their principal function is the transport of oxygen to the tissues and the removal of carbon dioxide therefrom.

The left ventricle of the heart pumps the blood through the arteries and the smaller arterioles of the circulatory system. The blood then enters the capillaries, where the majority of the exchange of nutrients and cellular waste products occurs. (See, e.g., A. C. Guyton, *Human Physiology and Mechanisms Of Disease* (3rd. ed.; W. B. Saunders Co., Philadelphia, Pa.), pp. 228–229 [1982]). Thereafter, the blood travels through the venules and veins in its return to the right atrium of the heart. Though the blood that returns to the heart is oxygen-poor compared to that which is pumped from the heart, in resting man the returning blood still contains about 75% of the original oxygen content.

The reversible oxygenation function (i.e., the delivery of oxygen and the removal of carbon dioxide) of RBCs is carried out by the protein hemoglobin. In mammals, hemoglobin has a molecular weight of approximately 68,000 and is composed of about 6% heme and 94% globin. In its native form, it contains two pairs of subunits (i.e., it is a tetramer), each containing a heme group and a globin polypeptide chain. In aqueous solution, hemoglobin is present in equilibrium between the tetrameric (MW 68,000) and dimeric forms (MW 34,000); outside of the RBC, the dimers are prematurely excreted by the kidney (plasma half-life of approximately two to four hours). Along with hemoglobin, RBCs contain stroma (the RBC membrane), which comprises proteins, cholesterol, and phospholipids.

B. Exogenous Blood Products

Due to the demand for blood products in hospitals and other settings, extensive research has been directed at the development of blood substitutes and plasma expanders. A blood substitute is a blood product that is capable of carrying and supplying oxygen to the tissues. Blood substitutes have a number of uses, including replacing blood lost during surgical procedures and following acute hemorrhage, and for resuscitation procedures following traumatic injury. Plasma expanders are blood products that are administered into the vascular system but are typically not capable of carrying oxygen. Plasma expanders can be used, for example, for replacing plasma lost from burns, to treat volume deficiency shock, and to effect hemodilution (for, e.g., the maintenance of normovolemia and to lower blood viscosity). Essentially, blood products can be used for these purposes or any purpose in which banked blood is currently administered to patients. (See, e.g., U.S. Pat. No. 4,001,401 to Bonson et al. and U.S. Pat. No. 4,061,736 to Morris et al., hereby incorporated by reference).

The current human blood supply is associated with several limitations that can be alleviated through the use of an exogenous blood product. To illustrate, the widespread availability of safe and effective blood substitutes would reduce the need for banked (allogeneic) blood. Moreover, such blood substitutes would allow the immediate infusion of a resuscitation solution following traumatic injury without regard to cross-matching (as is required for blood), thereby saving valuable time in resupplying oxygen to ischemic tissue. Likewise, blood substitutes can be administered to patients prior to surgery, allowing removal of autologous blood from the patients which could be returned later in the procedure, if needed, or after surgery. Thus, the use of exogenous blood products not only protects patients from exposure to non-autologous (allogeneic) blood, it conserves either autologous or allogeneic (banked, cross-matched) blood for its optimal use.

C. Limitations of Current Blood Substitutes

Attempts to produce blood substitutes (sometimes referred to as "oxygen-carrying plasma expanders") have thus far produced products with marginal efficacy or whose manufacture is tedious and expensive, or both. Frequently, the cost of manufacturing such products is so high that it effectively precludes the widespread use of the products, particularly in those markets where the greatest need exists (e.g., emerging third-world economies).

The blood substitutes that have been developed previously are reviewed in various references (See e.g., Winslow, Robert M., "Hemoglobin-based Red Cell Substitutes," Johns Hopkins University Press, Baltimore [1992]). They can be grouped into the following three categories: i) perfluorocarbon-based emulsions, ii) liposome—encapsulated hemoglobin, and iii) modified cell-free hemoglobin. As discussed below, none has been entirely successful, though products comprising modified cell-free hemoglobin are thought to be the most promising. Perfluorochemical-based compositions dissolve oxygen as opposed to binding it as a chelate. In order to be used in biological systems, the perfluorochemical must be emulsified with a lipid, typically egg-yolk phospholipid. Though the perfluorocarbon emulsions are inexpensive to manufacture, they do not carry sufficient oxygen at clinically tolerated doses to be effective. Conversely, while liposome-encapsulated hemoglobin has been shown to be effective, it is far too costly for widespread use (See e.g., Winslow, supra).

Most of the blood substitute products in clinical trials today are based on modified hemoglobin. These products, frequently referred to as hemoglobin-based oxygen carriers (HBOCs), generally comprise a homogeneous aqueous solution of a chemically-modified hemoglobin, essentially free from other red cell residues (stroma). Although stroma-free human hemoglobin is the most common raw material for preparing a HBOC, other sources of hemoglobin have also been used. For example, hemoglobin can be obtained or derived from animal blood (e.g., bovine hemoglobin) or from bacteria or yeast or transgenic animals molecularly altered to produce a desired hemoglobin product. (See generally, Winslow, supra).

The chemical modification is generally one of intramolecular crosslinking and/or oligomerization to modify the hemoglobin such that its persistence in the circulation is prolonged relative to that of unmodified hemoglobin, and its oxygen binding properties are similar to those of blood. Intramolecular crosslinking chemically binds together subunits of the tetrameric hemoglobin unit to prevent the formation of dimers which, as previously indicated, are prematurely excreted. (See, e.g., U.S. Pat. No. 5,296,465 to Rausch et al., hereby incorporated by reference).

The high costs of manufacturing HBOC products have greatly limited their commercial viability. In addition, the present inventors have found that known HBOCs have a tendency to release excessive amounts of oxygen to the tissues at the arteriole walls rather than the capillaries; this can result in insufficient oxygen available for delivery by the HBOC to the tissues surrounding the capillaries. This is despite the fact that the initial loading of the HBOC with oxygen may be relatively high, even higher than that normally achieved with natural red blood cells.

What is needed is a blood product that is relatively inexpensive to manufacture and that delivers adequate amounts of oxygen to the tissues.

SUMMARY OF THE INVENTION

The present invention is directed at compositions comprising mixtures of an oxygen-carrying component and a non-oxygen carrying component and methods for their use. The compositions overcome the limited oxygen delivery characteristics of previous blood substitutes, and therefore lower doses may be used. They are a safer and more effective alternative to currently available blood substitutes.

The present invention contemplates a means of improving the oxygen delivering capacity of an oxygen carrier by combining that carrier with a non-oxygen-carrying component like a conventional plasma expander. In preferred embodiments, the oxygen carrier (i.e., the oxygen-carrying component) is a hemoglobin-based oxygen carrier. The hemoglobin may be either native (unmodified); subsequently modified by a chemical reaction such as crosslinking, polymerization, or the addition of chemical groups (i.e., polyethyleneglycol, polyoxyethylene, or other adducts); or it may be recombinant or encapsulated in a liposome. A non-oxygen-carrying plasma expander is any substance used for temporary replacement of red cells which has oncotic pressure (e.g., starches such as hetastarch or pentastarch, dextran such as dextran-70 or dextran-90, albumin, or any other colloidal intravenous solution).

More specifically, it is contemplated that the compositions of the present invention will contain one or more of the following properties: i) viscosity at least half that of blood, ii) oncotic pressure higher than that of plasma; iii) hemoglobin oxygen affinity higher than or equal to (i.e., P50 equal to or lower than) that of blood; and iv) oxygen capacity less than that of blood. It is not intended that the invention be limited to how the compositions are used. A variety of uses are contemplated for the compositions of the present invention, including, but not limited to, the treatment of hemorrhage or use in hemodilution.

Particular non-oxygen carrying plasma expanders have been used (e.g., for hemodilution) for a number of years, and their physiological effects following administration are well characterized. Previously, researchers have assumed that administration of an oxygen-carrying blood product (e.g., a blood substitute like an HBOC), should result in physiological cardiovascular responses similar to those observed following administration of non-oxygen carrying diluent materials of similar molecular weight (e.g., dextran 70,000 MW, albumins and starches). Furthermore, researchers in the field of blood substitutes have been working under several other key assumptions. More specifically, prior to the present invention, it has been thought that blood substitutes should have viscosity less than that of blood, oxygen affinity similar to or equal to or lower than that of red cells, minimal colloidal osmotic (oncotic) pressure, and hemoglobin concentration as high as possible. As described in detail below, the compositions and methods of the present invention are counter-intuitive to some of these assumptions.

The present invention contemplates a blood product solution, comprising an oxygen-carrying component and a non-oxygen carrying component, the blood product solution having oncotic pressure higher than that of plasma and viscosity at least half that of blood. In some embodiments, the blood product solution further comprises oxygen affinity equal to or greater than that of blood. In other embodiments, the blood product solution further comprises oxygen capacity less than that of blood. In particular embodiments, the oxygen-carrying component is a polyethylene glycol-modified hemoglobin. Furthermore, in certain embodiments the non-oxygen-carrying component is a colloid starch. When the non-oxygen-carrying component is a colloid starch, it has an average molecular weight of from approximately 200,000 daltons to approximately 400,000 daltons is some embodiments. In particular embodiments, the colloid starch is pentastarch.

The present invention also contemplates a blood product solution, comprising a) an oxygen-carrying component, the oxygen-carrying component comprising a polyethylene glycol-modified hemoglobin; and b) a non-oxygen carrying component, the non-oxygen-carrying component comprising a colloid starch having an average molecular weight of from approximately 200,000 daltons to approximately 400,000 daltons. In some embodiments, the polyethylene glycol-modified hemoglobin comprises hemoglobin selected from the group consisting of animal hemoglobin, human hemoglobin, and recombinant hemoglobin. In particular embodiments, the colloid starch has an average molecular weight of from approximately 225,000 daltons to approximately 300,000 daltons, and in other embodiments the colloid starch is pentastarch. In still other embodiments, the pentastarch comprises from approximately 20 percent to approximately 80 percent by volume of the blood product solution, whereas the pentastarch comprises from approximately 40 percent to approximately 60 percent by volume of the blood product in other embodiments. Moreover, the blood product solution has a viscosity from approximately 2 centipoise to approximately 4.5 centipoise in particular embodiments.

The present invention also contemplates a method of enhancing oxygen delivery to the tissues of a mammal, comprising a) providing a blood product solution, comprising an oxygen-carrying component and a non-oxygen carrying component, the blood product solution having oncotic pressure higher than that of plasma and viscosity at least half that of blood; and b) administering the blood product solution to the mammal, thereby enhancing oxygen delivery to the tissues of the mammal. In some embodiments, the blood product solution further comprises oxygen affinity equal to or greater than that of blood, while in other embodiments the blood product solution further comprises oxygen capacity less than that of blood. In some embodiments, the oxygen-carrying component is a polyethylene glycol-modified hemoglobin. The non-oxygen-carrying component is a colloid starch in particular embodiments; in some embodiments, the colloid starch has an average molecular weight of from approximately 200,000 daltons to approximately 400,000 daltons. The colloid starch is pentastarch in still further embodiments.

In addition, the present invention contemplates a method of enhancing oxygen delivery to the tissues of a mammal, comprising a) providing a blood product solution, comprising i) an oxygen-carrying component, the oxygen-carrying component comprising a polyethylene glycol-modified hemoglobin, and ii) a non-oxygen carrying component, the non-oxygen carrying component comprising a colloid starch having an average molecular weight of from approximately 200,000 daltons to approximately 350,000 daltons; and b) administering the blood product solution to the mammal, thereby enhancing oxygen delivery to the tissues of the mammal.

In some embodiments, the polyethylene glycol-modified hemoglobin comprises hemoglobin selected from the group consisting of animal hemoglobin, human hemoglobin, and recombinant hemoglobin. In other embodiments, the colloid starch has an average molecular weight of from approximately 200,000 daltons to approximately 400,000 daltons. In still other embodiments, the colloid starch is pentastarch. In particular embodiments, the pentastarch comprises from approximately 20 percent to approximately 80 percent by volume of the blood product.

In certain embodiments, the blood product solution has a viscosity of from approximately 2 centipoise to approximately 4.5 centipoise. Finally, in other embodiments, the mammal is a human.

The present invention also provides an aqueous cell-free composition comprising hemoglobin, in which the hemoglobin is present in a concentration of between 0.1 and 4.0 g/dl, and the aqueous composition has a viscosity that is greater than 2.5 cP. In some preferred embodiments, the viscosity of the aqueous composition is between 2.5 and 4 cP. Thus, it is not intended that the present invention be limited to any viscosity that is greater than approximately 2.5 cP. Indeed, it is contemplated that the present invention encompass compositions in which the viscosity is 6 cP or greater. In addition, the present invention encompasses compositions in which the hemoglobin concentration is less than 0.1 or greater than 4 g/dl, although in particularly preferred embodiments, the hemoglobin concentration is between 0.1 and 4 g/dl. Furthermore, in some embodiments, the $K^*$ of the composition is approximately equal or similar to that of a red blood cell suspension when measured at the same hemoglobin concentration.

In other embodiments of the composition, the hemoglobin has an increased affinity for molecular oxygen as compared to red blood cells. The present invention provides compositions that are suitable for use in any animal, including humans. Thus, in some embodiments, the hemoglobin of the composition has an increased affinity as compared to mammalian red blood cells, although in other embodiments, it is contemplated that the red blood cells are from reptiles, avians, or any other animal. In most preferred embodiments, the red blood cells used in this comparison are human red blood cells. In preferred embodiments, the composition has a P50 of less than 28 mm Hg. However, it is not intended that the present invention be limited to this P50 value, as in some embodiments, the P50 is higher than 28 mm Hg.

In other embodiments, the composition further comprises a diluent selected from the group consisting of proteins, glycoproteins, polysaccharides, and other colloids. It is not intended that these embodiments be limited to any particular diluent. Thus, it is intended that the diluent encompass solutions of albumin, other colloids, or other non-oxygen carrying components. In preferred embodiments, the diluent comprises polysaccharide. In other preferred embodiments, the polysaccharide comprises starch. In particularly preferred embodiments, the starch comprises pentastarch.

In other embodiments, the hemoglobin within the composition is surface-modified. It not intended that these embodiments be limited to any particular type of surface modification. In preferred embodiments, the surface modification includes the use of polyalkylene oxide groups of varying chain lengths and charges. In preferred embodiments, the hemoglobin is surface-modified with polyethylene glycol of varying chain lengths and charges. It is not intended that the surface modification be limited to any particular type or a single type of modification. It is contemplated, that multiple types of surface-modifications will be made to hemoglobin of the composition.

The present invention also provides an aqueous cell-free composition comprising surfaced-modified hemoglobin, wherein the surface-modified hemoglobin is present in a concentration of between 0.1 and 4.0 g/dl, and the aqueous composition has a viscosity that is greater than 2.5 cP. As discussed above, in some preferred embodiments, the viscosity of the aqueous composition is between 2.5 and 4 cP. Thus, it is not intended that the present invention be limited to any viscosity that is greater than approximately 2.5 cP. Indeed, it is contemplated that the present invention encompass compositions in which the viscosity is 6 cP or greater. In further embodiments, the hemoglobin concentration is less than 0.1 or greater than 4 g/dl, although in particularly preferred embodiments, the hemoglobin concentration is between 0.1 and 4 g/dl. In some embodiments, the $K^*$ of the composition is approximately equal or similar to that of a red blood cell suspension when measured at the same hemoglobin concentration.

In preferred embodiments of this composition, the hemoglobin has an increased affinity for molecular oxygen as compared to red blood cells. As above, these embodiments are suitable for use in any animal, including humans. Thus, in some embodiments, the hemoglobin has an increased affinity as compared to mammalian red blood cells, although in other embodiments, it is contemplated that the red blood cells are from reptiles, avians, or any other animal. In most preferred embodiments, the red blood cells used in this comparison are human red blood cells. In other preferred embodiments, the composition has a P50 of less than 28 mm Hg. However, it is not intended that the present invention be limited to this P50 value, as in some embodiments, the P50 is higher than 28 mm Hg.

Furthermore, in other embodiments, the present invention provides compositions which further comprise a diluent selected from the group consisting of proteins, glycoproteins, polysaccharides, and other colloids. It is not intended that the these embodiments be limited to any particular diluent. Thus, it is intended that the diluent encompass solutions of albumin, other colloids, or other non-oxygen carrying components. In preferred embodiments, the diluent comprises polysaccharide. In other preferred embodiments, the polysaccharide comprises starch. In particularly preferred embodiments, the starch comprises pentastarch. In these embodiments, it not intended that the present invention be limited to any particular type of surface modification. In preferred embodiments, the surface modification includes the use of polyalkylene oxide groups of varying chain lengths and charge. In preferred embodiments, the hemoglobin is surface-modified with polyethylene glycol of varying chain lengths and charges.

The present invention further provides an aqueous cell-free composition comprising a mixture of hemoglobin and a diluent, wherein the hemoglobin is present in a concentration between 0.1 and 4 g/dl, and wherein the diluent is selected from the group consisting of proteins, glycoproteins, polysaccharides, and other colloids, and wherein the aqueous composition has a viscosity of at least 2.5 cP. As discussed above, in some preferred embodiments, the viscosity of the aqueous composition is between 2.5 and 4 cP. Thus, it is not intended that these embodiments be limited to any viscosity that is greater than approximately 2.5 cP. Indeed, it is contemplated that the present invention encompass compositions in which the viscosity is 6 cP or greater. Furthermore, in some embodiments, the diluent comprises a polysaccharide, while in preferred embodiments, the diluent comprises starch, and in particularly preferred embodiments, the diluent comprises pentastarch. In addition, the present invention encompasses compositions in which the hemoglobin concentration is less than 0.1 or greater than 4 g/dl, although in particularly preferred embodiments, the hemoglobin concentration is between 0.1 and 4 g/dl. In some embodiments, the K* of the composition is approximately equal or similar to that of a red blood cell suspension when measured at the same hemoglobin concentration.

In some embodiments, the compositions comprise hemoglobin with an increased affinity for molecular oxygen as compared to red blood cells. The present invention provides compositions that are suitable for use in any animal, including humans. Thus, in some embodiments, hemoglobin has an increased affinity as compared to mammalian red blood cells, although in other embodiments, it is contemplated that the red blood cells are from reptiles, avians, or any other animal. In most preferred embodiments, the red blood cells used in this comparison are human red blood cells. In preferred embodiments, the composition has a P50 of less than 28 mm Hg. However, it is not intended that the present invention be limited to this P50 value, as in some embodiments, the P50 is higher.

As indicated above, these embodiments may also comprise hemoglobin that is surface-modified. It not intended that the present invention be limited to any particular type of surface modification. In preferred embodiments, the surface modification includes the use of polyalkylene oxide groups of varying chain lengths and charge. In preferred embodiments, the hemoglobin is surface-modified with polyethylene glycol of varying chain lengths and charges.

The present invention also provides methods comprising providing an animal and an aqueous cell-free composition comprising hemoglobin, wherein the hemoglobin is present in a concentration of between 0.1 and 4.0 g/dl, and the aqueous composition has a viscosity that is greater than 2.5 cP; and administering the aqueous composition to the animal. In preferred embodiments, the animal is a mammal, while in particularly preferred embodiments, the animal is human. In some embodiments, the human is suffering from the symptoms of disease, pathology, insufficiency, or abnormality. In some embodiments, the human has symptoms of disease, wherein the disease is selected from the group consisting of hypovolemic shock symptoms, hypoxia, chronic lung disease, ischemia, stroke, trauma, hemodilution, cardioplegia, cancer, anemia, sickle-cell anemia, septic shock, or disseminated intravascular coagulation. However, it is not intended that the methods of the present invention be limited to the administration of the aqueous composition to alleviate any particular disease, condition, pathology, insufficiency, or abnormality. Rather, it is intended that the methods encompass any and all applications for which the methods are suitable.

As above, the methods of present invention encompass an aqueous cell-free composition comprising hemoglobin, wherein the hemoglobin is present in a concentration of between 0.1 and 4.0 g/dl, and the aqueous composition has a viscosity that is greater than 2.5 cP. In some preferred embodiments, the viscosity of the aqueous composition is between 2.5 and 4 cP. Thus, it is not intended that the present invention be limited to any viscosity that is greater than approximately 2.5 cP. Indeed, it is contemplated that the present invention encompass compositions in which the viscosity is 6 cP or greater. In addition, the present invention encompasses compositions in which the hemoglobin concentration is less than 0.1 or greater than 4 g/dl, although in particularly preferred embodiments, the hemoglobin concentration is between 0.1 and 4 g/dl. In some embodiments, the K* of the composition is approximately equal or similar to that of a red blood cell suspension when measured at the same hemoglobin concentration.

In alternative embodiments, the compositions comprise hemoglobin with an increased affinity for molecular oxygen as compared to red blood cells. In addition, these embodiments are suitable for use with any animal, including humans. Thus, in some embodiments, hemoglobin has an increased affinity as compared to mammalian red blood cells, although in other embodiments, it is contemplated that the red blood cells are from reptiles, avians, or any other animal. In most preferred embodiments, the red blood cells used in this comparison are human red blood cells. In preferred embodiments, the composition has a P50 of less than 28 mm Hg. However, it is not intended that the present invention be limited to this P50 value, as in some embodiments, the P50 is higher than 28 mm Hg.

The other embodiments, the compositions which further comprise a diluent selected from the group consisting of proteins, glycoproteins, polysaccharides, and other colloids. It is not intended that the present invention be limited to any particular diluent. Thus, it is intended that the diluent encompass solutions of albumin, other colloids, or other non-oxygen carrying components. In preferred embodiments, the diluent comprises polysaccharide. In other preferred embodiments, the polysaccharide comprises starch. In particularly preferred embodiments, the starch comprises pentastarch.

In yet other embodiments, the hemoglobin within the composition is surface-modified. It not intended that the present invention be limited to any particular type of surface modification. In preferred embodiments, the surface modification includes the use of polyalkylene oxide groups of varying chain lengths and charge. In preferred embodiments, the hemoglobin is surface-modified with polyethylene glycol of varying chain lengths and charges.

The present invention also provides methods comprising the steps of providing: an organ from an animal, and an aqueous cell-free composition comprising hemoglobin, wherein the hemoglobin is present in a concentration of between 0.1 and 4.0 g/dl, and the aqueous composition has a viscosity that is greater than 2.5 cP; and perfusing the organ with said aqueous composition. In preferred embodiments, the animal is a mammal, while in particularly preferred embodiments, the animal is a human. However, it is not intended that the methods be limited to humans or mammals. In preferred embodiments, the organ is selected from the group consisting of kidneys, liver, spleen, heart, pancreas, lung, and muscle, although it is not intended that the methods of the present be limited to these organs, as any organ may be perfused with the aqueous solution of the present invention.

In some preferred embodiments of the methods, the viscosity of the aqueous composition is between 2.5 and 4 cP. Thus, it is not intended that the present invention be limited to any viscosity that is greater than approximately 2.5 cP. Indeed, it is contemplated that the present invention encompass compositions in which the viscosity is 6 cP or greater. In addition, the present invention encompasses compositions in which the hemoglobin concentration is less than 0.1 or greater than 4 g/dl, although in particularly preferred embodiments, the hemoglobin concentration is between 0.1 and 4 g/dl. In some embodiments, the K* of the composition is approximately equal or similar to that of a red blood cell suspension when measured at the same hemoglobin concentration.

These embodiments also provide compositions comprising hemoglobin with an increased affinity for molecular oxygen as compared to red blood cells. As above, these embodiments are suitable for use in any animal, including humans. Thus, in some embodiments, hemoglobin has an increased affinity as compared to mammalian red blood cells, although in other embodiments, it is contemplated that the red blood cells are from reptiles, avians, or any other animal. In most preferred embodiments, the red blood cells used in this comparison are human red blood cells. In preferred embodiments, the composition has a P50 of less than 28 mm Hg. However, it is not intended that the present invention be limited to this P50 value, as in some embodiments, the P50 is higher than 28 mm Hg.

The other embodiments, the compositions further comprise a diluent selected from the group consisting of proteins, glycoproteins, polysaccharides, and other colloids. It is not intended that the present invention be limited to any particular diluent. Thus, it is intended that the diluent encompass solutions of albumin, other colloids, or other non-oxygen carrying components. In preferred embodiments, the diluent comprises polysaccharide. In other preferred embodiments, the polysaccharide comprises starch. In particularly preferred embodiments, the starch comprises pentastarch.

In yet other embodiments, the hemoglobin within the composition is surface-modified. It not intended that the present invention be limited to any particular type of surface modification. In preferred embodiments, the surface modification includes the use of polyalkylene oxide groups of varying chain lengths and charge. In preferred embodiments, the hemoglobin is surface-modified with polyethylene glycol of varying chain lengths and charges.

It is not intended that the present invention be limited to any particular oncotic pressure. Indeed, it is intended that the compositions of the present invention encompass a range of oncotic pressure. In some embodiments, the oncotic pressure ranges from 70 to 80 mm Hg, while in the most preferred embodiments, the oncotic pressure is approximately 90 mm Hg. However, in other embodiments, the oncotic pressure can be as low as 60 mm Hg. Furthermore, it is intended that the present invention encompass hypooncotic, hyperoncotic, and isooncotic pressures. As used herein, the term "hyperoncotic" encompasses any oncotic pressure that is greater than 25 mm Hg, although in preferred embodiments, solutions with oncotic pressures of 20–60 mm Hg are provided. In some embodiments of the methods of the present invention, it is contemplated that the composition chosen for administration will be customized to the particular needs of the animal. The present invention provides the means to customize the composition to meet the needs of various clinical and veterinary uses.

FIG. 19 provides a graph showing the hemoglobin concentration and viscosity of various hemoglobin preparations. The square positioned within this graph (i.e., at approximately 2.5–4 cP and 0.1 to 4 g/dl hemoglobin) indicates the properties of the most preferred compositions of the present invention. As indicated, the only hemoglobin solution that meets the criteria is the "Hemospan" solution which was made according to the methods of the present invention. The other samples in this graph include blood, PEG-Hb (Enzon), PHP (Apex), and αα-hemoglobin (US Army). As discussed in more detail below, the characteristics of the compositions of the present invention provide many heretofore unknown and unexpected advantages.

The present invention further provides a method comprising: providing i) liganded hemoglobin, ii) means for treating hemoglobin, and iii) means for surface decorating hemoglobin; treating the liganded hemoglobin with the treating means under conditions such that a treated hemoglobin is produced having greater affinity for molecular oxygen than unliganded hemoglobin; and surface decorating the treated hemoglobin with the surface decorating means.

In some embodiments of the method, the means for treating is selected from the group consisting of crosslinking means and polymerizing means. In alternative embodiments, the surface decoration of step (c) comprises reacting said treated hemoglobin with a polyalkylene oxide.

The present invention also provides a method comprising: providing i) liganded hemoglobin, ii) means for treating hemoglobin selected from the group consisting of crosslinking means and polymerizing means, and iii) means for surface decorating hemoglobin; treating the liganded hemoglobin with the treating means under conditions such that a treated hemoglobin is produced having greater affinity for molecular oxygen than unliganded hemoglobin; and surface decorating the treated hemoglobin with the surface decorating means. In some embodiments of the method, the surface decoration of step (c) comprises reacting the treated hemoglobin with a polyalkylene oxide.

The present invention further provides a method comprising: providing i) hemoglobin, ii) means for enzymatically treating hemoglobin (e.g., with enzymes such as carboxy peptidase), and iii) means for surface decorating hemoglobin; treating the liganded hemoglobin with the enzymatic treating means under conditions such that an enzymatically treated hemoglobin is produced having greater affinity for molecular oxygen than hemoglobin in red blood cells; and surface decorating the enzymatically treated hemoglobin with the surface decorating means.

Definitions

To facilitate understanding of the invention set forth in the disclosure that follows, a number of terms are defined below.

The phrase "oxygen capacity less than that of blood" means that when the oxygen capacity of the blood product solutions of the present invention is compared with that of blood, the oxygen capacity of the blood product solutions is less. The oxygen capacity of the blood product solutions of the present invention is not required to be less than that of blood by any particular amount. Oxygen capacity is generally calculated from hemoglobin concentration, since it is known that each gram of hemoglobin binds 1.34 mL of oxygen. Thus, the hemoglobin concentration in g/dL multiplied by the factor 1.34 yields the oxygen capacity in mL/dL. The present invention contemplated the use of a suitable commercially available instruments to measure hemoglobin concentration, including the B-Hemoglobin Photometer (Hemocue, Inc.). Similarly, oxygen capacity can be measured by the amount of oxygen released from a sample of hemoglobin or blood by using, for example, a fuel-cell instrument (e.g., Lex-O$_2$-Con; Lexington Instruments).

The phrase "oxygen affinity equal to or greater than that of blood" means that when the oxygen affinity of the blood product solutions of the present invention is compared with that of blood, the oxygen affinity of the blood product solutions is greater. The oxygen capacity of the blood product solutions of the present invention is not required to be greater than that of blood by any particular amount. The oxygen affinity of whole blood (and components of whole blood such as red blood cells and hemoglobin) can be measured by a variety of methods known in the art. (See, e.g., Vandegriff and Shrager in *Methods in Enzymology* (Everse et al., eds.) 232:460 [1994]). In preferred embodiments, oxygen affinity may be determined using a commercially available HEMOX® Analyzer (TCS Medical Products). (See, e.g., Winslow et al., J. Biol. Chem., 252(7): 2331–37 [1977]).

The phrase "oncotic pressure higher than that of plasma" means that when the oncotic pressure of the blood product solutions of the present invention is compared with that of plasma, the oncotic pressure of the blood product solutions is greater. The oncotic pressure of the blood product solutions of the present invention is not required to be greater than that of blood by any particular amount. Oncotic pressure may be measured by any suitable technique; in preferred embodiments, oncotic pressure is measured using a Colloid Osmometer (Wesco model 4420).

The phrase "viscosity at least half of that of blood" means that when the viscosity of the blood product solutions of the present invention is compared with that of blood, the viscosity of the blood product solutions is at least 50% of that of blood; in addition, the viscosity may be greater than that of blood. Preferably, viscosity is measured at 37° C. in a capillary viscometer using standard techniques. (See Reinhart et al, J. Lab. Clin. Med. 104:921–31 [1984]). Moreover, viscosity can be measured using other methods, including a rotating cone-and-plate viscometer such as those commercially available from Brookfield. The viscosity of blood is approximately 4 centipoise. Thus, at least half of the blood value corresponds to at least approximately 2 centipoise.

The term "blood product" refers broadly to formulations capable of being introduced into the circulatory system of the body and carrying and supplying oxygen to the tissues. While the term "blood products" includes conventional formulations (e.g., formulations containing the fluid and/or associated cellular elements and the like that normally pass through the body's circulatory system, including, but not limited to, platelet mixtures, serum, and plasma), the preferred blood products of the present invention are "blood product mixtures." As used herein, blood product mixtures comprise a non-oxygen-carrying component and an oxygen-carrying component.

The term "oxygen-carrying component" refers broadly to a substance capable of carrying oxygen in the body's circulatory system and delivering at least a portion of that oxygen to the tissues. In preferred embodiments, the oxygen-carrying component is native or modified hemoglobin. As used herein, the term "hemoglobin" refers to the respiratory protein generally found in erythrocytes that is capable of carrying oxygen. Modified hemoglobin includes, but is not limited to, hemoglobin altered by a chemical reaction such as cross-linking, polymerization, or the addition of chemical groups (e.g., polyethyleneglycol, polyoxyethylene, or other adducts). Similarly, modified hemoglobin includes hemoglobin that is encapsulated in a liposome.

The present invention is not limited by the source of the hemoglobin. For example, the hemoglobin may be derived from animals and humans; preferred sources of hemoglobin are cows and humans. In addition, hemoglobin may be produced by other methods, including recombinant techniques. A most preferred oxygen-carrying-component of the present invention is "polyethylene glycol-modified hemoglobin."

The term "polyethylene glycol-modified hemoglobin" refers to hemoglobin that has been modified such that it is associated with polyethylene glycol ($\alpha$-Hydro-$\omega$-hydroxy-poly-(oxy-1,2-ethanediyl); generally speaking, the modification entails covalent binding of polyethylene glycol (PEG) to the hemoglobin. PEGs are liquid and solid polymers of the general chemical formula $H(OCH_2CH_2)_nOH$, where n is greater than or equal to 4. PEG formulations are usually followed by a number that corresponds to its average molecular weight; for example, PEG-200 has a molecular weight of 200 and a molecular weight range of 190–210. PEGs are commercially available in a number of formulations (e.g., Carbowax, Poly-G, and Solbase).

The term "non-oxygen-carrying component" refers broadly to substances like plasma expanders that can be administered, e.g., for temporary replacement of red blood cell loss. In preferred embodiments of the invention, the non-oxygen-carrying component is a colloid (i.e., a substance containing molecules in a finely divided state dispersed in a gaseous, liquid, or solid medium) which has oncotic pressure (colloid osmotic pressure prevents, e.g., the fluid of the plasma from leaking out of the capillaries into the interstitial fluid). Examples of colloids include hetastarch, pentastarch, dextran-70, dextran-90, and albumin.

Preferred colloids of the present invention include starches like hetastarch and pentastarch. Pentastarch (hydroxyethyl starch) is the preferred colloid starch of the present invention. Pentastarch is an artificial colloid derived from a starch composed almost entirely of amylopectin. Its molar substitution is 0.45 (i.e., there are 45 hydroxyethyl groups for every 100 glucose units); hydroxyethyl groups are attached by an ether linkage primarily at C-2 of the glucose unit (and less frequently at C-3 and C-6). The polymerized glucose units of pentastarch are generally connected by 1–4 linkages (and less frequently by 1–6 linkages), while the degree of branching is approximately 1:20 (i.e., there is one branch for every 20 glucose monomer units). The weight average molecular weight of pentastarch is about 250,000 with a range of about 150,000 to 350,000. Unless otherwise indicated, reference to the "average molecular weight" of a substance refers to the weight average molecular weight. Pentastarch is commercially available (e.g., DuPont Merck) as a 10% solution (i.e., 10 g/100 mL); unless otherwise indicated, reference to blood product solutions comprising pentastarch (and other non-oxygen-carrying components as well as oxygen-carrying components) is on a volume basis.

The phrase "enhancing oxygen delivery to the tissues of a mammal" refers to the ability of a fluid (e.g., a blood product) introduced into the circulatory system to deliver more oxygen to the tissues than would be delivered without introduction of the fluid. To illustrate, a patient may experience substantial blood loss following acute hemorrhage, resulting in decreased transport of oxygen to the tissues via the blood. The administration of a blood product to the patient can supplement the ability of the patient's own blood to deliver oxygen.

The term "mixture" refers to a mingling together of two or more substances without the occurrence of a reaction by which they would lose their individual properties. The term "solution" refers to a liquid mixture. The term "aqueous solution" refers to a solution that contains some water. In many instances, water serves as the diluent for solid substances to create a solution containing those substances. In other instances, solid substances are merely carried in the aqueous solution (i.e., they are not dissolved therein). The term aqueous solution also refers to the combination of one or more other liquid substances with water to form a multi-component solution.

The term "approximately" refers to the actual value being within a range of the indicated value. In general, the actual value will be between 10% (plus or minus) of the indicated value.

DESCRIPTION OF THE DRAWINGS

FIG. 6A–D graphically depict the acid-base status of control rats (♦) and of rats following exchange transfusion with pentastarch (▲), αα-Hb (■), PEG-Hb (●), pentastarch+αα-Hb (□), and pentastarch+PEG-Hb (○) and after the initiation of a 60% hemorrhage. FIG. 6A depicts $PaO_2$, FIG. 6B depicts $PaCO_2$, FIG. 6C depicts arterial pH, and FIG. 6D depicts base excess.

FIG. 7 graphically depicts the production of lactic acid in control rats (♦) and of rats following exchange transfusion with pentastarch (▲), αα-Hb (■), PEG-Hb (●), pentastarch+αα-Hb (■), and pentastarch+PEG-Hb (○) and after the initiation of a 60% hemorrhage.

FIG. 8A depicts mean arterial blood pressure in control rats (♦) and of rats following exchange transfusion with pentastarch (▲), PEG-Hb (●), and PENTASPAN®+PEG-Hb (○) at time −30 minutes, and after the initiation of a 60% hemorrhage at time 0 minutes.

FIG. 8B depicts mean arterial blood pressure in control rats (♦), and rats following exchange transfusion with pentastarch (▲, point B), αα-Hb (■, point B), and pentastarch+αα-Hb (□, point A), and after the initiation of a 60% hemorrhage (point C).

DESCRIPTION OF THE INVENTION

Figure 1:
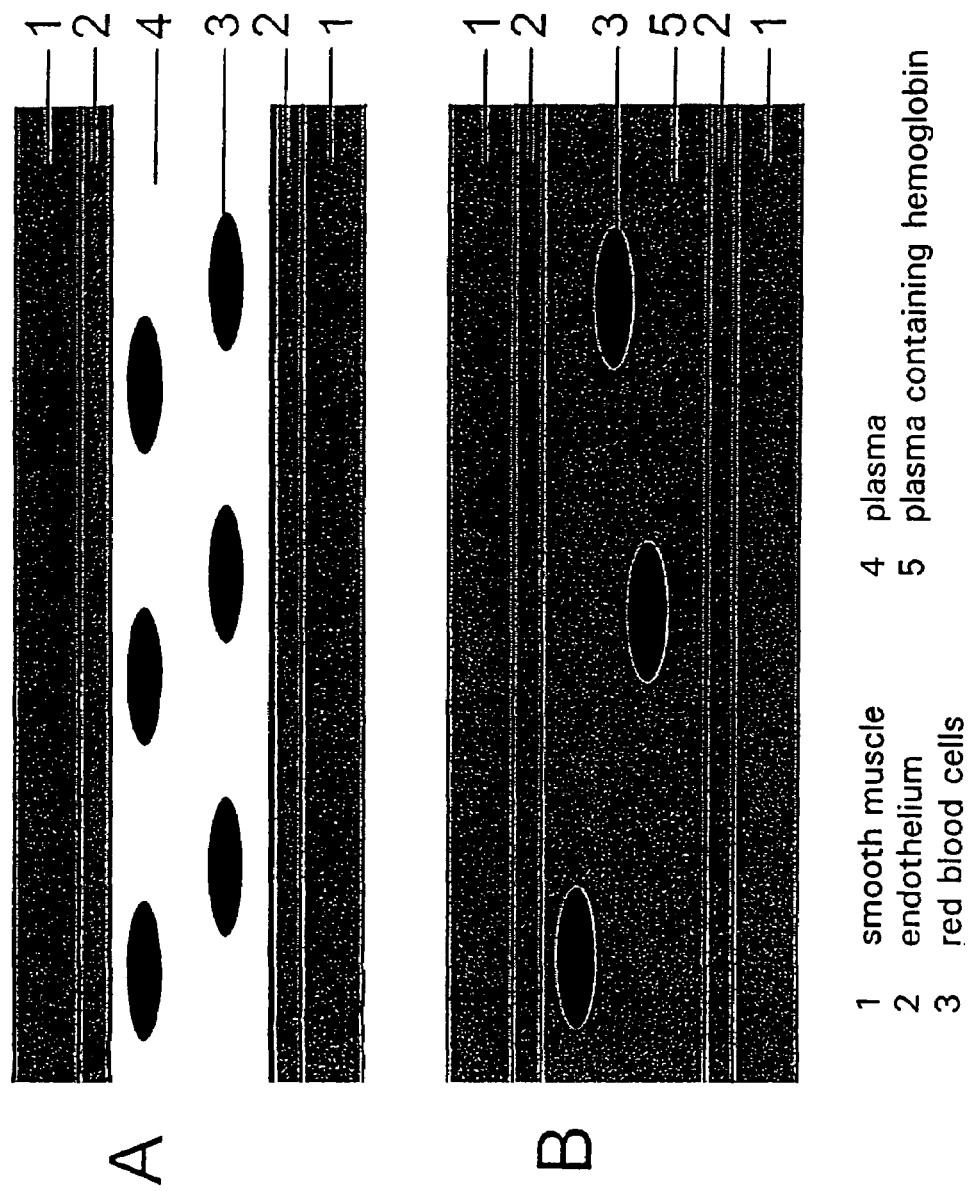
FIGS. 1A–B are a diagrammatic cross-sectional illustration of the flow of whole blood (FIG. 1A) and a hemoglobin-based oxygen carrier (FIG. 1B) through an arterial vessel.

The present invention relates generally to blood products, and more particularly to compositions comprising a mixture of an oxygen-carrying component and a non-oxygen-carrying component and methods for the use thereof. The compositions and methods of the present invention result in improved oxygen delivering capacity of hemoglobin-based oxygen carriers. Generally speaking, the compositions of the present invention will exhibit one or more of the following properties: i) viscosity at least half that of blood; ii) oncotic pressure higher than that of plasma; iii) hemoglobin oxygen affinity higher than or equal to (i.e., P50 equal to or lower than) that of blood; and iv) oxygen capacity less than that of blood. Because of the more efficient utilization of the oxygen carried by the HBOC in terms of tissue oxygenation, the compositions of the present invention comprise a substantially reduced hemoglobin content and are generally less expensive to formulate.

The description of the invention is divided into: I) The Nature of Oxygen Delivery and Consumption; II) Facilitated Diffusion and The Design of Hemoglobin-Based Oxygen Carriers; III) Clinical and Other Applications of the Present Invention; IV) The Oxygen-carrying Component of the Blood Products of the Present Invention; V) The Non-oxygen Carrying Component of the Blood Products of the Present Invention; and VI) Blood Product Compositions. Each section will be discussed in turn below.

I. The Nature of Oxygen Delivery and Consumption

Although the successful use of the compositions and methods of the present invention do not require comprehension of the underlying mechanisms of oxygen delivery and consumption, basic knowledge regarding some of these putative mechanisms may assist in understanding the discussion that follows. As previously indicated, it has generally been assumed that the capillaries are the primary conveyors of oxygen to the tissue; however, regarding tissue at rest, current findings indicate that there is approximately an equipartition between arteriolar and capillary oxygen release. That is, hemoglobin in the arterial system is believed to deliver approximately one-third of its oxygen content in the arteriolar network and one-third in the capillaries, while the remainder exits the microcirculation via the venous system. The arteries themselves comprise a site of oxygen utilization (e.g. the artery wall requires energy to effect regulation of blood flow through contraction against vascular resistance). Thus, the arterial wall is normally a significant site for the diffusion of oxygen out of the blood. However, current oxygen-delivering compositions (e.g., HBOCs) may release too much of their oxygen content in the arterial system, and thereby induce an autoregulatory reduction in capillary perfusion.

The rate of oxygen consumption by the vascular wall, i.e., the combination of oxygen required for mechanical work and oxygen required for biochemical synthesis, can be determined by measuring the gradient at the vessel wall. Present technology allows accurate oxygen partial pressure measurements in vessels on the order of 50 microns diameter. The measured gradient is directly proportional to the rate of oxygen utilization by the tissue in the region of the measurement. Such measurements show that the vessel wall has a baseline oxygen utilization which increases in inflammation and constriction, and is lowered by relaxation.

The vessel wall gradient is inversely proportional to tissue oxygenation. Vasoconstriction increases the oxygen gradient (tissue metabolism), while vasodilation lowers the gradient. Higher gradients are indicative of the fact that more oxygen is used by the vessel wall, while less oxygen is available for the tissue. The same phenomenon is believed to be present throughout the microcirculation.

The present invention demonstrates that increased blood $PO_2$ (which can be obtained, e.g., by hemodilution) through administration of a conventional oxygen—carrying solution (e.g., a HBOC), though superficially a beneficial outcome of the altered blood flow characteristics and blood oxygen carrying capacity of the resulting circulatory fluid, carries with it significant disadvantages. That is, when the hemoglobin carrying the oxygen is evenly distributed in the vessel as opposed to being contained in RBCs, a different set of factors influencing oxygen delivery apparently come into play. The present invention provides a means of alleviating these disadvantages, namely by providing and using an aqueous solution of an oxygen-carrying component (e.g., modified hemoglobin) and a non-oxygen-carrying component (e.g., a non-proteinaceous colloid such as dextran or pentastarch). Among other attributes, the compositions of the present invention can be manufactured at a much lower cost than that of normal HBOCs and provide a blood substitute of increased viscosity.

FIG. 1A diagrammatically illustrates, in cross section, an arteriole having a wall (2) surrounding the flow passage therethrough. The wall in turn, is surrounded by muscle (1). As previously indicated, normal whole blood consists essentially of red blood cells (3) and plasma (4). Substantially all (approximately 97%) of oxygen carried by the blood is associated with the hemoglobin and is inside the red blood cells (3); only about 3% of the oxygen is in the plasma component.

Accordingly, the oxygen availability to the artery wall (2) is limited by the surface area of the RBCs and the rate of diffusion of oxygen through the RBC membrane and surrounding unstirred plasma. The artery walls receive an amount of oxygen proportional to the spacing between RBCs and the mean distance for diffusion from RBCs to the wall.

For comparison purposes, FIG. 1B diagrammatically illustrates oxygen delivery when an artery is perfused with a HBOC (5) mixed with whole blood. In this situation, the component of the HBOC that directly binds oxygen is homogeneously distributed throughout the HBOC (5) and the oxygen is available for diffusion to all parts of the surface of the artery wall (2). Thus, oxygen availability to the artery wall (2) is greatly increased, effectively causing an increase of $PO_2$ in the arterial system. Though the present invention does not require an understanding of the precise mechanisms, it is believed that arterial wall and muscle reactions (e.g., increased metabolism of the cellular components of the vessel wall as a consequence of energy-consuming vasoconstrictor effects) take place in an attempt to maintain the $PO_2$ of the tissue; this is evidenced by the establishment of a large gradient of oxygen partial pressure across the arterial wall aimed at maintaining arteriolar partial oxygen pressure constant. As a result, there is excessive loss of oxygen from the blood-HBOC mixture at the arterial walls, and, concomitantly, insufficient oxygen is available for capillary delivery to the tissues.

Though a precise understanding of the underlying mechanism is not required in order to practice the present invention, the present invention is based upon the discovery that a HBOC tends to release too much of the oxygen it carries at the artery walls, resulting in reaction of the arterial walls to the excess oxygen and oxygen deficiency at the capillaries. As alluded to above, researchers have previously assumed that administration of a blood substitute (e.g., a HBOC) should result in physiological cardiovascular responses similar to those observed upon administration of non-oxygen carrying diluent materials of similar molecular weight. However, it has been observed that HBOCs cause physiological reactions that differ from those found with non-oxygen-carrying plasma expanders. The dilution of RBCs, accompanied by the maintenance of intrinsic oxygen delivering capacity of the composition (i.e., because the blood substitute composition is itself an oxygen carrier), changes the distribution of oxygen in the circulatory system, increasing the $PO_2$ in the arteriolar segment. As discussed further below, this in turn appears to lead to the reaction of the muscles lining the arterial walls to the excess oxygen availability. In contrast, the compositions of the present invention result in increased oxygen delivery to the tissues surrounding the capillaries.

As set forth in the preceding discussion, the suitability of a blood product should be determined by analysis of its systemic effects, and how such effects, in conjunction with the altered transport properties of the circulating fluid, influence transport microcirculatory function.

II. Facilitated Diffusion and the Design Of Hemoglobin-Based Oxygen Carriers

Vasoconstriction is one of the most perplexing problems in the development of a safe and efficacious red cell substitute. When infused into animals and humans, many hemoglobin-based solutions produce significant hypertension, increased vascular resistance and decreased $O_2$ transport. This phenomenon has been observed in both the systemic and pulmonary circulations in models of clinical use (Hess et al., J. Appl. Physiol., 74: 1769–78 [1993], Keipert et al., Transfusion 33: 701–8 [1993]) and in humans (Kasper et al., Biochem., 31: 7551–9 [1992]).

Vasoactivity is usually attributed to the avidity with which hemoglobin combines with nitric oxide, the endothelium-derived relaxing factor. The NO affinity of model hemoglobins however does not correlate with the effect on mean arterial blood pressure in rats (Rohlfs et al., In R. M. Winslow et al., (eds.), *Advances in Blood Substitutes. Industrial Opportunities and Medical Challenges*, Birkhauser, Boston [1997], pp. 298–327 [1997]), and it is possible that oversupply of $O_2$ due to diffusion of $HbO_2$ or removal of NO due to diffusion of HbNO also plays an additional, if not exclusive, role.

Increased rates of $O_2$ uptake and release by cell-free hemoglobin compared to red blood cells have been predicted (See e.g., Homer, Microvasc. Res., 22: 308–23 [1981]; Federspiel and Popel, Microvasc. Res., 32: 164–189 [1986]) and shown in vitro (Page et al., In R. M. Winslow et al., (eds.), *Blood Substitutes: New Challenges*, Birkhauser, Boston [1996], pp. 132–145). However, attempts to demonstrate augmented transport by $O_2$ diffusion in vivo by cell-free hemoglobin have been unsuccessful (See, Biro, Can. J. Physiol. Pharmacol., 69: 1656–1662 [1991]; Hogan et al., Adv. Exp. Med. Biol., 361: 375–378 [1994]; and Hogan et al., J. Appl. Physiol., 361: 2470–5 [1992]). Although an understanding of the mechanism is not necessary in order to make and use the present invention, during the development of the present invention, it was determined, shown, by measurements in artificial capillaries, that cell-free hemoglobin does, indeed, increase the availability of $O_2$ to the surrounding medium.

In normal blood, $O_2$ moves from the red blood cell to the vessel wall by simple diffusion. When hemoglobin is present in the plasma space, $O_2$ can also move bound to hemoglobin as $HbO_2$. This second process is called "facilitated diffusion." During the development of the present invention, properties of cell-free hemoglobin that modulate this facilitated diffusion were identified. Using this knowledge, hemoglobins that demonstrate diffusive $O_2$ transport similar to that of red blood cells by reduced facilitated diffusion were prepared. It was also confirmed that these example molecules do not produce vasoconstriction in animals. Surprisingly, it was found that increased viscosity, increased $O_2$ affinity (reduced P50), and increased molecular size are the key properties required for a cell-free hemoglobin to avoid vasoactivity and to enable success as a red cell substitute.

In addition, the present invention provides teachings regarding the optimal properties of hemoglobin-based blood substitutes in regard to oxygen affinity, viscosity and molecular size and a method to evaluate such products by an instrument based on an artificial capillary. This method enables the quantitative determination of the ability of a blood substitute to transfer $O_2$ (or any other gas such as $CO_2$, NO, or CO) across a capillary membrane as a model of in vivo gas transfer.

A. Facilitated Diffusion

During the development of the present invention, it was shown that unexpectedly, arterioles, particularly at the A2/A3 level consume large amounts of $O_2$. This was determined by a technique for measuring $O_2$ concentration in localized areas of the microcirculation (Torres and Intaglietta, Am. J. Physiol., 265: H1434–H1438 [1993]). These results indicate that these arterioles are capable of prodigious metabolic activity. Innervation of these arterioles is particularly dense (Saltzman et al., Microvasc. Res., 44: 263–273 [1992]), suggesting that they regulate downstream capillary blood flow. Based on these results, increasing the $O_2$ available to these arterioles would be expected to provide a potent stimulus to engage mechanisms that regulate the delivery of $O_2$ to capillary beds (autoregulation). Although an understanding of the exact biochemical mechanism(s) which underlie these events is not necessary in order to use the present invention, it is contemplated that they could be mediated by $O_2$— or NO— sensitive pathways; the presence of hemoglobin, free in the plasma space, as in a "blood substitute" is likely to engage these mechanisms because of its capacity for facilitated diffusion.

The transport of $O_2$ in the blood by two pathways ($O_2$ and $HbO_2$ diffusion) can be expressed mathematically. The transport (flux, –J) of $O_2$ to the vessel wall is the sum of the diffusion of free ($O_2$) and chemically bound oxygen ($HbO_2$):

$$-J = \frac{D_{O_2} \alpha \Delta PO_2}{\Delta X} + \frac{D_{HbO2} [Hb]_T \Delta Y}{\Delta X} \quad (1)$$

where $D_{O2}$ and $D_{HbO2}$ are the diffusion constants for $O_2$ and cell-free $HbO_2$, respectively, $\alpha$ is the solubility of $O_2$ in plasma, $\Delta PO_2$ is the difference in partial pressure of $O_2$ inside and outside the vessel, $\Delta Y$ is the gradient of hemoglobin saturation from the center of the vessel to its wall, and $[Hb]_T$ is the total cell-free hemoglobin concentration. $D_{O2}$ and $D_{HbO2}$ have been measured experimentally in static solution (Table 1). The distance for diffusion, $\Delta X$, is considered to be the same for the two molecules, $O_2$ and $HbO_2$. The references cited in Table 1 are: Wittenberg, Physiol. Rev., 50(4): 559–636 [1970], and Bouwer, Biochim. Biophys. Acta 1338: 127–136 [1977]).

TABLE 1

Values For Diffusion Constants From The Literature

| | $D_{O2}$ (cm$^2$/sec) | $D_{HbO2}$ (cm$^2$/sec) |
|---|---|---|
| Wittenberg | 2.13 × 10$^{-5}$ | 11.3 × 10$^{-7}$ |
| Bouwer | 1.40 × 10$^{-5}$ | 7.0 × 10$^{-7}$ |
| Mean | 1.76 × 10$^{-5}$ | 9.15 × 10$^{-7}$ |

Table 1 shows that $D_{HbO2}$ is about $\frac{1}{20}^{th}$ of $D_{O2}$. However because the solubility of $O_2$ in plasma is low ($\alpha$=1.2074 µM/Torr), and $D_{O2}$ is relatively high, when plasma hemoglobin concentration is only 3 mM (4.83 g/dl) at $PO_2$ of 100 Torr, the product of diffusion and concentration (the numerators in equation 1) for free $O_2$ and $HbO_2$ are nearly equal. Thus plasma hemoglobin contributes as much $O_2$ as dissolved $O_2$, effectively doubling the amount of $O_2$ available from red blood cells. These relationships are shown quantitatively in Table 2.

TABLE 2

The Product Of Diffusion And Concentration For Dissolved $O_2$ vs. $HbO_2$

| | Concentration at 100 Torr, mM | Diffusion constant (see table 3) | Concentration × Diffusion |
|---|---|---|---|
| $O_2$ | 0.1207 | 176 × 10$^{-7}$ | 2.48 × 10$^{-6}$ |
| $HbO_2$ | 3.0 | 9.15 × 10$^{-7}$ | 2.74 × 10$^{-6}$ |

In order to develop a strategy to minimize the facilitated diffusion of $O_2$ by plasma $HbO_2$, it was necessary to analyze the biophysical properties which contribute to it. Because water is much smaller than $HbO_2$, $D_{HbO2}$ is a function of viscosity and molecular radius, as defined by the Stokes-Einstein equation:

$$D_{HbO_2} = \frac{kT}{6\pi\eta_{solution} r_{HbO_2}} \quad (2)$$

where k is Boltzman's constant, $\eta_{solution}$ is the viscosity of the solution, and $r_{HbO2}$ is the radius of the hemoglobin molecule ($HbO_2$). For molecular oxygen, where the molecular radius ($r_{O2}$) is approximately the same as that of water, the Stokes-Einstein equation becomes:

$$D_{O_2} = \frac{kT}{4\pi\eta_{solution} r_{O_2}} \quad (3)$$

Thus, for both $HbO_2$ and dissolved $O_2$ their diffusivities are inversely related to the viscosity of the macromolecular solutions. For cell-free hemoglobin, hemoglobin molecular size is an additional factor in that $D_{HbO2}$ is inversely proportional to the molecular size of hemoglobin ($r_{HbO2}$ in Equation 2). Thus this analysis predicts that two potential strategies to reduce or eliminate facilitated diffusion by cell-free hemoglobin is increasing the molecular radius of the molecule and increasing solution viscosity.

Further analysis of the equation 1 leads to an understanding of an additional strategy to defeat this mechanism. The gradient along which $HbO_2$ diffuses is $[Hb]_T \Delta Y$ and the distance through which $HbO_2$ must diffuse ($\Delta X_{HbO2}$). The quantity $\Delta Y$ at a given $PO_2$ is the slope of the oxygen equilibrium curve at that $PO_2$ and is dependent on the shape of the curve (a property of the hemoglobin molecule) and its position (i.e., P50).

To summarize, the total $O_2$ transferred in a cylindrical section of the Krogh cylinder (see FIG. 1) can be described as follows:

$$\Delta O_{2_r} = \left(\frac{\pi r^2}{R}\right)\left[\left(\frac{D_{O_2} \alpha \Delta PO_2}{\Delta X_{O_2}}\right) + \left(\frac{D_{HbO_2}[Hb]_T \Delta Y}{\Delta X_{HbO_2}}\right)\right] \quad (4)$$

In this equation, r is the radius of the capillary, and R is the flow rate. The equation shows the contribution of $HbO_2$ diffusion to total $O_2$ transport. This form of the $O_2$ transfer equation has the interesting property in that it shows that the contribution of the $HbO_2$ diffusion is dependent on 4 variables: the diffusion constant ($D_{HbO2}$), hemoglobin concentration ($[Hb]_T$), the difference in saturation between the center and the edge of the capillary ($\Delta Y$) and the distance for diffusion of $HbO_2$ ($\Delta X_{HBO2}$).

Equation 4 reveals a number of strategies that can be employed independently or in combination to modulate $O_2$ flux ($\Delta O_{2T}$). The strategies are defined by the relationship of $\Delta O_{2T}$ to the alterable solution properties such that $\Delta O_{2T}$ is:
    (1) inversely proportional to solution viscosity ($\eta$), according to Eqs. 2 and 3, through changes in both $DO_2$ and $DHbO_2$;
    (2) inversely proportional molecular size ($r_{HbO2}$), according to Eq. 2, through a change $D_{HbO2}$;
    (3) directly proportional to [Hb]T; and
    (4) directly proportional to $\Delta Y$ ($\Delta Y$ can be altered by changing $O_2$ affinity and/or cooperativity of $O_2$ binding).

Thus, to minimize effects of facilitated diffusion on $\Delta O_{2T}$ from cell-free hemoglobin-based oxygen carriers, a given $\Delta O_{2T}$ based on the value for red blood cells can be achieved using the above strategies independently or in combination. For the purpose of example, $\Delta O_{2T}$ can be decreased to within a desired range by:
    (1) altering a single parameter independently through:
        increasing $\eta$;
        increasing $r_{HbO2}$;
        decreasing [Hb]T or
        adjusting $\Delta Y$ through its $O_2$ affinity and/or cooperativity;
    (2) altering any combination of the above properties such that, quantitatively, $\Delta O_{2TT}$ is within the desired range.

B. Evaluation of Cell-Free Hemoglobins

Figure 13:
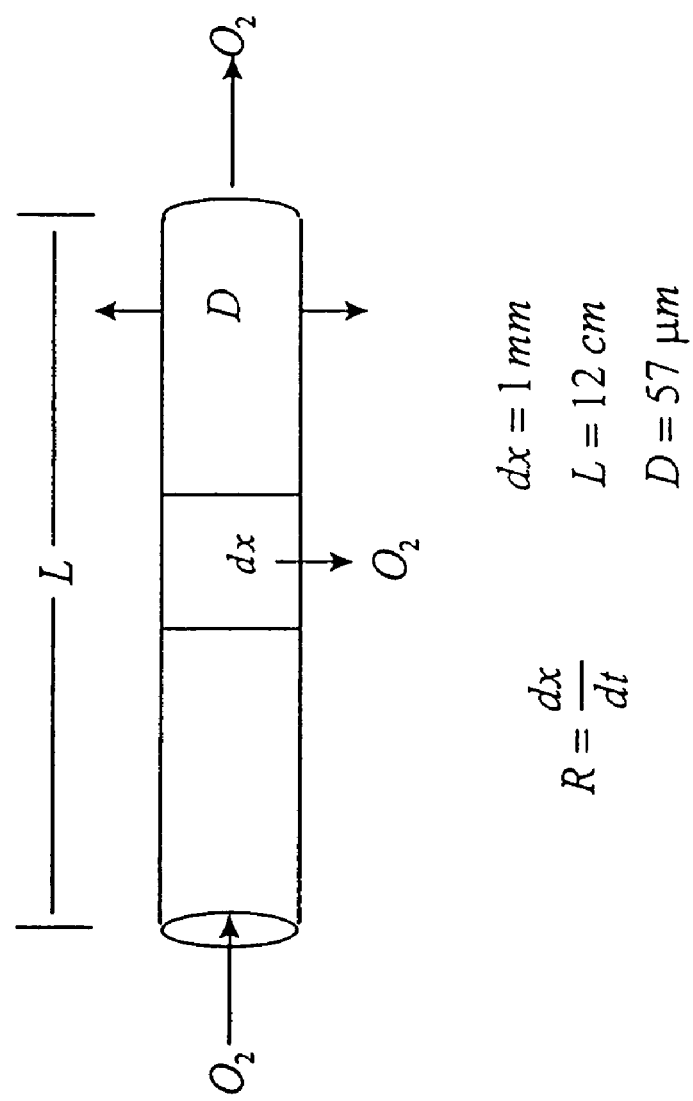
FIG. 13 provides an illustration of a Krogh cylinder.

Evaluation of cell-free hemoglobins with regard to their facilitated diffusion of oxygen and hence their potential to produce autoregulatory vasoactivity in arterioles is based on the Krogh cylinder, an idealized segment of vessel (See FIG. 13). Through a detailed analysis of the shape and position of the oxygen equilibrium curve, the amount of $O_2$ delivered to this sensitive region is analyzed as a function of diffusion, hemoglobin concentration, and P50.

1. Artificial Capillary System

Figure 14:
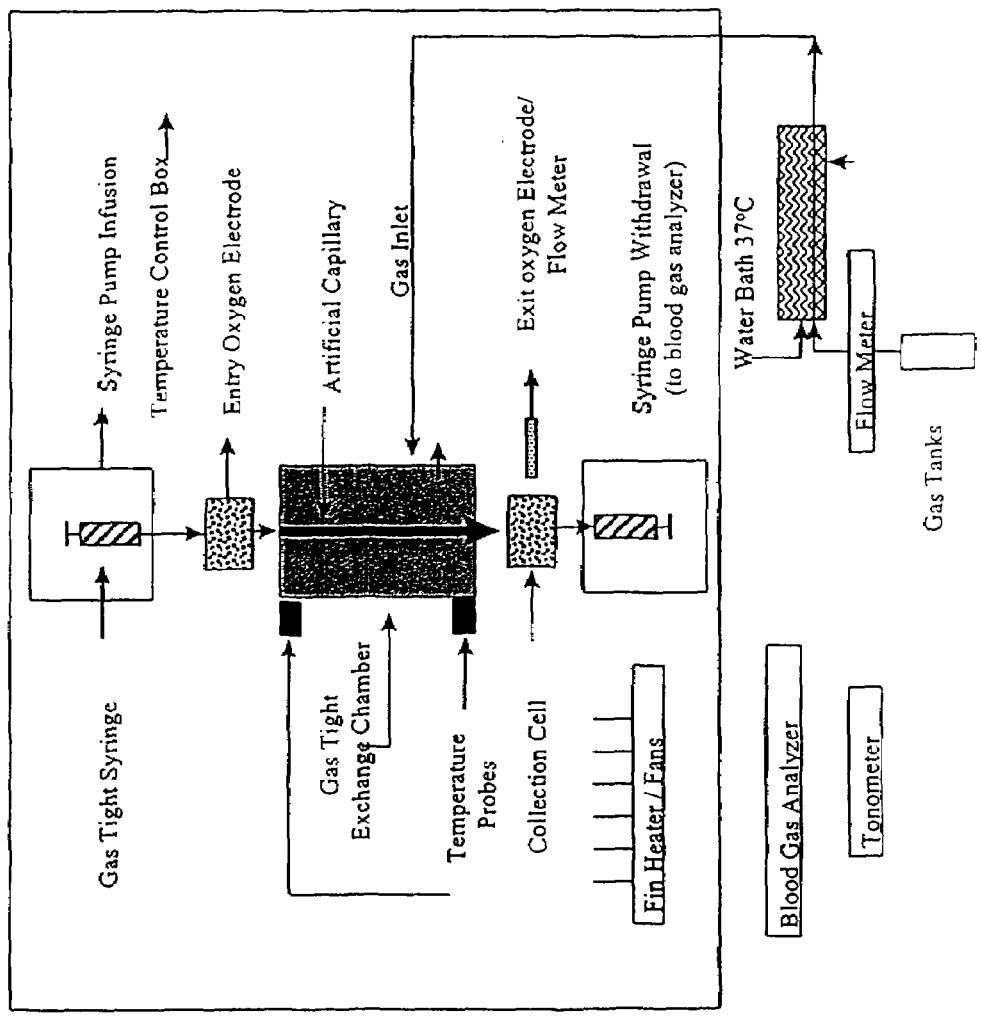
FIG. 14 provides a schematic of a capillary system.

The artificial capillary system is shown diagrammatically in FIG. 14. The capillary is polydimethylsiloxane (e.g., Silastic, Point Medical Corporation, Crown Point, Ind.) with a wall thickness approximately the same size as the diameter (57 µm). The glass capillary is a 2 µl pipette (e.g., Drummond Scientific, Broomall, Pa.). The glass and silicone junction is sealed with a silicone sealant (e.g., RTV 60, General Electric). The typical length of a capillary, 100 mm, produces residence times similar to in vivo times (i.e., 0.37 sec –1.5).

The infusion syringe pump (e.g., KD Scientific, Boston, Mass.) is connected to the entry oxygen flow cell by a short length of low-permeable Tygon tubing. The Clark-type oxygen electrodes (e.g., Instech, Plymouth Meeting, Pa.) are used to monitor the system. Data collection is accomplished by analysis of the effluent fluid with a blood-gas analyzer (ABL-5, Radiometer). The exit from the flow cell is connected to another short length of Tygon tubing, which in turn is tightened to the glass capillary of the silicone capillary unit by the use of a micro-tube connector (e.g., Cole-Palmer, Niles, Ill.). The artificial capillary is encased in a gas-tight exchange chamber made of clear acrylic plastic. Bimetallic temperature probes (e.g., YSI 700, Yellow Springs, Ohio) are attached near the entry and exit points of the fluid flow to ensure proper temperature control and held constant at 37° C.

The collection cell is mated directly to the end of the artificial capillary unit by use of a silicone sealant and a polypropylene microfitting (Cole-Palmer). The collection cell is solid acrylic with a T shaped channel (diameter of 0.75 mm) drilled through it. The first channel is shunted through a calibrated measuring tube that serves as a flow meter. Periodically the flow meter can be replaced with an oxygen electrode to monitor system conditions. The second flow channel is directed toward the back of the collection cell, where a gas-tight septum seals the exit. A Hamilton gas-tight syringe (Hamilton Co., Reno, Nev.) pierces this septum and collects the sample as a syringe pump slowly withdraws fluid at a rate lower than the flow rate in the capillary. This entire apparatus is enclosed within an acrylic container which maintains the temperature 37° C. through the use of a fin heater.

2. Artificial Capillary Experimental Protocol

The equilibrated samples are aspirated from the tonometer into a Hamilton gas-tight syringe which is mounted onto the infusion pump. Constant flow is established throughout the system to achieve the desired residence time. The test solutions are equilibrated with 20% $O_2$, balance $N_2$, to simulate air. The chamber outside of the capillary is filled with 100% $N_2$. The inlet gas is routed through a 37° C. water bath and a flow meter to maintain constant flow rate, so that the volume of gas in the chamber is exchanged every 10 seconds. Oxygen electrodes monitor the extracapillary gas compartment.

The effluent from the capillary is collected in a second Hamilton gas-tight syringe and is injected into the blood gas analyzer (e.g., ABL-5, Radiometer, West lake, OH). A minimum of three samples are taken at each residence time. Flow conditions are changed, and a new set of samples is tested. Three flow rates, 10, 20 and 40 μl/min, give residence times in the capillary of 1.56, 0.75 and 0.39 seconds, respectively.

3. Mathematical Analysis Of Artificial Capillary Data

For each segment (dx, FIG. 13) of distance along the capillary, the total $O_2$ present in the solution is:

$$O_{2_2} = \alpha PO_2 + Y[Hb]_T \quad (5)$$

where α is the solubility coefficient of $O_2$ in plasma (1.2074 μM/Torr) (Winslow et al., J. Biol. Chem., 252(7):2331–2337 [1977]), Y is hemoglobin saturation, and $[Hb]_T$ is total hemoglobin concentration. The amount of $O_2$ transferred out of the capillary in the segment dx is $$\Delta O_2 = \frac{K^*(\Delta PO_2)(\pi r^2)dx}{R} \quad (6)$$

where K* is a lumped diffusion parameter, consisting of the diffusion constants given in equation 1 and the length of the diffusion gradient for $O_2$, $\Delta PO_2$ is the $PO_2$ gradient (essentially the interior $PO_2$ when $N_2$ is the outside gas), r is the radius of the capillary, and R is the flow rate. Total $O_2$ is now decremented by $\Delta O_2$. At this point, the Adair equation, using the known parameters for the hemoglobin in question, is used to empirically find the $PO_2$ and Y combination that provide the new $O_{2_T}$ according to equation (5). The process is repeated until the end of the capillary is reached, and the final $PO_2$ is matched with the value actually measured in the experiment. A FORTRAN program was used to perform this analysis in finite elements of dx. Experiments were conducted using these methods and devices, as described in the Experimental section below (See Example 16).

C. Possible Modifications of Hemoglobin

No product currently under development can replace all the functions of blood. Instead, these blood product solutions are distinguished from other plasma expanders by their ability to increase the total oxygen that can be delivered. Of these, there are two general types: those that increase dissolved oxygen (i.e., perfluorocarbons) and those that carry oxygen chemically bound to hemoglobin (hemoglobin-based $O_2$ carriers). There are significant differences between the two types and they transport $O_2$ in fundamentally different ways.

Hemoglobin is a protein made up of 4 polypeptide subunits, 2 α and 2 β chains. One of each, tightly bound together, make up a half molecule (αβ dimer) and two dimers are more loosely bound to form the fully functional molecule ($\alpha_2\beta_2$ tetramer). The interface between the αβ dimers slides apart as $O_2$ is reversibly bound, forming two structures, one each corresponding to the fully deoxygenated (T, tense) and one to the fully oxygenated (R, relaxed) structure. These two conformers have vastly different affinities for $O_2$, so that as $O_2$ molecules are sequentially bound and the transition from deoxy to oxy occurs, the affinity for $O_2$ increases. This change in affinity is called "cooperativity" and is represented by the Hill coefficient, n (FIG. 13).

The loose interface between αβ dimers is of critical importance for hemoglobin-based blood substitutes. The equilibrium constant for this dissociation reaction is $10^{-6}$ M for $HbO_2$ which means that as hemoglobin concentration falls, the relative proportion of dimeric molecules increases. These dimers are very quickly and efficiently filtered in the glomerulus of the kidney. Mechanisms to remove dimers which are present when mild hemolysis occurs include haptoglobin binding which can remove free hemoglobin in concentrations up to 200 mg/dl. When this threshold is exceeded renal clearance of hemoglobin is very high, and renal toxicity may result.

Many chemical modifications of hemoglobin have been devised (See, Table 3). The purposes of these modifications are to prevent tetramer-dimer dissociation, modulate oxygen affinity, and prolong vascular retention. They take advantage of several reactive sites on the surface of hemoglobin, in its internal cavity and at the amino terminus. One of the most useful modifications for researchers (αα-hemoglobin, DCLHb™, HEMASSIST™, a hemoglobin solution for therapeutic and diagnostic purposes, trademark owned by Baxter International, Deerfield, Ill.) incorporates a single cross-link between a deoxyhemoglobin Lysine 99 residues with the reagent DBBF (Walder et al., J. Mol. Biol., 141: 195–216 [1980]). This single modification at once binds αβ dimers together and reduces the $O_2$ affinity of cell-free molecules to approximately that of intact human red blood cells. When crosslinking is carried out with oxygenated hemoglobin, the dimensions of the internal cavity change enough so that the reaction occurs between β82 Lysines. In this case, the final crosslinked product has a much higher $O_2$ affinity than that of the deoxy cross-linked product. This material can also be produced easily, but has been less well studied because its $O_2$ affinity has been traditionally thought to be too high to be physiologically or clinically useful.

TABLE 3

Examples Of Hemoglobin Modifications Useful In Preparation Of Blood Substitutes

| Reagent/Modification | Name | Reference |
|---|---|---|
| Amino acid modification: | | |
| N-carboxymethylation 4 amino termini | | DiDonato (1983) J. Biol. Chem., 258: 11890–11895 |
| monoisothiocyanate 4 amino termini | 2-, 3-, 4-ICBS | Currell (1994) Meth. Enzymol., 231: 281 |
| pyridoxal phosphate Val-1($\beta$) | PLP | Benesch (1982) J. Biol. Chem., 257: 1320–1324 |
| Cross-linked tetramers: | | |
| mono-(3,5-dibromosalicyl) fumarate | FMDA | Bucci (1989) J. Biol. Chem., 264: 6191–6195 |
| mono-(3,5-dibromosalicyl) muconate | | Rayzynska (1996) Arch. Biochem. Biophys., 325: 119–125 |
| bis(2,3-dibromo-salycyl) fumarate | | Bucci (1986) Biochim. Biophys. Acta 874: 76–81 |
| bis(3,5-dibromosalicyl) fumarate Lys-82($\beta_1$)-Lys-82($\beta_2$) Lys-99($\alpha_1$)-Lys-99($\alpha_2$) | DBBF $\beta\beta$-Hb $\alpha\alpha$-Hb, DCLHb (HemAssist) | Walder (1979) Biochem., 18: 4265–4270; and Chaterjee (1986) J. Biol. Chem., 261: 9929–9937 |
| bis-(3,5-dibromosalicyl) sebacate | | Bucci (1996) J. Lab. Clin. Med., 128: 146–153 |
| 2-nor-2-formylpyridoxal 5'-phosphate Lys-82($\beta_1$)-Val-1($\beta_2$) | NFPLP | Benesch (1981) Meth. Enzymol., 76: 147–158 |
| bis(pyridoxal) diphosphate Lys-82($\beta_1$)-Val-1($\beta_2$) | (bisPL)P2 | Benesch (1988) BBRC 156: 9–14 |
| bis(pyridoxal) tetraphosphate Lys-82($\beta_1$)-Val-1($\beta_2$) | (bisPL)P4 | Benesch (1994) Meth. Enzymol., 231: 267 |
| Diisothiocyanato benzene sulfonate Val-1($\alpha_1$)-Val-1($\alpha_2$) | DIBS ($\alpha$-DIBS-$\alpha$)$\beta$2 | Manning (1991) PNAS 88: 3329 |
| diisothiocyanate | | Kavanaugh (1988) Biochem., 27: 804 |
| Trimesoyl tris(methyl phosphate) Val-1($\beta_1$)-Lys-82($\beta_1$)-Lys-82($\beta_2$) Lys-82($\beta_1$)-Lys-82($\beta_2$) | Tm-Hb $\beta$82-Hb | Kluger (1992) Biochem., 31: 7551–7559 |
| Recombinant dialpha fusion wild type $\beta$N108K (Presbyterian) | rHb 0.1 (Optro) | Looker (1992) Nature 356: 258–260 |
| Polymers: | | |
| glycolaldehyde & carboxymethylation | | Fantl (1987) Biochem., 26: 5755–5761 |
| glycolaldehyde & PLP | | MacDonald (1991) Eur Pat 9,104,011.3 |
| glycolaldehyde & NFPLP | | MacDonald (1991) BACIB. 19: A424 |
| glycolaldehyde & DBBF | | MacDonald (1994) Meth. Enzymol., 231: 287–308 |
| glutaraldehyde Lysines, N-term Valines | (Hemopure), (Oxypure) | |
| glutaraldehyde & PLP Lysines, N-term Valines | PolyHeme SFH | DeVenuto (1982) Surg. Gyn. Obst., 155: 342–346 |
| glutaraldehyde & NFPLP Lysines, N-term Valines | polyHbNFPLP | Berbers (1991) J. Lab. Clin. Med., 117: 157–65 |
| glutaraldehyde & DBBF | | Nelson (1992) BACIB 20: 253–258 |
| Oxidative ring-opened raffinose Lysines, N-term Valines | (Hemolink) | Hsia (1989) U.S. Pat. No. 4,857,636 |
| Surface Conjugates: | | |
| cellulose | | Flemming (1973) Acta Biol. Med. Ger., 30: 177–182 |
| dextran dialdehyde | | Tam (1976) Proc. Natl. Acad. Sci., 73: 2118–2121 |
| dextran-alkylation Cys-93($\beta$) | Dx-Hb | Chang (1977) Can. J. Biochem., 55: 398–403 |
| dextran sulfate | SF-Dx | Barberousse (1986) J. Chromatogr., 369: 244–247 |
| dextran phosphate | P-Dx | Sacco (1990) Biochim. Biophys. Acta 1041: 279–284 |
| dextran benzene hexacarboxylate | Dx-BHC | Prouchayret (1992) BACIB 20: 319–322 |

TABLE 3-continued

Examples Of Hemoglobin Modifications Useful In
Preparation Of Blood Substitutes

| Reagent/Modification | Name | Reference |
|---|---|---|
| hydroxyethyl starch | | Cerny (1984) Appl. Biochem. Biotech., 10: 151–153 |
| inulin | | Iwasaki (1983) BBRC 113: 513–518 |
| polyvinylpyrrolidone | | Schmidt (1979) Klin. Wochenschr. 57: 1169–1175 |
| polyethylene glycol | | Ajisaka (1980) BBRC 97: 1076–1081 |
| methoxy-polyoxyethylene (mPEG) 10–12 Lysines | (PEG-Hb) | Zalipsky (1991) Polymeric Drugs, pp 91–100 |
| α-carboxymethyl, ω-carboxymethoxypolyoxyethylene (dicarboxyPEG) 8–10 Lysine & PLP | (PHP) | Iwashita (1995) Artificial Red Cells, pp 151–176 |

Another unique class of crosslinkers, trimesic acid derivatives, result in 2- or 3-point reactions (Kluger et al., Biochem., 31:7551–7559 [1992]). In early reports, the resulting modified hemoglobins produced with these appeared to be stable and the reaction seemed to have a high degree of specificity.

A variation on this 64,000 kD molecular weight hemoglobin is the genetically produced "rHb1.1" (Looker et al., Nature 356:258–260 [1992]) in which crosslinking is done genetically. In this case, 2 α chain genes are introduced into the *E. coli* genome such that when they are transcribed, a single gene product results in which one α chain is contiguous with the other (dialpha peptide). Thus, the product has a molecular weight of 64,000 kD and does not dissociate in to dimers. Its physiological properties are similar to αα-hemoglobin.

Other crosslinking agents are analogs of 2,3-DPG. NFPLP, a prototype of such a crosslinker, binds in the 2,3-DPG "pocket" between β chains and has the dual effects of preventing dimerization and reducing $O_2$ affinity. This product has been extensively studied (Bleeker et al., Biomater. Artific. Cells Immobil. Biotechnol., 20:747–750 [1992]) but unfortunately the crosslinker itself is difficult to synthesize, and scaleup has not been achieved practically.

Conjugated hemoglobins are those to which some modifying molecule has been attached to the surface (See e.g., Nho et al., Biomat. Artif. Cells Immobil. Biotechnol., 20:511–524 [1992]). Modifying groups include polyethylene glycol (PEG), polyoxyethylene (POE), or dextran. These products have increased molecular weights, depending on the number and size of the modifying groups, but are relatively easy to produce. Increasing the molecular size may also increase the hydration shell around the protein molecule, in the case of POE and PEG, and may thereby restrict the reaction of hemoglobin with other molecules in the cell-free environment.

Finally, nonspecific reagents can react with any of the 44 the ϵ-amino lysine groups on the surface of hemoglobin or the 4 amino-terminal groups. Such bifunctional reactants include glutaraldehyde and o-raffinose and have been used in at least three of the products presently in clinical trials. While the modification reactions are clearly understood chemically, the extent of reaction can sometimes be difficult to control, and a range of molecular weights of product may result (Marini et al., Biopolymers 29:871–882 [1990]).

The present invention provides methods to improve the current hemoglobin-based red cell substitutes which have serious problems. In general, molecular size can be increased by polymerization of hemoglobin with polyfunctional cross-linkers or by surface conjugation to polymers such as PEG, dextran, or other starches, carbohydrates, or proteins. Viscosity can be increased by conjugation to PEG or its analogues. The viscosity of the solution can be increased by formulation with a high viscosity material such as pentastarch, dextrans, carbohydrates or proteins which are, themselves, viscous. Finally, oxygen affinity can be increased by intramolecular crosslinking of hemoglobin in the R conformational state. This can be achieved by placing the hemoglobin in an environment such as $O_2$, CO or other ligand which favors the R conformation. Examples of specific changes to the production of modified hemoglobins to be used as cell-free oxygen carriers include the following.

1. αα-Hemoglobin

This hemoglobin, initially designed as a model compound for study by the U.S. Army, has been produced by Baxter Healthcare and is being tested as a replacement for human blood in the immediate postoperative period and in selected trauma patients. Both the Army and Baxter have reported that this product produces significant elevations of blood pressure and vascular resistance, and preclinical animal studies have shown that these undesirable properties eliminate any advantage to be derived from administration of hemoglobin solution (See e.g., Hess et al., J. Appl. Physiol., 74:1769–1778 [1993]).

As presently formulated, αα-Hb has low viscosity (approximately 1 cP, shear rate of 160 $s^{-1}$, 37° C.), high [Hb] at approximately 10 g/dl, a molecular size that is the same as that of tetrameric hemoglobin, and it has oxygen affinity similar to or lower than that of blood. The present invention provides αα-hemoglobin for which the viscosity has been increased by formulation in pentastarch or any high viscosity colloid. Indeed, the viscosity and molecular size can be increased by surface conjugation with PEG or any other suitable methods of surface decoration. In addition, the composition can be formulated with a lower [Hb]. In addition, its oxygen affinity can be increased by carrying out crosslinking chemistry using DBBF with the starting hemoglobin material in a (e.g., CO or $O_2$ liganded) high-affinity conformational state.

Thus, the present invention provides methods to improve this composition by reducing its P50, for example by crosslinking the hemoglobin in a liganded (e.g., CO or $O_2$) state, and by increasing its molecular size by surface decoration with PEG or other materials that increase its molecular radius and viscosity. Diffusion of $O_2$ in a solution of αα-hemoglobin could be reduced by formulation in pentastarch.

2. rHb1.1

Recombinant hemoglobin (e.g., OPTRO™, a recombinant human hemoglobin, trademark owned by Somatogen, Inc., Boulder, Colo.) may be produced using various hosts (e.g., bacteria). Currently available recombinant hemoglobin consists, primarily, of fused α chains and the introduction of a mutation (Presbyterian) which reduces its oxygen affinity. The present invention provides methods to improve this product by reducing its P50, for example, by eliminating the Presbyterian mutation or by introducing other mutations that increase its oxygen affinity or reduce cooperativity, and by increasing its molecular size by surface decoration with PEG or other materials that increase its molecular radius and viscosity. Diffusion of $O_2$ in a solution of OPTRO™ could be reduced by formulation in pentastarch.

As presently formulated, rHb1.1 has low viscosity, its molecular size is that of tetrameric hemoglobin, and it has an oxygen affinity similar to or lower than that of blood. The present invention provides methods to increase the viscosity of rHb1.1, by formulation in pentastarch or any high viscosity colloid. In addition, its viscosity and molecular size can be increased by surface conjugation using surface conjugation with PEG or any other suitable methods of surface decoration. Furthermore, it can be formulated with a low [Hb].

3. PHP (Pyridoxylated Hemoglobin Polyoxyethylene)

PHP (pyridoxylated hemoglobin polyoxyethylene; e.g., Apex Bioscience). This hemoglobin is from a human source, reacted with pyridoxal phosphate (PLP) to increase its P50, and then surface modified with a form of polyethylene glycol. The present invention provides methods to improve this product by eliminating the PLP reaction, crosslinking the liganded (e.g., CO or $O_2$) state, and by more extensive surface decoration with PEG, either by increasing the number of PEG strands per molecule or by increasing the length of individual PEG strands. Diffusion of $O_2$ in a solution of PHP could be reduced by formulation in pentastarch.

As presently formulated, PHP has an intermediate viscosity of approximately 2 cP (under conditions described herein), high [Hb] at approximately 8 g/dl, its molecular size is slightly more than 2-fold larger than a hemoglobin tetramer, and an oxygen affinity that is slightly greater than that of blood. The present invention provides methods to increase the viscosity of this product by formulation in pentastarch or any high viscosity colloid. Its viscosity and molecular size can be increased by more extensive surface decoration with PEG, either by increasing the number of PEG strands per molecule or by increasing the length of individual PEG strands. It can also be formulated at lower [Hb], and/or its oxygen affinity increased, by eliminating PLP during hemoglobin modification reaction.

4. HEMOLINK®

HEMOLINK® (Hemosol, Ltd.) (blood substitutes, namely, oxygen transporting fluids for administration to living human bodies for medical purposes, trademark owned by Hemosol, Inc., Ontario Canada), is a human-derived hemoglobin product with a very high P50, and is polymerized with o-raffinose, a multifunctional crosslinking reagent. The present invention provides methods to improve the product by crosslinking the liganded (e.g., CO or $O_2$) protein and by increasing its molecular radius and viscosity. This could be accomplished by surface decoration with any PEG derivative or conjugation to a polysaccharide or other polymer that would increase its molecular size. Diffusion of $O_2$ in a solution of HEMOLINK® could be reduced by formulation in pentastarch.

As presently formulated, HEMOLINK® has low viscosity (ca. 1.4 cP under conditions of our measurement), high [Hb] at approximately 10 g/dl, its molecular size is about 1.7-fold greater than tetrameric hemoglobin, and it has low oxygen affinity compared to blood. The present invention provides methods to increase the viscosity by formulation in pentastarch or any high viscosity colloid. Its viscosity and molecular size can be increased by surface conjugation using surface conjugation with PEG or other methods of surface decoration. In addition, it can be formulated at lower [Hb]. Its oxygen affinity can be increased by carrying out its polymerization chemistry using o-raffinose with the starting hemoglobin material in a (e.g., CO or $O_2$ liganded) high-affinity conformational state.

5. HEMOPURE®

HEMOPURE® (Bio-Pure) (blood substitutes for human and veterinary use, trademark owned by Biopure, Inc., Cambridge, Mass.) is a bovine-derived hemoglobin product with a moderately high P50, and is polymerized with glutaraldehyde, a bifunctional crosslinking reagent. The present invention provides methods to improve the product by crosslinking the liganded (e.g., CO or $O_2$) protein and by increasing its molecular radius and viscosity. This could be accomplished by surface decoration with any PEG derivative or conjugation to a polysaccharide or other polymer that would increase its molecular size. Diffusion of $O_2$ in a solution of HEMOPURE® could be reduced by formulation in pentastarch.

6. POLYHEME®

POLYHEME® (Northfield Laboratories) (hemoglobin solution) is a human-derived hemoglobin product with a moderately high P50 due to reaction with PLP, and is polymerized with glutaraldehyde, a bifunctional crosslinking reagent. The present invention provides methods to improve the product by crosslinking the liganded (e.g., CO or $O_2$) protein, eliminating the PLP and by increasing its molecular radius and viscosity. This could be accomplished by surface decoration with any PEG derivative or conjugation to a polysaccharide or other polymer that would increase its molecular size. Diffusion of $O_2$ in a solution of POLYHEME® could be reduced by formulation in pentastarch.

As presently formulated, POLYHEME® has high [Hb] at approximately 10 g/dl, its molecular size is larger than that of tetrameric hemoglobin by being polymerized, and its oxygen affinity is lowered by reaction with PLP. The present invention provides methods to increase the viscosity by formulation in pentastarch or any high viscosity colloid. Its viscosity and molecular size can be increased by surface conjugation using surface conjugation with PEG or other methods of surface decoration. It can also be formulated at lower [Hb]. Its oxygen affinity can be increased by carrying out its polymerization chemistry using glutaraldehyde in the absence of PLP and with the starting hemoglobin material in a (e.g., CO or $O_2$ liganded) high-affinity conformational state.

7. PEG-Hb

Commercially available PEG-Hb compositions (e.g., Enzon) may be improved using the present invention by decreasing its concentration and by formulation in pentastarch. Enzon's hemoglobin consists of a bovine hemoglobin modified by conjugation to linear 5000 MW polyethylene glycol (PEG) chains. Polyalkylene oxide (PAO) is a generic term for a group of molecules that includes PEG.

Attachment of PAO to hemoglobin is achieved by formation of a covalent bond between the PAO and the ε-amino groups of lysine residues. Enzon's hemoglobin is conjugated to 10–12 PAO chains per hemoglobin tetramer. When measured at a shear rate of 160 s$^{-1}$, 37° C., a 5 g/dl solution of Enzon's PEG-Hb exhibits a viscosity of 3.39 cP.

As presently formulated, PEG-Hb has a viscosity of approximately 3.5 cp (under conditions of described herein) at a [Hb] of 5.5 g/dl, its molecular size is 4-fold greater than that of tetrameric hemoglobin, and it has high oxygen affinity relative to blood. The present invention provides methods to increase the viscosity of this product at lower [Hb] by formulation in pentastarch or any high viscosity colloid. Furthermore, its viscosity and molecular size can be increased by more extensive surface decoration with PEG, either by increasing the number of PEG strands per molecule or by increasing the length of individual PEG strands. It can also be formulated at lower [Hb].

Additional methods to increase the viscosity (η, cP) unit per unit concentration ([Hb], g/dl) of a hemoglobin solution include, but are not limited to the following:

1. Increase the Number of Sites Conjugated to 5000 MW PAO Per Hemoglobin Tetramer Human hemoglobin contains 44 lysine residues (11 on each chain). In combination with the 4 N-terminal amino groups, this gives 48 theoretically possible sites for covalent attachment of PAO using the chemistry described for modification of amino groups. Additional chemistry has been described (See e.g., Acharya's U.S. Pat. No. 5,585,484; herein incorporated by reference) that allows covalent attachment of PAO to the sulfhydryl group of a cysteine residue. There are 6 cysteine residues per Hb tetramer (i.e., one on each α chain, and two on each β chain) increasing the number of theoretically possible attachments to 54. Further PAO modifications are contemplated, including the use of suitable conjugation chemistry lead to attachment to serine, threonine, tyrosine, asparagine, glutamine, arginine, and histidine residues. It is also contemplated that chemistry that allows conjugation to carboxylic acid groups may allow PAO conjugation to aspartic acid and glutamic acid residues as well as the C-terminal carboxy groups of hemoglobin.

If the number of conjugation sites per tetramer is sufficiently large, it is contemplated that PAO molecules of lower molecular mass (i.e., MW<5000) will still achieve an increased viscosity per unit concentration over Enzon's product without the modifications described herein.

2. Maintain the Number of Covalent PAO Attachments and Increase the Size of Each PAO Moiety An increased viscosity per unit hemoglobin concentration is contemplated in situations in which the PAO groups attached to the 10–12 sites per tetramer are of greater molecular mass (i.e., MW>5000). This can be achieved by using PAO starting material consisting of molecules containing longer and/or branched PAO chains.

If the molecular size of the PAO units is sufficiently large, it may be possible to modify a fewer number of sites on the tetramer (i.e., <10) and still achieve an increased viscosity per unit concentration over Enzon's product.

III. The Oxygen-Carrying Compentent of the Blood Products of the Present Invention In preferred embodiments of the present invention, the oxygen-carrying component is native or modified hemoglobin (e.g., a HBOC). Modified hemoglobin is altered by chemical reaction (e.g., cross-linking or polymerization) or through the addition of adducts (e.g., polyethyleneglycol, polyoxyethylene). Furthermore, the oxygen-carrying component of the present invention may be recombinantly-produced hemoglobin or a hemoglobin product encapsulated in a liposome. The present invention also contemplates the use of other means for oxygen delivery that do not entail hemoglobin or modified hemoglobin.

Though the present invention contemplates the use of any oxygen-carrying component, preferred oxygen-carrying components entail solutions of human or animal (e.g., bovine) hemoglobin, intramolecularly crosslinked to prevent dissociation into dimeric form. Optionally, the preferred oxygen-carrying components of the present invention may be oligomerized to oligomers of molecular weight up to about 750,000 daltons, preferably up to about 500,000 daltons. Hemoglobin preparations prepared by genetic engineering and recombinant processes are also among the preferred oxygen-carrying components.

The preferred oxygen-carrying components of the present invention should be stroma free and endotoxin free. Representative examples of preferred oxygen-carrying components are disclosed in a number of issued United States Patents, including U.S. Pat. No. 4,857,636 to Hsia; U.S. Pat. No. 4,600,531 to Walder, U.S. Pat. No. 4,061,736 to Morris et al.; U.S. Pat. No. 3,925,344 to Mazur; U.S. Pat. No. 4,529,719 to Tye; U.S. Pat. No. 4,473,496 to Scannon; U.S. Pat. No. 4,584,130 to Bocci et al.; U.S. Pat. No. 5,250,665 to Kluger et al.; U.S. Pat. No. 5,028,588 to Hoffman et al.; and U.S. Pat. Nos. 4,826,811 and 5,194,590 to Sehgal et al.; the contents of each are hereby incorporated by reference. In a more preferred embodiment, the oxygen-carrying components comprise human, recombinant, or animal hemoglobin, either cross-linked or not, modified by reaction with polyethyleneglycol (PEG) or polyoxyethylene (POE).

The capacity of a solution to deliver oxygen to tissues can be determined in a number of ways routinely used by researchers, including direct measurement of oxygen tension in tissues, increased mixed venous oxygen tension, and reduced oxygen extraction ratio.

IV. The Non-Oxygen-Carrying Component of the Blood Products of the Present Invention As noted above, the present invention contemplates a mixture comprising an oxygen-carrying component and a non-oxygen-carrying component. The non-oxygen-carrying component of the present invention is any substance used for temporary replacement of RBCs which has oncotic pressure (e.g., dextran-70, dextran-90, hespan, pentastarch, hetastarch, albumin, or any other colloidal intravenous solution).

Non-oxygen-carrying plasma expander products for the treatment of hypovolemia and other conditions are commercially available; representative products include, but are not limited to, PENTASPAN® (DuPont Merck, Fresenius) (a cardiovascular pharmaceutical, namely, and adjunct to leukopheresis to increase leukocyte yields and also used for volume expansion and hemodilution, trademark owned by DuPont Merck, Wilmington, Del.), HESPAN® (plasma volume expander) (6% hetastarch in 0.9% sodium chloride for injection; DuPont Merck), and MACRODEX® (blood plasma expander comprising as the active ingredient a special fraction of the macromolecular polysaccharide dextran, trademark owned by Northfield Laboratories, Evanston, Ill.) (6% Dextran 70 in 5% dextrose in water for injection, or 6% Dextran 70 in 0.9% sodium chloride for injection; Pharmacia). Non-oxygen-carrying fluids available for clinical use (e.g., hemodilution or resuscitation) can be broadly classified as crystalloid solutions (i.e., salt solutions) and colloid solutions. In preferred embodiments of the present invention, colloid solutions comprise the non-oxygen-carrying component of the mixture.

In one embodiment of the present invention, the problems of the prior art products are alleviated by the formulation and use of a composition (an aqueous solution) that contains both an oxygen-carrying component (e.g., a HBOC) and a non-oxygen-carrying component comprising an inert, non-proteinaceous colloid. Such compositions result in two effects, either alone or in combination. First, the oxygen carrying capacity of the composition is decreased, while colloid osmotic (oncotic) pressure and plasma retention are maintained. The resulting colloid-diluted oxygen-carrying component has fewer oxygen-delivering colloidal particles per unit volume than the oxygen-carrying component alone, and hence there is less oxygen presented to the arterial walls. That is, the oxygen delivery more closely approximates that of whole blood, so that the combination according to the invention is able to deliver and distribute its oxygen loading in a manner more closely resembling that achieved by RBCs.

Second, by proper choice of type and amount of non-proteinaceous colloid (discussed below), the viscosity of an oxygen-carrying component-colloid composition can be increased, preferably close to that of whole blood. This also appears to reduce or counteract arterial wall reaction. Though an understanding of the mechanism of this effect is not required in order to practice the present invention, it is believed to be due to i) reduced oxygen delivery as a result of decreased hemoglobin and ii) increased shear stress at the vessel wall (which results in the increased release of endogenous vasodilators such as prostacyclin).

Suitable examples of non-proteinaceous colloids for use in the compositions of the present invention include dextran and pharmaceutically-acceptable derivatives thereof, starch and pharmaceutically acceptable derivatives thereof, and polyvinylpyrrolidone (PVP). Particularly preferred among suitable non-proteinaceous colloids is pentastarch. Indeed, suitable non-proteinaceous colloids include substantially all non-proteinaceous colloidal substances which have previously been successfully used as hemodiluents. Acceptable candidates should be water soluble, exhibit oncotic pressure, and be biologically inert and otherwise pharmaceutically acceptable. The cost of these materials (e.g., oncotic non-proteinaceous colloids like dextran and hetastarch), on a weight for weight basis, is much lower than that of hemoglobin and HBOCs.

V. Clinical and Other Applications of the Present Invention

The present invention finds use in many settings, ranging from the emergency room to the operating table, as well as military conflicts, and veterinary applications. This versatility is due to the optimized formulations of the present invention, which may be stored as desired, and avoid the necessity for cross-matching or other laboratory tests to determine compatibility with the patient to be treated. Extensive research on chemical and genetic modifications of hemoglobin, in conjunction with the present invention now permit the design of molecules with nearly any desired combination of physical and physiological properties in a heretofore unexpected and highly efficient manner.

A. Clinical Applications

Various clinical applications are matched with properties of the proposed red cell substitutes in Table 4, below. In this Table, $T_{1/2}$ refers to the half-life.

TABLE 4

Potential Clinical Applications For Red Cell Substitutes And Optimal Properties

| Application | COP | P50 | Viscosity | $T_{1/2}$ |
|---|---|---|---|---|
| Hemodilution | ↑ | ↓ | ↑ | ↑ |
| Trauma | ↑ | ↓ | ↑ | ↑ |
| Septic Shock | ↑ | ↓ | ↑ | ↑ |
| Ischemia (e.g., stroke) | ↑ | ↓ | ? | ↓ |
| Cancer | — | ↓ | ↓ | ↑ |
| Chronic Anemia | — | ↓ | ↑ | ↑ |
| Sickle Cell Anemia | ↑ | ↑ | ↓ | ↑ |
| Cardioplegia | ↑ | ↑ | ↓ | — |
| Hypoxia | — | ↓ | ↑ | ↑ |
| Organ Perfusion | — | ↑ | ? | — |
| Cell Culture | — | — | — | — |
| Hematopoiesis | ↓ | ↑ | ↓ | ↓ |

It is contemplated that high oncotic activity (COP) will find use in the short term, immediate, resuscitation from hypovolemic shock. The utility of hypertonic saline/dextran (HSD) has been shown in animal studies (Kramer et al., Surgery, 100(2):239–47 [1986]). Oncotic activity (COP) expands the vascular volume very quickly and it is contemplated that perhaps this, combined with the rapid restoration of $O_2$ capacity, might lead to significantly better salvage of patients and tissues after acute blood loss. However, there numerous settings in which the compositions and methods of the present invention find use including the following:

Hemodilution. In this clinical application, the patient comes to surgery and some volume of blood is removed, to be replaced with the substitute. The goal is preventative, not to correct some imbalance. A solution that performs very close to blood is needed. A slightly increased COP is desired because it increases blood volume and cardiac output, in anticipation of surgical blood loss. Since the replacement fluid is hemoglobin-based, a reduced P50 is preferred, in order to overcome facilitated diffusion. Viscosity should be increased for the same reason, and the $T_{1/2}$ should be prolonged to eliminate or reduce the need for postoperative transfusion with allogeneic blood units, should the ones collected prior to surgery (autologous) not be sufficient. The solution for hemodilution would have the same properties as one used in cardiopulmonary bypass.

Trauma. In trauma, the patient has lost whole blood. In response to this blood loss, fluid shifts from the interstitial and intracellular spaces to attempt to replace lost volume. In the process, hematocrit and viscosity fall and vasoconstriction occurs to shunt blood from organs that have low priority. These include the skin and gut, for example, while blood flow to the kidneys, heart and brain are preserved for as long as possible. The goal of a therapeutic blood replacement here would be to first replace lost volume as fast as possible. Hence, increased COP are desired. Since the replacement fluid is hemoglobin-based, a reduced P50 is preferred, in order to overcome facilitated diffusion. The viscosity should be increased for the same reason.

Septic Shock. In overwhelming sepsis, some patients may become hypertensive in spite of massive fluid therapy and treatment with vasoconstrictor drugs. The mechanism of lowered blood pressure in this instance is overproduction of nitric oxide (NO). Therefore hemoglobin is close to an ideal agent to treat these patients with because of the avidity with which hemoglobin binds NO. In general, NO binding affinity parallels $O_2$ binding affinity, so an agent for use in this application should have very high $O_2$ affinity (low P50). Since the patients are often fluid overloaded, increased COP would be desired, but not essential, and increased viscosity would reduce autoregulatory vasoconstriction. The $T_{1/2}$ should be moderately long, but it is not necessary to be markedly prolonged, since continuous infusions can be used in these patients.

Ischemia (e.g., stroke). Ischemia refers to the condition where tissue is "starved" for oxygen. This usually results from limitation of blood flow as in, for example, a heart attack or cerebrovascular accident. The tissue, starved of $O_2$ dies in small patches, called "infarcts." The goal of blood replacement therapy here would be to increase blood flow and to promote $O_2$ delivery into capillary beds. Hence, a solution of lower viscosity may be preferred, in order to better perfuse capillary beds. This can be done only if the blood volume is maintained or expanded, and therefore an increased COP would be desirable. In most situations of heart attack and stroke, the tissue damage is acute, so therapy is only necessary for a few hours. Thus, the $T_{1/2}$ is less important than in other applications.

Cancer. To increase the radiosensitivity (or sensitivity to chemotherapy), the goal is to deliver as much $O_2$ to the hypoxic core of the tumor as possible. The microcirculation of tumors is unlike that of other tissues, because it lacks endothelial lining of capillaries, and normal vasoactivity does not occur. Thus, it should be possible to provide solutions of low viscosity. The P50 should be very low so that little, if any, $O_2$ is unloaded in tissues before it reaches the hypoxic core of the tumor. In other words, we would like $O_2$ to be unloaded at very low $PO_2$, if possible Plasma $T_{1/2}$ can be as long as possible, so that repeated doses of irradiation or chemotherapy can be administered.

Chronic anemia. These patients are unable to regenerate lost red cells or they are not able to keep production up with normal (or accelerated) destruction. In this situation, it is desired that the transfusion substitute to behave as much as possible like native red cells. Thus, facilitated diffusion should be overcome by increasing oxygen affinity and viscosity. In this application, more than any other, the $T_{1/2}$ is very important because patients will be unable to replace lost or metabolized hemoglobin on their own.

Sickle cell anemia. This is a unique clinical condition in that red cell turnover is very high, and the sickling process in the affected person's red cells is a function of $PO_2$. That is, the lower the $PO_2$, the greater the sickling rate. Sickling is also a function of red cell density and viscosity, which, in turn, is strongly dependent on hematocrit. The ideal solution in a sickle cell crisis would be one that delivers $O_2$ to sickled red cells. Thus, it may be preferable to use a high, rather than low, P50 so there is a net transfer of $O_2$ in favor of the sickled red cells. In order to do this, it would be necessary to decease diffusion in any way possible, to reduce vasoactivity which could offset any potential benefit of oxygenating the red cells. At the same time, it is preferred that the solution to have good flow properties. Thus, a balance between P50 and viscosity would have to be struck such that red cells are oxygenated while vasoconstriction is blocked or, at least, not induced.

Cardioplegia. In certain cardiac surgical procedures, the heart is stopped by appropriate electrolyte solutions and reducing the temperature of the patient. Reduction of the temperature will reduce P50 drastically, possibly to the point where $O_2$ may not be unloaded under any ordinary physiological conditions. Thus, the P50 of a solution for this purpose might be higher than for other applications. The viscosity is also temperature-dependent and appropriate adjustments would be made such that the in vivo viscosity is close to that of blood under the specific conditions of the patient.

Hypoxia. In altitude dwellers and world-class athletes and soldiers under extreme conditions, extraction of $O_2$ from air in the lung may become limiting to overall $O_2$ transport. This aspect of $O_2$ transport would probably be more important than the ability of the solution to unload $O_2$ in tissues. In this case, lower P50 would be advantageous, and cooperativity should be maximal. Vasoactivity would not be desired, so viscosity would be elevated. The COP of such solutions would not need to be elevated, and the plasma $T_{1/2}$, should be as long as possible.

Organ Perfusion. Here, the main goal is to increase $O_2$ content of the perfusate. The parameters of $O_2$ loading and unloading are less important than in other conditions, since the fluid is not flowing. Therefore, nearly complete extraction is possible. P50 can be relatively normal or even elevated, since the solutions can be oxygenated with external oxygenators.

Cell Culture. This requirement is almost identical to that of organ perfusion, except that the rate of $O_2$ consumption may be higher, depending on the cells and their concentration.

Hematopoiesis. Here, the hemoglobin is serving as a source of heme and iron, to be resynthesized into new hemoglobin. Thus, the hemoglobin should be taken up into the monocyte-macrophage system and broken down in such a way as to make its components available for red cell metabolism and maturation. The properties of COP, P50 and viscosity can be the same as the hemodilution solution. The $T_{1/2}$ can be relatively short, as long as metabolism is efficient.

Many workers in the field of oxygen transport have assumed that oxygen affinity of modified hemoglobin should be low, or at least not significantly different from that of red cells, in order to maximize tissue oxygenation. During the development of the present invention, it was found that this concept is invalid. In severe hypoxia, pulmonary $O_2$ diffusion may become limiting to $O_2$ uptake in the alveolus, as demonstrated in mountaineers at extreme altitude (Winslow et al., [1984]). In this instance, increased, rather than decreased $O_2$ affinity is beneficial because it increases arterial $O_2$ saturation. Based on the high altitude data, this point is reached at approximately 6,000 meters altitude, or at a $PaO_2$ of about 40 Torr. By extrapolation, one might conclude that sea level patients with severe restrictions in diffusive pulmonary $O_2$ uptake might also benefit from increased hemoglobin $O_2$ affinity. If the pulmonary capillary $PO_2$ reaches a maximal value of 40 Torr (or less), then shifting the oxygen equilibrium curve to the left will increase saturation, in effect providing the same increase in $O_2$ content as a transfusion, without adding the burden of increased red cell mass and, hence, viscosity.

In general, plasma retention times should be as long as possible. However, it is also contemplated that perhaps for $O_2$ delivery to specific tissues (e.g., tumors, myocardium, ulcers, sickle cell disease) this property might not be so important. Furthermore, if the reason to give a hemoglobin solution is to stimulate erythropoiesis, it is contemplated that a short retention time is desired.

The present invention provides data that show if the properties of viscosity, oncotic pressure, oxygen affinity and hemoglobin concentration are optimized as described, the hemoglobin can be formulated with additional components to serve additional functions of blood. For example, coagulation factors (e.g., Factors VIII, IX, and/or II), immunoglobulins, antioxidants, iron chelators, peroxidases, catalase, superoxide dismutase, carbonic anhydrase, and other enzymes may be mixed with the hemoglobin solution in order to provide benefit to patients in need of such compositions. Similarly, drugs such as cytotoxins, antibiotics or other agents may be mixed with the solution or chemically conjugated to other components, such as hemoglobin or other polymers.

In addition, the final product can be formulated at any desired electrolyte and salt composition. It can be stored in the liquid state, frozen or lyophilized as the final product or the hemoglobin component itself can reconstituted with any solution subsequently. Such reconstitution medium could be, but need not be limited to, saltine, Ringer's lactate, albumin solution, or PlasmaLyte, for example. The final product can be stored in any biocompatible container such as glass or plastic.

B. Veterinary Applications

The present invention is not limited to use in humans. In addition to the clinical applications briefly described above, the present invention finds utility in the veterinary arena. The compositions of the present invention may be used with domestic animals such as livestock and companion animals (e.g., dogs, cats, birds, reptiles), as well as animals in aquaria, zoos, oceanaria, and other facilities that house animals. For example, as with humans, the compositions of the present invention may be used for emergency treatment of domestic and wild animals traumatized by blood loss due to injury, hemolytic anemias, etc. For example, it is contemplated that embodiments of the present invention in such as equine infectious anemia, feline infectious anemia, hemolytic anemias due to chemicals and other physical agents, bacterial infection, Factor IV fragmentation, hyperspienation and splenomegaly, hemorrhagic syndrome in poultry, hypoplastic anemia, aplastic anemia, idiopathic immune hemolytic conditions, iron deficiency, isoimmune hemolytic anemia, microangiopathic hemolytic, parasitism, etc.). In particular, the present invention finds use in areas where blood donors for animals of rare and/or exotic species are difficult to find.

VI. Blood Product Compositions

The relative proportions of the oxygen-carrying component and the non-oxygen-carrying component (e.g., a colloid plasma expander) included in the compositions of the present invention can vary over wide ranges. Of course, the relative proportions are, to some extent, dependent upon the nature of the particular components, such as the molecular weight of the colloid used as a non-oxygen-carrying plasma expander. However, the present invention is not limited to the use of colloids as the non-oxygen-carrying component.

In preferred embodiments of the present invention, the hemodilution effect of the non-oxygen-carrying component (e.g., a non-proteinaceous colloid) predominates, i.e., the overall oxygen-carrying capacity of the oxygen-carrying component is reduced by dilution so that the adverse effects of excessive oxygen release at the arterial walls are alleviated. In such embodiments, substantial economic benefits are derived from a composition that preferably contains at least 20% by weight of each of the components, and more preferably at least 25% by weight of each component. Most preferable compositions comprise from approximately 30 to approximately 70 parts of the oxygen-carrying component (e.g., HBOC), correspondingly, from approximately 70 to approximately 30 parts of the non-oxygen carrying component (e.g., inert colloid) (per 100 parts by weight of the combination of the two).

In preferred embodiments, the viscosity of the blood substitute compositions of the present invention is preferably close to that of normal blood. Thus, when it is desirable to utilize a composition whose primary purpose is to increase viscosity, high molecular weight colloids in amounts of from approximately 1 to approximately 20 parts by weight per 100 parts by weight of oxygen-carrying component are preferred.

In other preferred embodiments of the present invention, increased viscosity (i.e., to a value approaching that of whole blood) of the composition is the predominant effect. In these compositions, the viscosity of the composition is high enough so that shear stresses at the arterial walls are sufficient to release endogenous vasodilators to counteract the effects of the plentiful oxygen availability at the arterial walls. In such embodiments, the non-oxygen carrying component (e.g., non-proteinaceous colloid) should have a substantially higher molecular weight than the oxygen carrying-component, but should be used in smaller amounts to avoid excessive viscosities. Polyvinylpyrrolidone (PVP) of molecular weight 300,000–750,000 used in amounts from about 1 to about 20 parts by weight per 100 parts by weight of oxygen-carrying component is particularly suitable in these embodiments. Similarly, high molecular weight starches (e.g., approximately 200,000–750,000 molecular weight) are also preferred in these embodiments. The amounts are chosen so as to result in an oxygen-carrying component—colloid solution having a viscosity, relative to whole blood (assigned a value of 1), of from about 0.5 to about 1.2.

In certain embodiments of the present invention, advantage is taken of both of the above-mentioned effects. That is, an amount and type of the non-oxygen-carrying component (e.g., non-proteinaceous inert colloid plasma expander) is chosen which both reduces the amount of oxygen carried by a unit volume of the solution, and increases its viscosity to a level approximating that of normal whole blood. For this purpose, PVP and starches of molecular weights higher than that of the oxygen—carrying component are used, and in amounts sufficient to increase the viscosity, to reduce the amount of oxygen carried, and to reduce the cost of the solution. Specifically, PVP and starches possessing molecular weights from about 200,000 to about 600,000 used in amounts from about 5 to about 50 parts by weight of inert colloid per 100 parts by weight of the oxygen-carrying component are contemplated for use with the present invention.

In some embodiments, the present invention contemplates that the concentration of the combined oxygen-carrying component and non-oxygen-carrying component (e.g., inert colloid plasma expander) in the aqueous solution compositions will generally be in the same range as that usually employed when one of the ingredients is used alone for the same purpose (i.e., from about 5 to about 15 grams of the combination per decaliter of solution).

The compositions of the present invention provide the following improvements over current blood substitutes: i) decreased concentration of hemoglobin to which the patient is exposed, thereby reducing the toxicity and cost of the blood product; ii) oncotic pressure, which more effectively expands the vascular volume than the currently used blood substitutes; iii) optimal viscosity which maintains capillary blood flow; iv) optimal oxygen affinity which reduces oversupply of oxygen to arteriolar walls; and v) optimal oxygen carrying capacity. All of these improvements increase the effectiveness of the blood products as a cell-free oxygen carrier.

Several prior art references discuss the possibility of mixing hemoglobin solutions with non-oxygen carrying plasma expanders. For example, U.S. Pat. No. 4,061,736 to Morris et al. and U.S. Pat. No. 4,001,401 to Bonson et al. describe pharmaceutical compositions comprising an analog of hemoglobin and a pharmaceutically acceptable carrier; the carrier may comprise, for example, polymeric plasma substitutes (e.g., polyethylene oxide). Similarly, U.S. Pat. No. 5,349,054 to Bonaventura et al. describes a pharmaceutical composition comprising a hemoglobin analog which can be mixed with a polymeric plasma substitute (e.g., polyvinylpyrrolidone). However, the prior art does not describe the specific compositions nor the techniques of the present invention for improving the effectiveness of a blood substitute and reducing the toxicity of those solutions.

DESCRIPTION OF SOME PREFERRED EMBODIMENTS

Generally speaking, compositions comprising i) an oxygen-carrying component (e.g., a HBOC) with high oncotic pressure, oxygen affinity and viscosity and ii) a non-oxygen-carrying component with similar oncotic pressure and viscosity provide an optimal blood product. In the most preferred embodiments of the present invention, the oxygen-carrying component of the mixture comprises a polyethylene glycol—modified hemoglobin and the non-oxygen-carrying component comprises pentastarch.

As described in more detail in the Experimental section, there are currently two commercially available hemoglobin products modified with polyethylene glycol. The first product, Pyridoxal Hemoglobin Polyoxyethylene (PHP), is a human-derived product from Apex Bioscience. The second product, PEG-Hb, is a bovine-based product obtained from Enzon, Inc. Though most of the experimental work was performed using PEG-Hb, the two PEG-modified hemoglobin products gave qualitatively the same results. It is to be understood that the preferred oxygen-carrying components of the present invention are not limited to PEG-Hb and PHP; indeed, any hemoglobin products associated with polyethylene glycol are contemplated for use with the most preferred mixtures of the present invention.

Pentastarch, the most preferred non-oxygen-carrying component of the present invention, is commercially available from DuPont Merck (PENTASPAN®) as well as from other sources. It comprises hydroxethyl starch and has a molecular weight of approximately 250,000 Daltons. Because of its lower molecular weight and lower degree of hydroxyethyl substitution compared to other starches (e.g., hetastarch), it exhibits higher oncotic pressure and faster enzymatic degradation in the circulation. As described in detail in the Experimental section, dilution of PEG-Hb with a different non-oxygen-carrying component like hetastarch reduces the resulting blood product's viscosity and oncotic pressure, and reduces the oxygen capacity of the resulting mixture. In contrast, the mixtures resulting from combination of PEG-modified hemoglobin with pentastarch have viscosity and oncotic pressure values very close to that of PEG-Hb alone, and have been shown to lead to enhanced animal survival and physiological parameters compared to other mixtures (see Experimental section).

Preferred mixtures of polyethylene glycol-modified hemoglobin and pentastarch contain at least 20% by weight of each of the components, and more preferably at least 25% by weight of each component. Most preferable compositions comprise from approximately 30 to approximately 70 parts of the oxygen-carrying component PEG-modified hemoglobin, and, correspondingly, from approximately 70 to approximately 30 parts of the non-oxygen carrying component pentastarch (per 100 parts by weight of the combination of the two).

The experimental results presented below indicate that a mixture of PEG-Hb and pentastarch performed similarly to a solution of PEG-Hb alone. This was true even though the hemoglobin concentration to which the animals were exposed and the amount of hemoglobin product used were less by half with the mixture, offering the advantage of reducing the concentration of hemoglobin given to patients, thereby reducing both cost and potential adverse effects.

As previously indicated, the compositions and methods of the present invention can be used in any situation in which banked blood is currently administered to patients. For example, the compositions can be administered to patients who have lost blood during surgery or due to traumatic injury. The compositions of the present invention are advantageous in that they save the patient exposure to possible infectious agents, such as human immunodeficiency virus and hepatitis virus.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); mM (millimolar); µM (micromolar); g (grams); mg (milligrams); fig (micrograms); kg (kilograms); L (liters); mL (milliliters); dL (deciliters); µL (microliters); cm (centimeters); mm (millimeters); µm (micrometers); nm (nanometers); min. (minutes); s and sec. (seconds); b.w. (body weight); i.p. (intraperitoneal or intraperitoneally); Da (Daltons); dP/dt (change in pressure over time); IU (international units); Hg (mercury); Hz (hertz); MHz (mega hertz); COP (colloid osmotic pressure); CRBCv (Capillary red blood cell velocity); FCD (functional capillary density); FDA (United States Food and Drug Administration); Hb (hemoglobin); MAP (mean arterial pressure); Pd (palladium); PEG (polyethylene glycol); PEGHb (bovine hemoglobin modified by conjugation with polyethylene glycol); sat. (saturation); sem and s.e.m. (standard error of the mean); TM (trimesic acid); Abbott (Abbott Laboratories, Chicago, Ill.); Beckman (Beckman Instruments, Fullerton, Calif.); Bectron (NJ); Dupont (Dupont Pharmaceuticals, Wilmington, Del.); EG&G Electro Optics (Salem, Mass.); Enzon, Inc., (Piscataway, N.J.); Fresenius (Walnut Creek, Calif.); Hemocue, Inc. (Mission Viejo, Calif.); Hemosol Inc. (Etobicoke, ON, Canada); IPM (IPM, Inc., San Diego, Calif.); Lexington Instruments (Waltham, Mass.); Pharmacia (Pharmacia, Inc., Piscataway, N.J.); Porphyrin Products, Inc. (Logan, Utah); Sharp (Japan); Sony (Japan); TCS Medical Products (Hintingdon Valley, Pa.); Tektronix (Tektronix Inc., Beaverton, Oreg.); Wescor (Logan, Utah).

The following general methods were used in the examples that follow unless otherwise indicated.

Animal Model and Preparation

Experiments (except those described in Example 16) were carried out with 10 Syrian golden hamsters of 40–50 g body weight. A "hamster window preparation" was then generated in each animal using a described surgical technique. (See, e.g., H. D. Papenfuss et al., "A transparent access chamber for the rat dorsal skin fold," Microvasc. Res. 18:311–318 [1979]; H. Kerger et al., "Systemic and subcutaneous microvascular oxygen tension in conscious Syrian golden hamsters," Am. J. Physiol., 267 (Heart. Circ. Physiol. 37): H802–810 [1995]). Briefly, each animal's dorsal skinfold, consisting of 2 layers of skin and muscle tissue, was fitted with two titanium frames with a 15 mm circular opening and surgically installed under pentobarbital anesthesia (50 mg/kg b.w., i.p., MEMBUTAL®, Abbott, an anesthetic). Layers of skin muscle were carefully separated from the subcutaneous tissue and removed until a thin monolayer of muscle and one layer of intact skin remained.

Thereafter, a cover glass held by one frame was placed on the exposed tissue, allowing intravital observation of the microvasculature. The second frame was open, exposing the intact skin. PE10 catheters were implanted in the jugular vein and the carotid artery. The catheters were passed subcutaneously from the ventral to the dorsal side of the neck, and exteriorized through the skin at the base of the chamber. The patency of the catheters was ensured by daily flushing of the implanted tip with 0.005–0.01 mL of heparinized-saline (40 IU/mL). Microvascular observations of the awake and unanesthetized hamster were performed at least two days after chamber implantation, thus mitigating post-surgical trauma. During these investigations, the animals were placed in a tube from which the window chamber protrudes to minimize animal movement without impeding respiration.

A preparation was considered suitable for experimentation if microscopic examination of the window chamber met the following criteria: i) no signs of bleeding and/or edema; ii) systemic mean blood pressure above 80 mm Hg; iii) heart rate above 320 beats/minute (Beckman recorder, R611, Spectramed transducer P23XL); iv) systemic hematocrit above 45% READACRIT® refrigerated microcentrifuge, Bectron, trademark owned by Becton Dickinson and Company, Franklin Lakes, N.J.); and v) number of immobilized leukocytes and leukocytes flowing with venular endothelial contact less than 10% of all passing leukocytes at time point control.

Unless otherwise indicated, the experiments described hereafter were carried out exclusively in the hamster window preparation. This model was selected because it allows observation of the microcirculation for prolonged periods (i.e., several days) in the absence of anesthesia; previously performed microvascular studies indicated that data obtained from anesthetized animals is not representative of the awake condition. The hamster window preparation also presents the tissue being observed in a state that is isolated from the environment in order to obtain representative data.

Intravital Microscopy

Microscopical observations were performed using an intravital microscope (Leitz, Ortholux II) with a 25×SW 0.60 n.a. water immersion objective. The preparation was observed visually with a 10×ocular at a total optical magnification of 250×. Contrast enhancement for the transilluminated image was accomplished by using a blue filter (420 nm), which selectively passes light in the maximum absorption band of hemoglobin, causing the red blood cells to appear as dark objects in an otherwise gray background. A heat filter was placed in the light path prior to the condenser.

The microscopic images were viewed by a closed circuit video system consisting of two different cameras, a video cassette recorder (Sharp XA-2500S) and a monitor (Sony, PVM 1271Q), where total final magnification at the monitor was 650×.

Capillary Red Blood Cell Velocity

Capillary red blood cell velocity (CRBCv) was measured using the video dual window technique with a velocity tracing correlator (IPM, model 102B). CRBCv for each capillary was measured for a period of 20 seconds in order to obtain an average velocity over the period of observation. All measurements were performed in the same capillaries. Those capillaries that had blood flow and which stopped at subsequent time points were not included in the statistics with a zero value at the time point in which there was no flow; this is because their effect on tissue perfusion index is accounted for by their effect on the functional capillary density (FCD), i.e., the number of capillaries in a unit area observed to be passing RBCs. CRBCv was measured in one-to-two vessels per field of observation (10–12 per animal), since not all capillaries in a field are in the same focal plane.

Arteriolar and Venular Diameters

Arteriolar and venular diameters were measured at each time point using an image shearing monitor (IPM, model 907) during video playback.

Measurement of $pO_2$ In Microcirculation

Before collection of data, each animal received a slow intravenous injection of palladium (Pd) -coproporphyrin (Porphyrin Products, Inc.) previously bound to albumin. The concentration used was 30 mg/kg body weight. During $pO_2$ measurements, a xenon strobe arc (EG&G Electro Optics) with a decay constant of 10 microseconds was flashed at 30 Hz over a selected area. Epi-illumination was only used during $pO_2$ measurements, in order to avoid possible tissue damage which may be caused by the intense illumination. The phosphorescence emission from the epi-illuminated area passes through an adjustable slit and a long band pass filter (cut off at 630 nm) before being captured by a photomultiplier (EMI, 9855B). Slit size was usually kept at 15×100 µm (relative to the actual microscopic field), and it was always positioned along the length of the vessel.

When interstitial measurements were performed, the slit was positioned parallel to the nearest vessel, at various distances. The signals from the photomultiplier were sent to a digital oscilloscope (Tektronix, 2430). The oscilloscope averages 200–500 curves, and a single smoothed curve was then digitized (10 bit resolution) at a rate of 0.5 MHz and stored for later analysis. Each curve was also processed by a specialized analog processor for the calculation of $pO_2$.

General Experimental Protocol

Unless otherwise indicated below, the following general exchange transfusion procedure was utilized in the examples that follow. The chamber window of the window preparation was implanted at day one. The chamber was inspected for compliance with inclusion criteria at day 3, and, if satisfactory, carotid artery and jugular vein catheters were implanted. The animal was investigated at day 5 for compliance with systemic and microvascular inclusion criteria, and, if satisfactory, an exchange experiment was started.

Each experiment served as its own control, and all data were relative to the conditions of the animal at the start of the experiment. Video microscopic measurements, systemic hematocrit, heart rate, blood gasses ($pO_2$, pH, $pCO_2$) and blood hemoglobin content (this measurement was initiated with the experiments involving HEMOLINK® dextran and continued with the experiments conducted thereafter) were taken at control prior to exchange of blood. Microscopic measurements at control included capillary flow velocity and arteriolar and venular diameters. Microvascular $pO_2$ measurements were not taken at control, since this measurement can only be carried out at one time point due to toxicity. Macro and micro data collection at control lasted one hour.

After control measurements were collected, the first exchange was initiated. The target was 40% of the original blood mass to be withdrawn and replaced with a blood substitute at the rate of 100 μL/min (the duration of this procedure was 10–20 minutes). At the end of this procedure and after an equilibration and stabilization period of ten minutes, micro and macro measurements, described above, were taken (the duration of this procedure was one hour).

A second exchange targeted at extracting 30% of the original volume was then instituted, using the procedure described above. Micro and macro measurements were taken, and, if this was the final exchange target, the animal was transferred to the $pO_2$ measurement microscope. The animal was injected with the porphyrin compound and intravascular and extravascular $pO_2$ measurements were made in arterioles, venules and the tissue (the duration of this procedure was one hour).

If the final hematocrit target was in the range of 20%, then a third exchange was performed, and microvascular $pO_2$ was not measured during the second exchange. After the third exchange, micro and macro measurements were made, and the animal was transferred to the $pO_2$ measurement microscope.

Statistical Analysis

Data obtained for each group were analyzed to determine if the changes observed within groups were statistically significant. The results of each group are presented by treating each data point as-resulting from an independent experiment. The Mann-Whitney non-parametric test was used on the normalized means to assess if the changes in the parameters were significantly different from control. Results are given in terms of median and interquartile ranges. Changes were deemed statistically significant for $p<0.05$.

The examples that follow are divided into the following sections:

1) Microcirculation Experiments; and II) Clinical Model Experiments.

I. Microcirculation Experiments

EXAMPLE 1

Blood Flow and Hematocrit During Colloid and Saline Hemodilution

The experiments of this example were directed at determining the effect of decreasing hematocrit, as a result of hemodilution, on blood flow velocity. The experiments of this example were conducted on hamsters using dextran 70 and saline.

Figure 2:
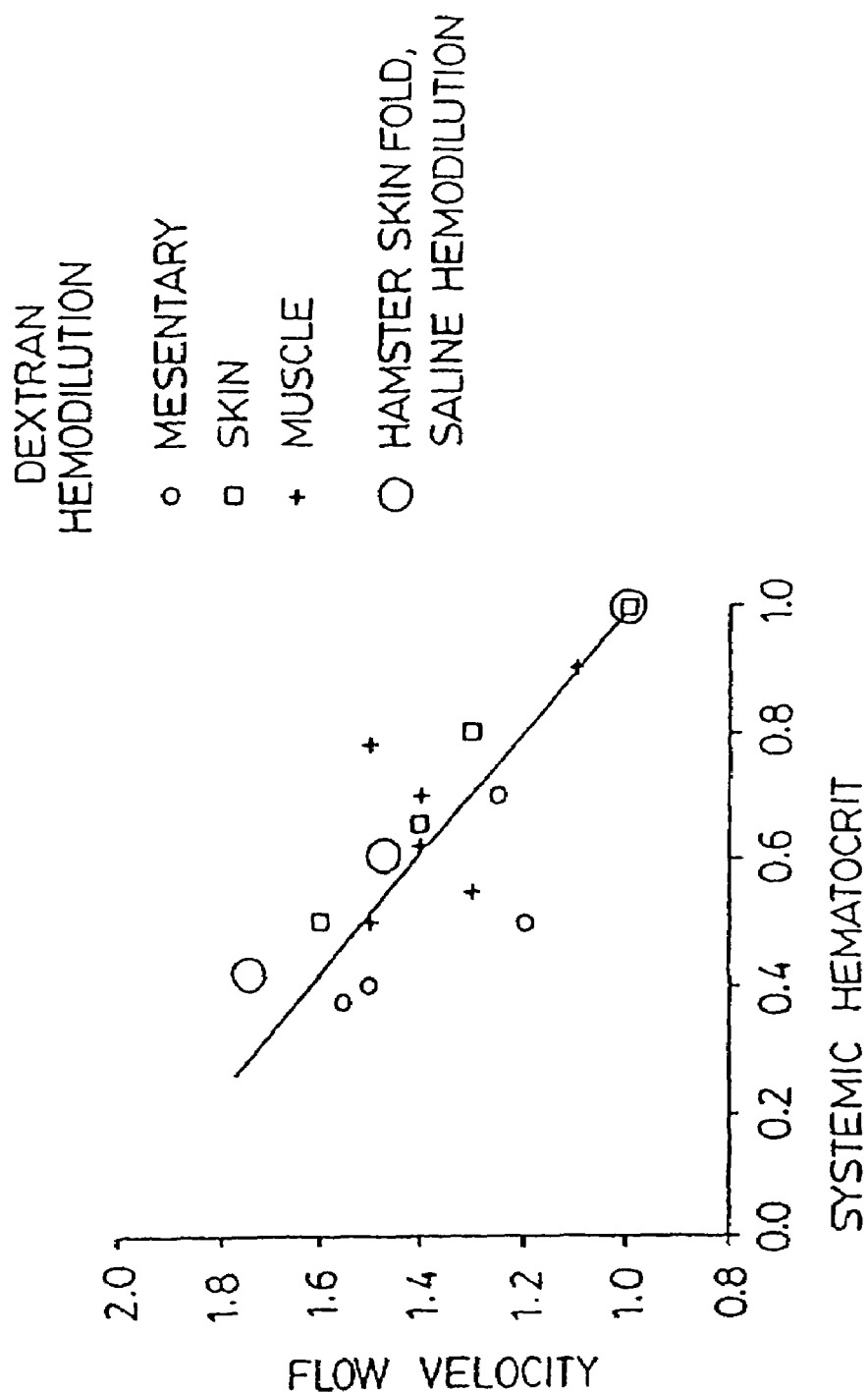
FIG. 2 depicts a plot of flow velocity in the microcirculation as a function of hematocrit reductions with dextran hemodilution and saline hemodilution.

The general experimental procedures (e.g., General Experimental Protocol and Capillary Red Blood Cell Velocity) described above were performed. FIG. 2 depicts a plot of flow velocity in the microcirculation as a function of hematocrit reductions with dextran hemodilution and saline hemodilution. The following designations are used in FIG. 2: i) dextran hemodilution: small circle=mesentery; square=skin; plus sign=muscle; and ii) saline hemodilution: large circle=skin fold. The results indicate that blood flow, as evidenced by the velocity of blood in the vessel of the microcirculation, increases as blood is diluted. The increase is linearly related to the decrease of hematocrit, reflecting the fact that most of the viscous losses in the circulation occur in the microcirculation where the relationship between blood viscosity and hematocrit is linear.

The majority of previous studies have shown that the number of RBCs can be reduced to 25% of the original amount, i.e., a loss of 75% of the original RBC mass, while maintaining circulatory function and flow. Most free hemoglobin solutions (e.g., HBOCs) do not show the linear increase in blood flow with the reduction in hematocrit for very low hematocrits, which is evidenced by non-oxygen carrying diluents. These results indicate the presence of additional processes in the case of free hemoglobin solutions, such as the arterial wall reactions previously alluded to and described in further detail below.

EXAMPLE 2

$PO_2$ Distribution During Dextran 70 and HemoLink® Hemodilution

The experiments of this example were directed at determining the effect of hemodilution on $pO_2$ in the microcirculation by the phosphorescence decay method described above.

Dextran 70 Hemodilution

Measurements of $pO_2$ were made in 50 μm arterioles and the tissue surrounding those arterioles. The results were as follows: arteriole $pO_2$ ($pPO_{2.A}$)=53 mm Hg; tissue $PO_2$ ($pO_{2.T}$)=21 mm Hg. The following equation may then be utilized to calculate $K_A^*$, the constant representing the difference in the decrease in the oxygen partial pressure between i) the arterioles and the tissues and ii) the central arteries and the tissues:

$$K_A^* = \ln[(pO_{2.A} - pO_{2.T})/(pO_{2.a} - pO_{2.T})]$$

where $pO_{2.a}$ is the oxygen tension in a central artery. If one assumes a $pO_{2.a}$=100 mm Hg, then $K_A^*$=ln[(53−21)/(100−21)]=−0.90.

Table 5 sets forth previously obtained (by the present inventors) $pO_2$ values for various hematocrit (α) levels with dextran 70 hemodilution. The convection diffusion model allows comparison of measured values to theoretical values. Changes in blood viscosity (γ) were not measured directly, but were inferred from the change in blood flow velocity in the microcirculation; the relative viscosity γ relates to the viscosity of whole blood (γ=1.0). The oxygen carrying capacity was assumed to be directly proportional to hematocrit (i.e., ignoring oxygen carried by plasma). Table 5 summarizes measured and theoretical $pO_{2.A}$ values following dextran 70 hemodilution. Predicted values for each level of hemodilution were obtained by using model results where $K_A^*$ was multiplied by the corresponding γ/α ratio.

TABLE 5

| α | γ | γ/α | $pO_{2.A}$ Theor. mm Hg | $pO_{2.A}$ Meas. mm Hg | Wall Grad. mm Hg | $pO_{2.T}$ mm Hg |
|---|---|---|---|---|---|---|
| 1.0 | 1.00 | 1.0 | 53 | 55 | | 21 |
| 0.8 | 0.80 | 1.0 | 53 | | | |
| 0.6 | 0.67 | 1.12 | 56 | 55 | 21 | 21 |
| 0.4 | 0.57 | 1.42 | 42 | 54 | 22 | 20 |
| 0.2* | 0.50 | 2.50 | 29 | 37 | 17 | 8 |

TABLE 5-continued

| α | γ | γ/α | $pO_{2,A}$ Theor. mm Hg | $pO_{2,A}$ Meas. mm Hg | Wall Grad. mm Hg | $pO_{2,T}$ mm Hg |
|---|---|---|---|---|---|---|

*Animals do not tolerate this low hematocrit. The viscosity factor γ is deduced from the effect on velocity.

The results presented in Table 5 indicate that a reduction of hematocrit to 60% of the original amount, i.e, a loss of 40% of the original RBC mass, or a hemoglobin concentration (in RBCs) of 9%, does not normally change tissue oxygenation. This is true in terms of autoregulatory responses and in terms of tissue oxygenation. The model predicts that blood $pO_2$ in the arterioles would be significantly lower as hematocrit is reduced to 40% and 20% of the normal value. However, as the data exhibit, this does not take place for reductions of 40%, indicating that the arterioles elicit a sufficiently strong autoregulatory response aimed at sustaining $pO_2$. Further reductions of hematocrit cause an important decline in tissue $pO_2$. Moreover, the wall gradient at extreme hemodilution is low, reflecting vasodilation needed to respond to lower arteriolar oxygen tension.

HemoLink® Hemodilution

HEMOLINK® Hemodilution

Hemodilution with HEMOLINK® was carried out in an analogous manner to that described above for dextran 70. The results are set forth in Table 6.

TABLE 6

| (Htc)α* | γ | γ/α | Theor. $pO_{2,A}$ mm Hg | $pO_{2,A}$ Meas. mm Hg | Wall Grad. mm Hg | $pO_{2,T}$ mm Hg |
|---|---|---|---|---|---|---|
| (0.6) 0.86 | 0.65 | 0.97 | 61 | | | |
| (0.4) 0.80 | 0.66 | 0.89 | 59 | 55 | 23 | 17 |
| (0.2) 0.73 | 0.54 | 0.91 | 62 | 53 | 28 | 5 |

*α shows the oxygen carrying capacity of the mixture of HEMOLINK ® (concentration: 10 g/100 mL) and RBCs. The numbers are normalized relative to the oxygen carrying capacity of normal blood.

*α shows the oxygen carrying capacity of the mixture of HEMOLINK® (concentration: 10 g/100 mL) and RBCs. The numbers are normalized relative to the oxygen carrying capacity of normal blood.

The results in Table 6 indicate that HEMOLINK® maintained arteriolar $pO_2$ for all levels of hemodilution. Animals tolerated hemodilution to 20% of the original RBC mass, which is not the case with dextran hemodilution. Though an understanding of the mechanism is not required in order to practice the present invention, the maintenance of arteriolar $pO_2$ appears to be due to a vasoconstrictor effect that reduces blood flow by about 25%. This is evidenced by: i) increased vessel wall gradient (a sign of vasoconstriction); ii, arteriolar vasoconstriction; and iii) a flow increase due to viscosity effects that is lower than that obtained with dextran 70 hemodilution, as evidenced by higher γ values at any given level of RBC mass dilution with HEMOLINK®.

If dilution with HEMOLINK® were to increase blood flow only according to the viscosity effect resulting from colloids, one would expect to obtain $pO_2$ values at the level of 50 μm arterioles that, when calculated according to theoretical predictions, would be approximately 60 mm Hg (for hematocrit=0.4). Though the practice of the present invention does not require an understanding of why the values are approximately the same, the differences between the theoretical figures and the measured figures indicate the existence of some sort of arterial wall reaction. The results suggest that there is a vasoconstrictor effect accounting for decreased blood flow on the order of 25%, since this would be due to a decrease in vessel diameter on the order of 6%. The data obtained shows that arteriolar diameters decrease to 93% of control for hematocrit 0.4 and to 88% of control for hematocrit 0.2. This level of vasoconstriction is also evident from the increase in pressure for hematocrit 0.4 (but not different from control for the greater exchange level).

The results obtained with HEMOLINK® indicate that, following an isovolemic reduction of hematocrit from 10% to 40%, tissue oxygenation (in terms of the $pO_2$ of 50 μm arterioles and tissue to the same level) is sustained at those levels present in normal conditions. Though a precise understanding of the methodology of this effect is not necessary in order to practice the present invention, the observed slight increase in blood pressure and vessel wall gradient and decrease in functional capillary density may be the direct consequence of autoregulatory phenomena, i.e., phenomena aimed at maintaining $pO_2$ in 50 μm arterioles constant in the presence of potentially excess oxygen carrying capacity due to lowered blood viscosity.

Effect of the Results on Blood Substitute Formulations of the Present Invention

The results of this example indicate that HEMOLINK®, in its present formulation, provides too much oxygen and that the viscosity of the resulting blood mixture is too low. While hemodilution with inert colloids depends on low blood viscosity to maintain oxygen carrying capacity, the resulting increase in cardiac output may not be a desirable effect in all cases. Therefore, in some embodiments of the present invention, HEMOLINK® and other oxygen-carrying components, especially HBOCs, are formulated in a solution that contains an inert colloid. In this way, either an increase in viscosity is achieved and/or the oxygen carrying capacity is decreased, while colloid osmotic pressure and plasma retention are maintained.

EXAMPLE 3

Tissue Oxygenation Resulting from

A mixture of 50% HEMOLINK® and 50% dextran 70 was prepared, and tissue oxygenation was determined at hematocrit levels of 60% and 40% of baseline levels. Hemoglobin concentration in the resulting mixture was measured directly by spectrophotometry. In addition, the number of RBCs and the amount of HEMOLINK® were measured directly in blood samples. Though testing was initiated using four animals, only two animals satisfied all criteria for inclusion in an experimental run; the results for the two animals are set forth in Table 7.

TABLE 7

| Htc/α | γ | γ/α | $pO_{2.A}$ | $pO_{2.A}$ Meas. mm Hg | Wall Grad. mm Hg | $pO_{2.T}$ mm Hg |
|---|---|---|---|---|---|---|
| 0.6/0.68 | 0.64 | 0.86 | 55 | | | |
| 0.4/0.54 | 0.76 | 1.41 | 43 | 51 | 27 | 15 |

When the data in Table 7 is compared with that derived from use of HEMOLINK® alone (see Table 6), it is observed that the values of $pO_{2T}$ (17 mm Hg v. 15 mm Hg, respectively, for hematocrit=0.4) are very similar; these values are acceptable in practice. Therefore, both the diluted mixture and HEMOLINK® itself provide adequate tissue oxygenation, despite the fact that the mixture carries only half as much oxygen per unit weight as is carried by HEMOLINK® alone.

EXAMPLE 4

Tissue Oxygenation With HEMOLINK®,

Dextran 70 And HEMOLINK®/Dextran 70 At Hematocrit 0.4

The experiments of this example are directed at determining and comparing the tissue oxygenation of HEMOLINK®, Dextran 70, and HEMOLINK®/Dextran 70 (50%/50%) at hematocrit 0.4. These experiments build upon those set forth in the preceding example.

The efficacy of tissue oxygenation following administration of the above-mentioned compositions was evaluated from information of arteriolar and venular $pO_2$, the percent oxygen saturation of hemoglobin, capillary flow velocity (1/γ), and intrinsic oxygen carrying capacity (α). These parameters were determined as previously described, and oxygen extraction by the microcirculation was determined by the method discussed hereafter. The results are set forth below in Table 8 (relative numbers are indicated where applicable).

TABLE 8

| | Normal Blood | Dextran 70 | HEMOLINK ® | HEMOLINK ®/ Dextran |
|---|---|---|---|---|
| Arteriolar $pO_2$ | 53 | 54 | 55 | 51 |
| Arteriolar $O_2$ % sat. | 0.84 | 0.85 | 0.85 | 0.81 |
| Venular $pO_2$ | 33 | 30 | 20 | 22 |
| Venular $O_2$ % sat. | 0.52 | 0.50 | 0.30 | 0.32 |
| Cap. Velocity | 1.0 | 1.75 | 1.51 | 1.32 |
| $O_2$ carrying capacity | 1.0 | 0.40 | 0.80 | .54 |
| Extraction | 0.32 | 0.22 | 0.50 | 0.26 |

The data in Table 8 for oxygen extraction are derived from measurements of the $pO_2$ gradients at the vessel wall. This value, in combination with the value for oxygen carrying capacity normalized to blood=1, gives an indication of the relative amount of oxygen which is lost between the arterial vessel and the tissue for a given level of tissue oxygenation. In the case of normal (i.e., undiluted blood), the figure is 32%. When blood is diluted with dextran 70, the figure is 9% (i.e., 22% of 40%); when blood is diluted with HEMOLINK®, the figure is 40% (50% of 80%); and when blood is diluted with a dextran/HEMOLINK® mixture, the figure is 14% (26% of 54%).

The results indicate that the dextran/HEMOLINK® mixture is considerably more efficient in delivering oxygen to the tissues than is HEMOLINK® alone. Because the mixture loses much less of its oxygen in moving from the arteries to the capillaries than does HEMOLINK® alone, the mixture has greater reserves of oxygen available to the tissue for oxygenation purposes. Therefore, the compositions of the present invention comprising a non-oxygen carrying component and an oxygen carrying component provide greater reserves of oxygen for the tissues; this result represents an additional, unexpected advantage of the compositions.

EXAMPLE 5

Wall Gradients With HEMOLINK® And HEMOLINK®/Dextran 70 At Hematocrit 0.4

Several of the previous examples were directed at the use of the "awake hamster" model to determine i) partial oxygen pressures in arteries, veins and tissue, and ii) blood pressure in normal blood (control) with HEMOLINK® at hematocrit 0.4, and 50:50 dextran:HEMOLINK® at hematocrit 0.4. This example is directed at the determination of wall gradients using each of those compositions.

As previously indicated, the vessel wall gradient is inversely proportional to tissue oxygenation. In this example, wall gradients were derived from the $pO_2$ measurements in previous studies. The blood pressure data represents mean arterial blood pressure relative to the control. The results are shown in Table 9.

TABLE 9

| Parameter | Control | HEMOLINK ® | HEMOLINK ®/ Dextran |
|---|---|---|---|
| Wall Gradient - Arteriole (mm Hg) | 17.8 | 24.3 | 26.8 |
| Wall Gradient - Venular (mm Hg) | 10.1 | 10.8 | 7.6 |
| Tissue $pO_2$ | 21.4 | 17.0 | 19.2 |
| Blood Pressure | 100% | 112% | 109% |

The data in Table 9 indicate that the HEMOLINK®/dextran composition is effectively equivalent to HEMOLINK® alone when compared for the measured parameters. Moreover, the results of this example, in conjunction with the examples set forth above, indicate that the desirable properties of a blood substitute obtainable by using HEMOLINK® (and, by extrapolation, other HBOCs) alone are also obtainable with the compositions of the present invention (i.e., compositions comprising solutions of an oxygen carrying component in combination with a non-oxygen carrying component).

EXAMPLE 6

Microcirculatory Parameters at Hematocrit of 12–13%

The experiments of this example utilized the previously described procedures to assess various microcirculatory parameters following administration of several different compositions.

TABLE 10

| Exp. | n | Material | Hct % | BP | PaO$_2$ Torr | Grad(A) Torr | Tissue PO$_2$Torr | Venular PO$_2$Torr | Grad(V) Torr | Vasoconstriction | Arteriolar Velocity |
|---|---|---|---|---|---|---|---|---|---|---|---|
| 1 | | Control | | stable | 53 | 17.8 | 20 | 33 | 10 | | |
| 2 | | Dextran | 19 | unstable | 54 | 22 | 20 | 30 | 11 | none | 1.4 |
| 3 | many | HEMOLINK ® | 12 | stable | 53 | 28 | 5 | 10 | 4 | not done | 1.2 |
| 4 | 1 | HEMOLINK ® 33% Dextran 66% | 12 | stable | 69 | 34 | 13 | 25 | 18 | | 0.2 |
| 5 | 2 | HEMOLINK ® 50% Dextran 66% | 12 | stable | 73 | 41 | 17 | 21 | 8 | | 0.3 | 2.6 |
| 6 | many | L-Name | | stable | 57 | 26 | 21 | 28 | 9 | not done | 1.8 |

Six different compositions were administered to hamsters in separate experiments: 1) control (i.e., normal blood); 2) dextran 70 alone; 3) HEMOLINK® alone; 4) HEMOLINK® 33%/dextran 66% (by volume); 5) HEMOLINK® 50%/dextran 50%; and 6) L-Name (L-nitrosyl-arginine-monomethyl-ether; commercially available from, e.g., Sigma). A hematocrit of approximately 12% of the control was achieved in experiments 3)–5) following three exchange perfusions. Only two hemodilutions (i.e., two exchange perfusions) were performed for the experiment with dextran alone (experiment number 3) because the animals do not tolerate three dilutions with this composition. The L-name composition was injected into animals (i.e., it was not administered to effect hemodilution).

The resulting data is set forth in Table 10. Referring to Table 10, PaO$_2$=arterial PO$_2$; Grad(A)=arteriolar/tissue gradient; and Grad(V)=venular/tissue PO$_2$ gradient. The data regarding vasoconstriction is relative to the control (experiment number 1).

The data in Table 10 indicate that hemodilution with the hemoglobin-based oxygen carrier (HBOC) HEMOLINK® decreased tissue PO$_2$ from approximately 20 to 5 mm Hg. This was accompanied by an increase of the arteriolar/tissue PO$_2$ gradient from about 17 to 28 mm Hg, consistent with the vasoconstriction previously determined to be caused by this product. When the HEMOLINK® was mixed with the non-oxygen-carrying plasma expander dextran, tissue PO$_2$ increased to 13 and 17 mm Hg, respectively, with 33% and 50% mixtures of HEMOLINK®/dextran. However, in the experiments with the HEMOLINK®/dextran compositions, the arteriolar/tissue PO$_2$ gradient remained high, a consequence of vasoconstriction still being produced by the hemoglobin.

These experiments, in conjunction with some of the results from the previous examples indicate that if the O$_2$ availability is increased by the extracellular location of hemoglobin, then, in order to prevent autoregulatory vasoconstriction at the arteriolar level, one or more of the following compensations must take place: i) increased viscosity, ii) decreased O$_2$ carrying capacity, or iii) increased O$_2$ affinity.

EXAMPLE 7

The experiments of this example provide evidence that increased viscosity prevents autoregulatory vasoconstriction at the arteriolar level. The microvasculature experiments of this example were performed utilizing a composition comprising HEMOLINK® and polyvinylpyrrolidone (PVP), 750,000 dalton molecular weight.

Aqueous solutions of i) HEMOLINK®, ii) 50:50 HEMOLINK®:dextran molecular weight 70,000 (by volume), and iii) 100:4 HEMOLINK®:PVP molecular weight 750,000 (by volume) were prepared at a total solute concentration, in each case, of 10 g/100 mL. The compositions were tested in the "awake hamster" model described above. PVP is used experimentally as a plasma expander and has also been used in humans for the same purpose; its principal property is that of increasing plasma blood viscosity. The use of PVP substantially increases the viscosity of the solution, to a value estimated at about 15 centipoise (substantially equivalent to that of whole blood).

The animals were subjected to an isovolemic exchange of blood with each of the compositions to achieve a final hematocrit of 0.20 of control (i.e., 20% of original RBC mass) or an effective hematocrit of about 10%. By the procedures previously described, measurements were taken of the arterial pressure, wall gradient, blood pressure and tissue oxygen. The results are set forth below in Table 11.

Figure 3:
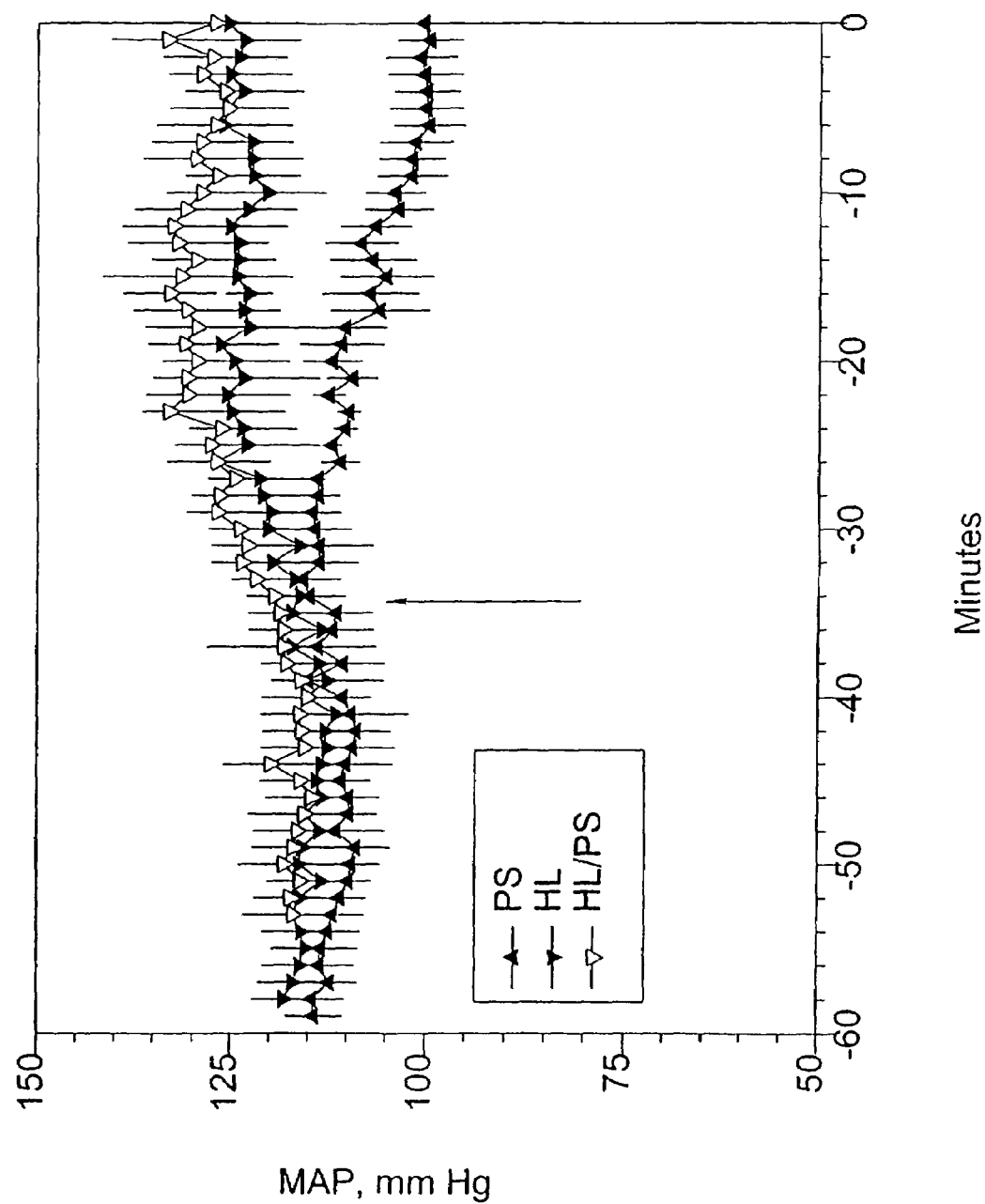
FIG. 3 graphically presents mean arterial blood pressure in rats prior to and during an exchange transfusion (arrow) with HEMOLINK® (▼), pentastarch (▲) and a 50/50 (volume/volume) mixture of HEMOLINK®+pentastarch (∇).

The results in Table 11 indicate that the increased viscosity of the HEMOLINK®:PVP composition significantly lowers the vessel wall gradient, making more oxygen available to the tissue, compared to the other two compositions. This increased viscosity causes dilation of the vasculature and normalizes the distribution of oxygen in the microcirculation. Though an understanding of the underlying mechanism is not required in order to practice the present invention, the mechanism for vasodilation with compositions of increased viscosity is believed to be two-fold. First, decreased oxygen delivery of blood due to lower hemoglobin causes autoregulatory effects analogous to those observed with the previously described oxygen-carrying compositions comprising other inert, non-proteinaceous colloids.

procedures in the art. FIG. 3 graphically presents arterial blood pressure prior to and during the exchange transfusion (indicated by the arrow in FIG. 3). Referring to FIG. 3, (□) represents HEMOLINK®, (□) represents pentastarch and (□) represents the mixture of HEMOLINK®+pentastarch. Using the statistical analyses described above, there are no significant differences between HEMOLINK® alone and the composition of HEMOLINK®/pentastarch.

TABLE 11

|  | Hb Content α | Relative Viscosity γ | $pO_2$ Arterioles mm Hg | Wall Gradient mm Hg | FCD | Mean Arterial Blood Pressure % Normal | $pO_2$ Tissue mm Hg |
|---|---|---|---|---|---|---|---|
| HEMOLINK ® | 0.73 | 0.54 | 53 | 28 | 0.64 | −14% | 5 |
| HEMOLINK ® & Dextran | 0.54 | 0.76 | 51 | 27 | 0.78 | +9% | 13 |
| HEMOLINK ® & PVP | 0.51 | 1.00 | 46 | 15 | 0.45 | −3% | 16 |

Second, increased shear stress at the vessel wall increases release of endogenous vasodilators such as prostacyclin.

In addition, even though the $O_2$ capacity of the HEMOLINK®/PVP mixture is lower than that of HEMOLINK® alone and its viscosity is higher, the arteriolar/tissue $PO_2$ gradient is reduced, and tissue $PO_2$ is increased from 5 to 16 mm Hg. These results are consistent with the theoretical formulation alluded to previously. However, it is believed that the mixture of HEMOLINK® and PVP is not suited to development as a blood substitute, and the functional capillary density is lower than desired.

II. Clinical Model Experiments

EXAMPLE 8

Use of Pentastarch, HEMOLINK®, and a Mixture Thereof Under Clinical Conditions

This example relates to experiments conducted in vivo using male Sprague-Dawley rats under severe stress. The experiments of this example provide information relevant to the clinical use (e.g., in an operating theater environment) of the compositions of the present invention.

Exchange Transfusion

The animals were instrumented 24 hours prior to initiation of experiments, and all experiments were conducted in the awake state. A catheter was placed in the femoral artery and another in the femoral vein. The animal was restrained in an experimental cage. First, an exchange transfusion was performed in which about 50% of the blood of the animal was removed and replaced with a test composition; the test compositions assessed were pentastarch, HEMOLINK® and a HEMOLINK®/pentastarch mixture (50:50 by volume). A peristaltic pump was used to simultaneously withdraw blood and infuse one of the test compositions at a rate of 0.5 mL/min. The duration of the exchange was calculated to achieve exchange of 50% of the estimated total blood volume, based on 65 mL of blood per kg body weight as the standard blood volume of the rat.

Mean Arterial Blood Pressure During Exchange

As the exchange transfusions proceeded, mean arterial pressures were measured through the catheter, by standard Physiological Status During Hemorrhage Animals were subjected to a 60% hemorrhage procedure analogous to that described in the preceding example. More specifically, 60% of the total blood volume was calculated, using the aforementioned 65 mL/kg estimate. The calculated amount of blood was then removed using a simplified exponential protocol similar to that developed by Hannon et al. ("Blood and Acid-base Status of Conscious Pigs subjected to Fixed-volume Hemorrhage and Resuscitated with Hypertonic Saline Dextran," Circulatory Shock 32:19–29 [1990]). At the beginning of each 10 minute period of the hemorrhage, blood was removed from an arterial site using a syringe pump running at a rate of 0.5 mL/min. The duration of each withdrawal was calculated so that 60% of the total blood volume was removed over 60 minutes.

Figure 4:
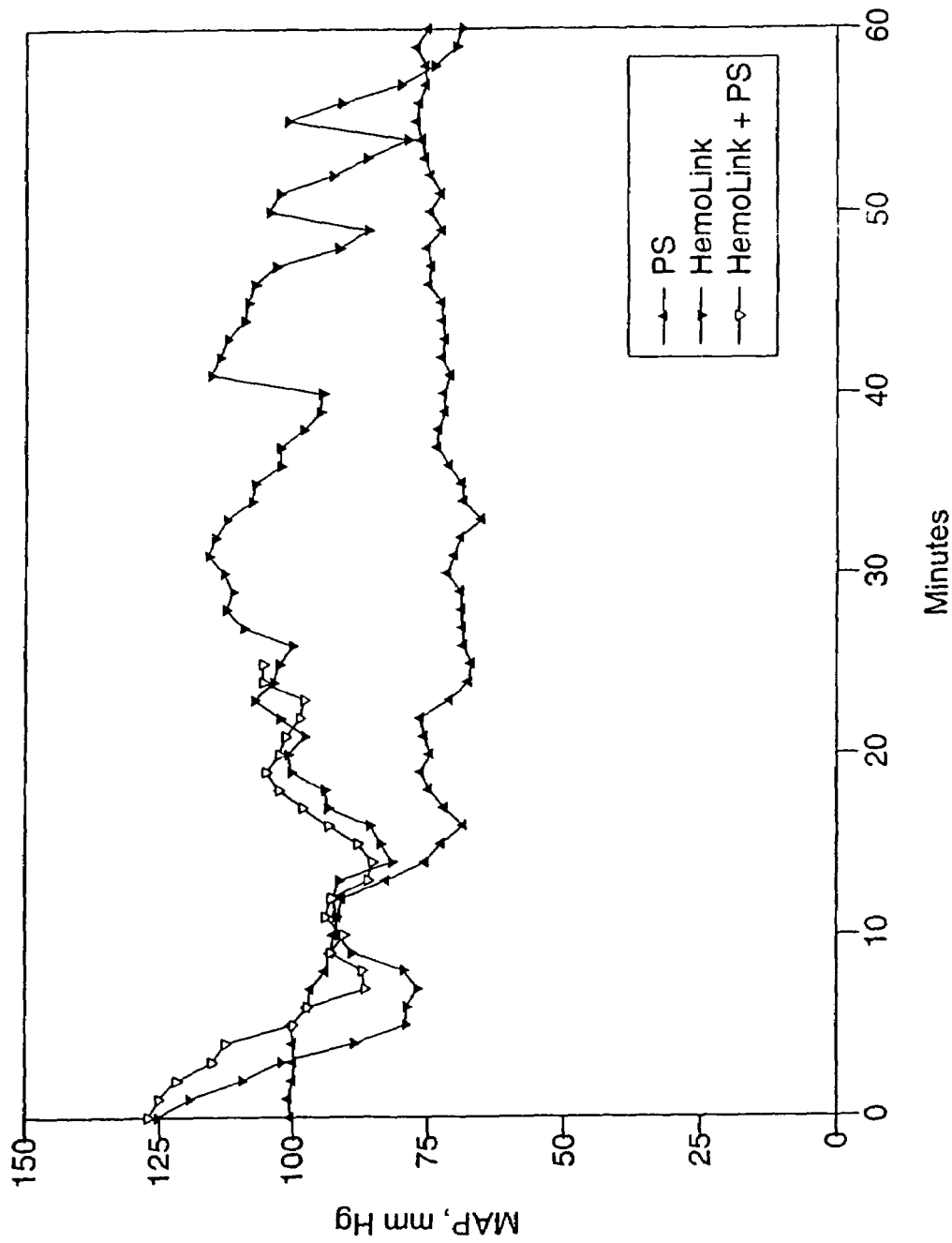
FIG. 4 graphically presents mean arterial blood pressure in rats following exchange transfusion with HEMOLINK® (▼), pentastarch (▲) and a 50/50 (volume/volume) mixture of HEMOLINK®+pentastarch (∇), during a 60% blood volume hemorrhage.

Mean arterial blood pressure was measured through the catheter, and data are presented graphically in FIG. 4; in FIG. 4, the symbols depicting each composition are the same as set forth in FIG. 3. Of note, the animals transfused with the HEMOLINK®/pentastarch composition start the bleed with a higher blood pressure, which initially falls quite steeply. Both the HEMOLINK®/pentastarch composition and HEMOLINK® alone preserve the blood pressure well during the first 50 minutes.

The hemorrhage test described above represents a relatively severe test model. Only about 50% of the animals, even without an exchange transfusion, survive beyond 120 minutes from the onset of the 60% hemorrhage, and even fewer of those transfused with a test solution survive (data not shown).

Other measurements were also determined during the hemorrhaging, including heart rate (measured from the pressure trace of the mean arterial pressure measurements), and pH, $pCO_2$, $pO_2$, lactate accumulation, and base excess (measured by standard analysis of the blood). The results (not shown) from animals transfused with HEMOLINK® and those transfused with the HEMOLINK®/pentastarch composition were substantially equivalent with the following exception. The HEMOLINK®/pentastarch composition resulted in more lactate accumulation, reflecting the fact that this composition carries less oxygen. Lactate accumulation is a direct reflection of the status of tissue oxygenation; that is, lactate accumulates when tissue is not supplied with sufficient oxygen.

The findings of the experiments of this example indicate that a mixture of an oxygen-carrying component and a non-oxygen carrying component provides similar, if not superior, results to that achieved with an oxygen-carrying component alone.

EXAMPLE 9

Use Of Pentastarch, Modified Hemoglobins, and Mixtures Thereof Under Clinical Conditions The experiments of this example evaluate two oxygen-carrying components, bovine hemoglobin modified by conjugation with polyethylene glycol (PEGHb or PEG) and αα-Hb, alone and in combination with a the non-oxygen-carrying component, the plasma expander pentastarch (PENTASPAN; DuPont).

Nature of the Compositions

The properties of several of the compositions used in this example are compared in Table 12. The PEGHb+pentastarch composition and the αα-Hb+pentastarch composition comprised 50% of each composition by volume. As indicated in Table 12, both PEGHb and pentastarch have high colloid osmotic pressure (COP) values, and both have a viscosity that approximates that of blood (in the measuring system used, water and purified hemoglobin have viscosities of 1 centipoise).

TABLE 12

| Solution | COP (mm Hg) | Hemoglobin (g/dL) | Viscosity (centipoise) |
| --- | --- | --- | --- |
| Blood | 26.0 | 15.0 | 4.0 |
| PENTASPAN ® | 85.0 | 0.0 | 4.0 |
| PEGHb | 81.3 | 6.0 | 3.4 |
| PEGHb + PENTASPAN ® | 98.0 | 3.0 | 3.2 |

Exchange Transfusion

A 50% isovolemic exchange transfusion was performed in awake rats using the procedure described in the preceding example. Table 13 indicates the effect of the exchange transfusion (±sem) on blood volume, hematocrit, total hemoglobin, and plasma hemoglobin for several of the compositions.

TABLE 13

| Solution | Blood Volume (mL/kg) | Hct (%) | Total Hb (g/dL) | Plasma Hb (g/dL) |
| --- | --- | --- | --- | --- |
| Controls | 56.3 ± 2.5 | 38.6 ± 0.9 | 13.8 ± 0.3 | 0.0 ± 0.0 |
| Pentastarch | 71.1 ± 5.7 | 18.4 ± 1.0 | 6.8 ± 0.4 | 0.0 ± 0.0 |
| PEGHb | 74.0 ± 1.6 | 15.8 ± 0.4 | 7.6 ± 0.1 | 2.0 ± 0.1 |
| PEGHb + PENTASPAN ® | 91.0 ± 3.0 | 14.8 ± 0.3 | 5.6 ± 0.2 | 1.0 ± 0.1 |

Referring to Table 13, the decreases in hematocrit and hemoglobin concentration for the experimental groups indicate that the exchange procedure led to significant expansion of the plasma volume in the PEGHb, PENTASPAN® and PEGHb+PENTASPAN® animals.

Physiological Status During Hemorrhage

Next, the rats were subjected to a 60% hemorrhage over 1 hour; this protocol, known to be lethal in approximately 50% of animals, was performed as described in Example 8.

Figure 5:
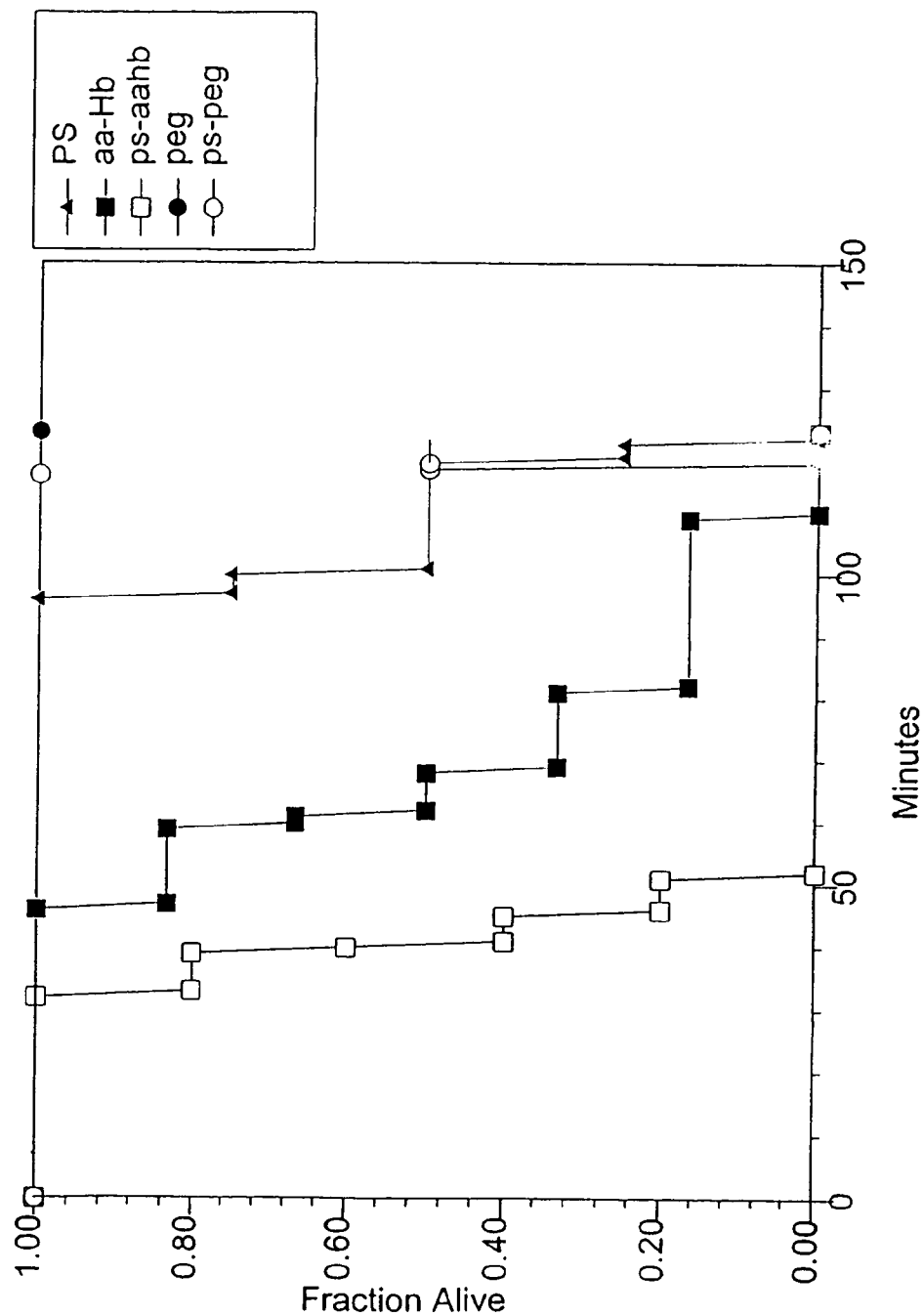
FIG. 5 depicts rat survival following exchange transfusion with pentastarch (▲), αα-Hb (■), PEG-Hb (●), pentastarch+αα-Hb (□), and pentastarch+PEG-Hb (○) and after the initiation of a 60% hemorrhage.

In FIGS. 5–10, the following designations apply: pentastarch (▲), αα-Hb (■), PEG-Hb (●), pentastarch+αα-Hb (□), pentastarch+PEG-Hb (○), and control animals (♦). FIG. 5 depicts animal survival over a 2 hour period beginning with the start of hemorrhage. As indicated by the data in FIG. 5, hemodilution with pentastarch alone led to significantly reduced survival, while hemodilution with either PEGHb alone or PEGHb+pentastarch led to complete survival; survival following hemodilution with the compositions comprising αα-Hb was much lower than with the compositions containing PEGHb.

Figure 6C:
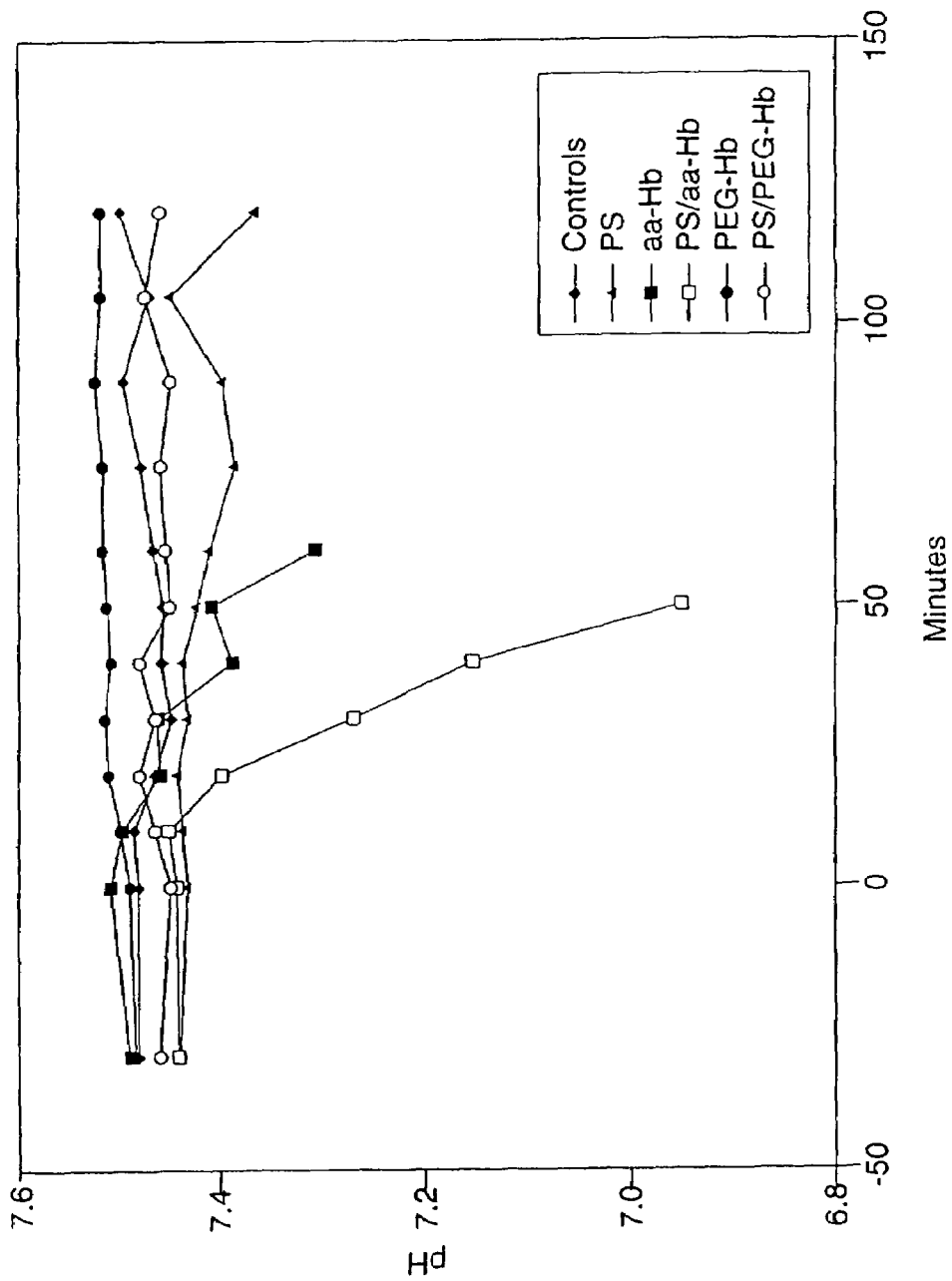
Figure 6D:
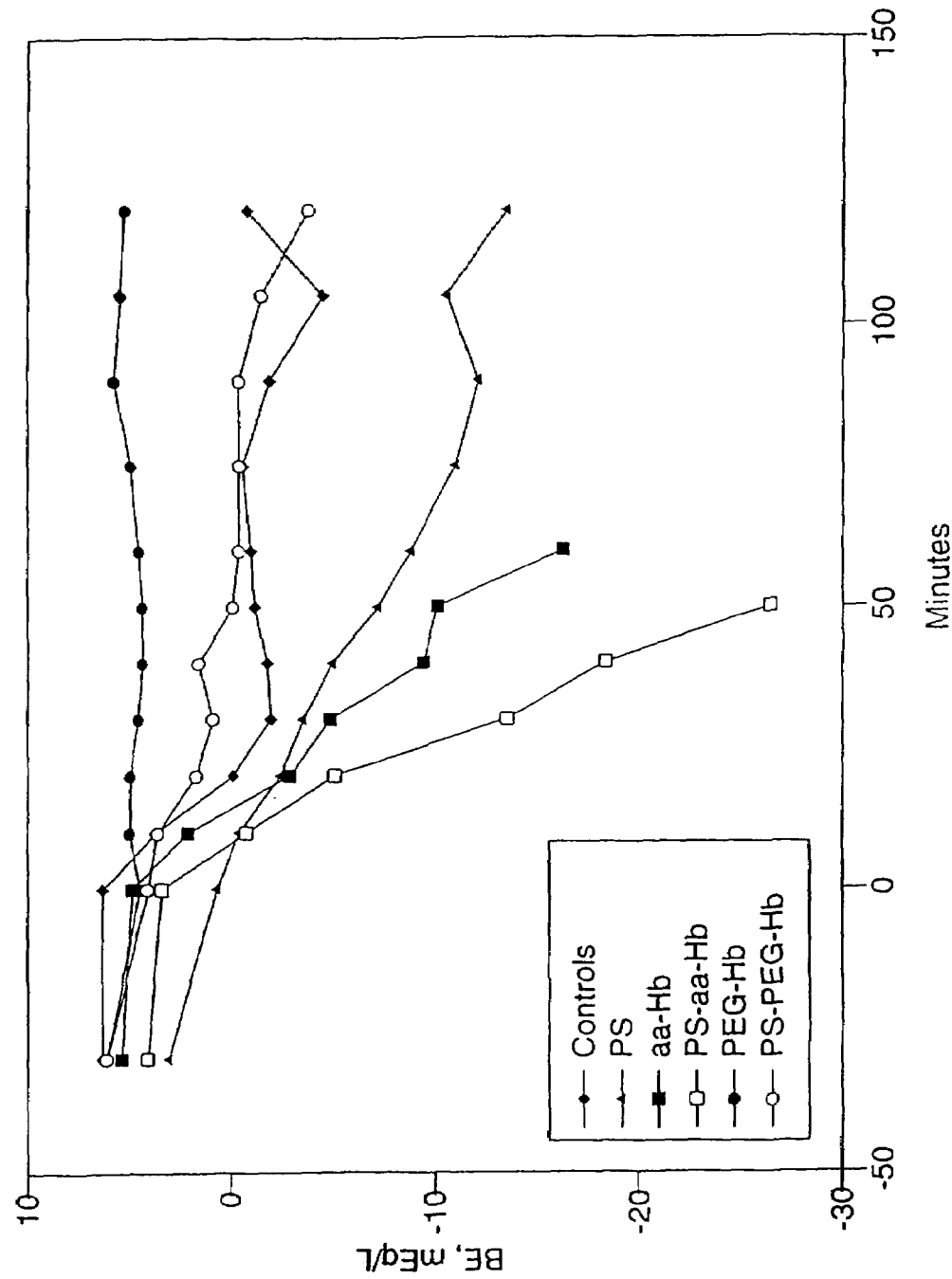

FIG. 6A–D graphically depict the acid-base status of control rats (♦) and of rats following exchange transfusion with pentastarch (▲), αα-Hb (■), PEG-Hb (●), pentastarch+αα-Hb (□), and pentastarch+PEG-Hb (○) and after the initiation of a 60% hemorrhage. FIG. 6A depicts $PaO_2$, FIG. 6B depicts $PaCO_2$, FIG. 6C depicts arterial pH, and FIG. 6D depicts base excess.

FIGS. 6A–D are directed at the animals' acid-base status determined over a 2 hour period from the start of hemorrhage. More specifically, FIG. 6A depicts $PaO_2$, FIG. 6B depicts $PaCO_2$, FIG. 6C depicts arterial pH, and FIG. 6D depicts base excess. As indicated in FIGS. 6A–C, neither the PEGHb nor the PEGHb+pentastarch animals had significant respiratory alkalosis compared to the pentastarch animals. Moreover, neither the PEGHb nor the PEGHb+pentastarch animals developed significant acidosis, even at the end of the hemorrhage period. Acid base status was well preserved in the PEGHb and PEGHb+pentastarch animals (FIG. 6D). Again, neither of the compositions comprising αα-Hb performed as well as PEGHb+pentastarch animals or the pentastarch animals.

FIG. 7 shows the production of lactic acid following administration of each of the compositions. As depicted in FIG. 7, generation of lactic acid during the hemorrhage was significantly greater in the αα-Hb animals (alone and in combination with pentastarch) and the pentastarch animals than in the other groups. Notably, the controls animals (no prior exchange transfusion) and the PEGHb+pentastarch animals had approximately equal minimal rises in lactic acid, even though the total hemoglobin concentration and hematocrit were significantly less in the PEGHb+pentastarch group. (See Table 13).

FIG. 8A depicts mean arterial blood pressure of control rats (□) and of rats following exchange transfusion with pentastarch (□), PEG-Hb (●), and PENTASPAN®+PEG-Hb (○) at time −60 minutes, and after the initiation of a 60% hemorrhage at time 0 minutes. As indicated by the data in FIG. 8A, blood pressure did not rise in any of the groups during the exchange transfusion (i.e., from −60 to 0 minutes), but fell significantly in the controls and in the pentastarch animals during hemorrhage (i.e., from 0 to 120 minutes). Both the PEGHb and the PEGHb+pentastarch compositions "protected" the animals from hypotension.

FIG. 8B depicts mean arterial blood pressure in control rats (♦), and rats following exchange transfusion with pentastarch (▲, point B), αα-1Hb (■, point B), and pentastarch+αα-Hb (□, point A), and after the initiation of a 60% hemorrhage (point C). As set forth in FIG. 8B, the control animals and the pentastarch animals maintained mean arterial pressure to a greater extent than the pentastarch+αα-Hb animals.

Figure 9:
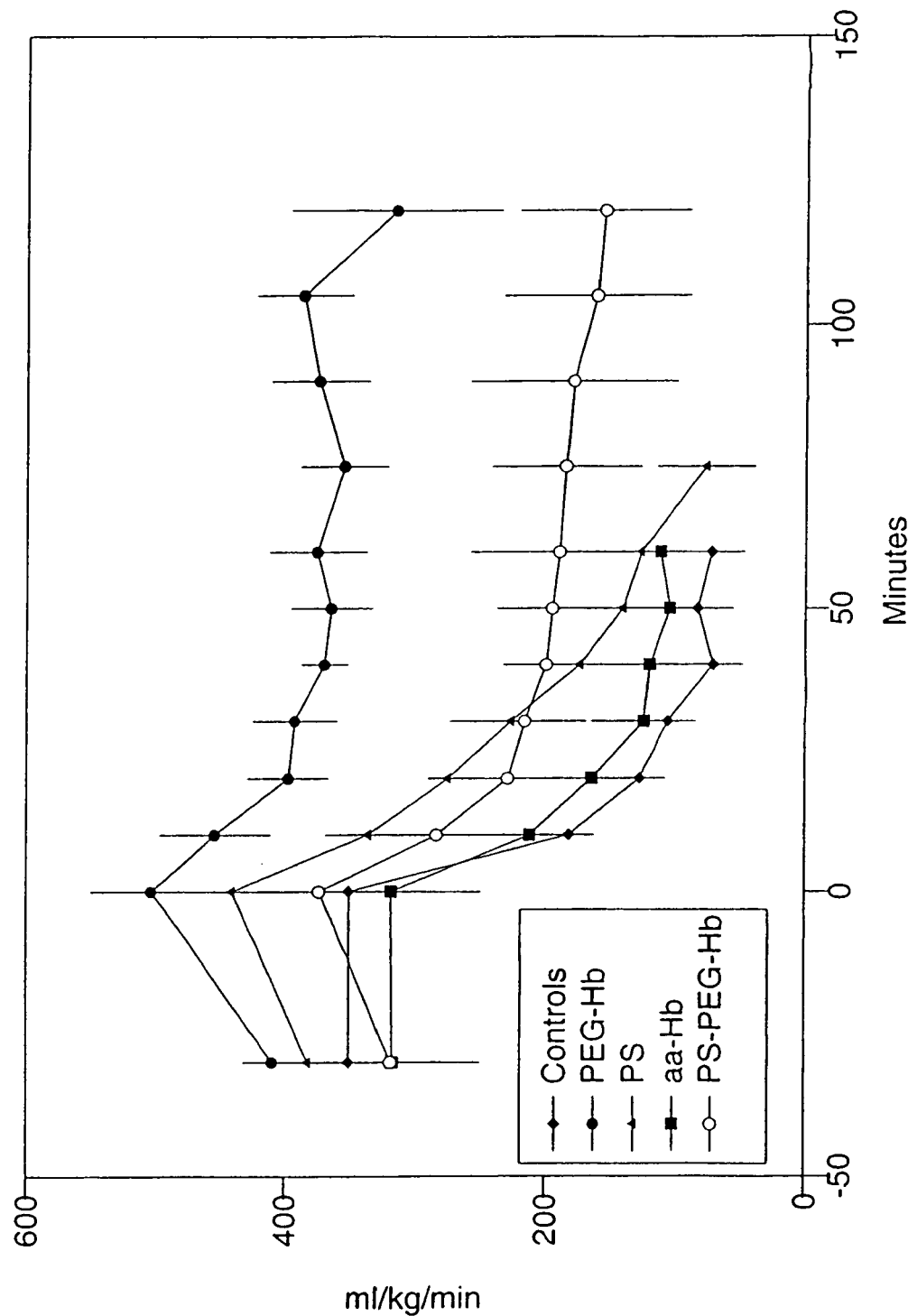
FIG. 9 depicts cardiac output in control rats (♦) and in rats following exchange transfusion with pentastarch (▲), αα-Hb (■), PEG-Hb (●), and pentastarch+PEG-Hb (○) and after the initiation of a 60% hemorrhage at 0 minutes.
Figure 10:
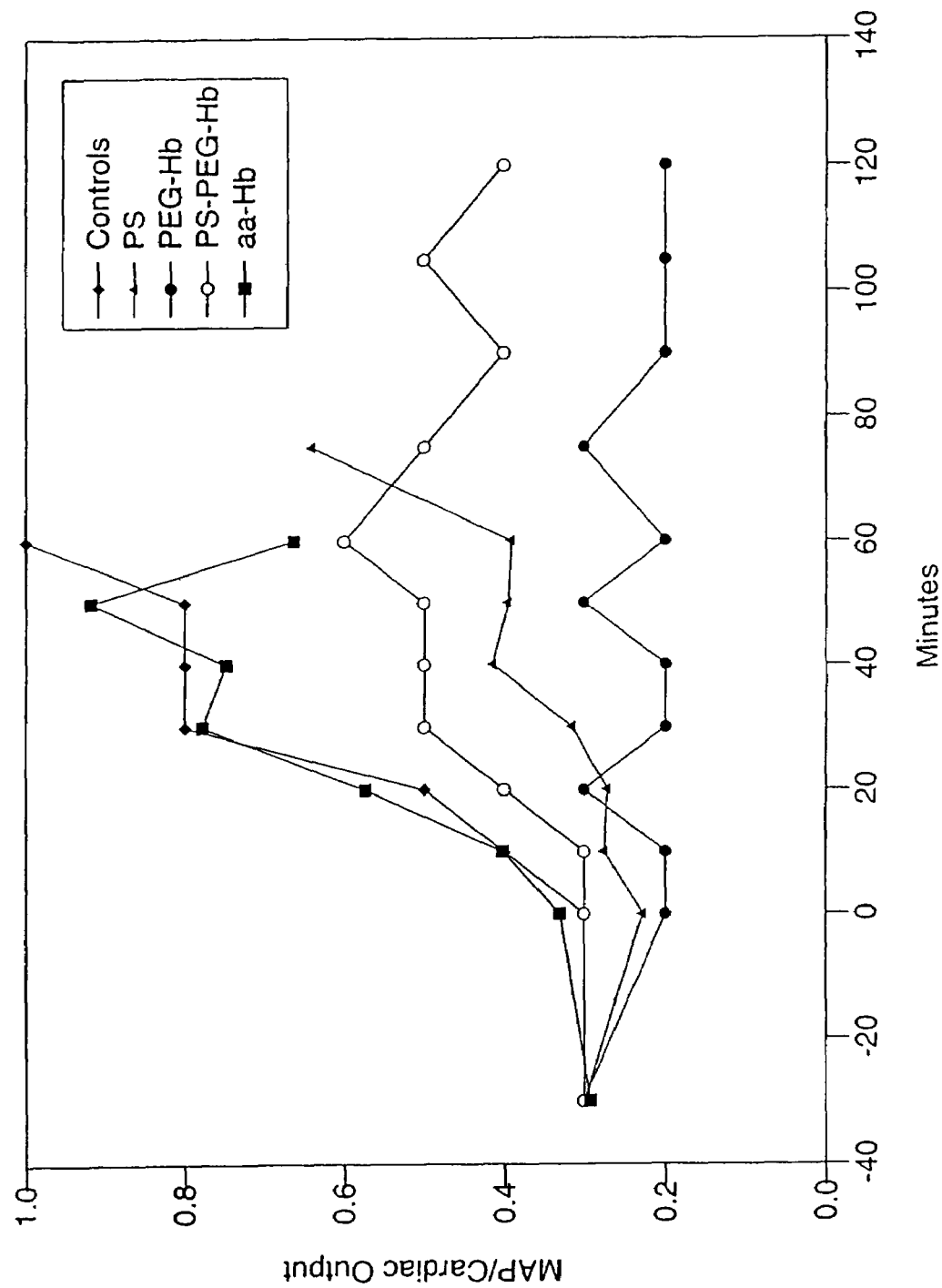
FIG. 10 depicts systemic vascular resistance in control rats (♦) and of rats following exchange transfusion with pentastarch (▲), αα-Hb (■), PEG-Hb (●), and pentastarch+PEG-Hb (○) and after the initiation of a 60% hemorrhage at 0 minutes.

FIG. 9 and FIG. 10 depict relative cardiac output and systemic vascular resistance, respectively. Cardiac output refers to the amount of blood pumped by the heart in a unit period of time (e.g., liters per minute); relative cardiac output refers to the cardiac output of the three experimental groups relative to the control period (−30 minutes). As depicted in FIG. 9, cardiac output was higher in PEGHb and PEGHb+pentastarch compared to the other groups. FIG. 10 indicates that systemic vascular resistance remained low in both PEGHb and PEGHb+pentastarch animals relative to the other animals.

The results presented above indicate that the PEGHb+pentastarch mixture was superior to compositions comprising αα-Hb. In addition, the PEGHb+pentastarch mixture performed similarly to the PEGHb composition alone. This was true even though the hemoglobin concentration to which the animals were exposed and the amount of hemoglobin product used were less by half with the mixture, offering the advantage of reducing the concentration of hemoglobin given to patients, thereby reducing both cost and potential side effects. Though a precise understanding of why the mixture is effective is not required in order to practice the present invention, the effectiveness of PEGHb+pentastarch is thought to result from its preservation of all four of the previously discussed properties, namely oncotic pressure, viscosity, oxygen affinity, and low oxygen capacity. Indeed, the results indicate that compositions comprising i) an oxygen-carrying component (e.g., a HBOC) with high oncotic pressure, oxygen affinity and viscosity and ii) a non-oxygen-carrying plasma expander with similar oncotic pressure and viscosity provide an optimal blood product.

EXAMPLE 10

Survival Data with Modified Hemoglobins,
Non-Oxygen-Carrying Components, and
Compositions Thereof This example is directed at animal survival using several modified hemoglobin products (ie., oxygen-carrying components), non-oxygen-carrying components, and several mixtures comprising an oxygen-carrying component and a non-oxygen-carrying component.

Experimental Protocol

Generally speaking, the experiments of Examples 10–15 were carried out as described in Example 8. Briefly, male Sprague-Dawley rats were instrumented, under anesthesia, 24 hours prior to hemodilution. Instrumentation consisted of cannulation of the femoral artery and vein and exteriorizing the catheters so that the animals had free range in their cages in the following 24 hours. The experiments were all carried out in awake animals, loosely constrained to restrict gross movements. Arterial pressure was continuously monitored at one femoral artery. Thereafter, 50% of the estimated blood volume (60 mL/kg) was exchanged with test material at a rate of 0.5 mL/min. This was performed with a peristaltic pump so that withdrawal and infusion were done simultaneously at the same rate.

Hemorrhage was initiated after the exchange transfusion; the hemorrhage volume was calculated to be 60% of the original blood volume. Blood was removed using a simple exponential protocol so that the hemorrhage was complete after 60 minutes. Specifically, the withdrawal pump was driven at 0.5 mL/min for decreasing periods of time at the start of each 10 minute period for a total of 60 minutes.

Animal Survival

Table 14 summarizes all the materials used in the experiments. Referring to Table 14, it should be noted that the designation "DBBF" refers to human hemoglobin crosslinked between the alpha chains ("αα-Hb"); this was produced by the United States Army and provided as a gift. Two hemoglobin products modified with polyethylene glycol were tested. PHP Hemoglobin is a human-derived product from Apex Bioscience, and PEGHb is a bovine-based product obtained from Enzon, Inc. The two PEG-modified hemoglobin products (PHP and PEGHb) gave qualitatively the same results. Though the experiments described hereafter utilize PEGHb, other products comprising PEG-modified hemoglobin and a non-oxygen-carrying component, including, but not limited to, products comprising PHP, are contemplated by the present invention.

TABLE 14

| | | | Materials | | | | |
|---|---|---|---|---|---|---|---|
| Abbr. | Name | Raw Material | Source | Mol Wt. | COP | Viscosity | Oxygen Affinity |
| PS | PENTASPAN ® | Corn | DuPont Merck | *250,000 | High | High | None |
| HS | Hetastarch | Corn | Fresenius | *480,000 | Low | undetermined | None |
| BOV | Bovine Hemoglobin | Cow Blood | Enzon | 64,000 | Low | Low | High |
| DBBF | αα-Hemoglobin | Human Blood | U.S. Army | 64,000 | Low | Low | Normal |
| β82 | β82 Hemoglobin | Human Blood | Hemosol | 64,000 | Low | Low | High |
| TM | TM Hemoglobin | Human Blood | Hemosol | 64,000 | Low | Low | Low |
| HL | HEMOLINK ™ | Human Blood | Hemosol | 128,000 | Low | Low | High |
| PHP | PHP Hemoglobin | Human Blood | Apex Bioscience | 105,000 | Moderate | Moderate | Mod High |
| PEG | PEG Hb | Cow Blood | Enzon | 118,000 | High | High | High |

*weight-average molecular weight.

One of the major criteria for an effective blood substitute product is enhanced survival, and Table 15 provides several indices of animal survival. Specifically, Table 15 sets forth the mean times to death; the column indicating "initial death" refers to the number of minutes that elapsed following the initiation of hemorrhage before the death of the first animal, and the column indicating "% survival" refers to the number of minutes that have elapsed when 50% of the animals have expired.

Referring to Table 15, all of the mixture blood products (i.e., PENTASPAN®+HEMOLINK®; hetastarch+ HEMOLINK®; PENTASPAN®+PEGHb; and PENTASPAN®+DBBF) in Table 15 contained 50% (by volume) oxygen-carrying component and 50% non-oxygen-carrying component. These data show that all of the modified hemoglobins (regardless of their properties), with the single exception of hemoglobin modified by conjugation with polyethylene glycol (PEG), show a diminished survival compared to controls or PENTASPAN®. Indeed, in studies with a mixture of PEGHb and a non-oxygen-carrying component, most of the animals were still alive after the one-hour observation period following hemorrhage.

As indicated in Table 15, of the mixture blood products, only PENTASPAN®+PEGHb performed as well as or better than the controls (control animals underwent no exchange transfusion). Moreover, PENTASPAN®+PEGHb was nearly as effective in survival as PEGHb, which is surprising given the fact that the total hemoglobin is less in the PENTASPAN®+PEGHb animals, and the plasma hemoglobin is only approximately 1 g/dL. The animal survival data with the other mixture blood products was much less than the control animals.

TABLE 15

Survival

| Sample | Initial Death (Min) | Slope | 50% Survival (minutes) |
|---|---|---|---|
| Controls | 110 | −0.0247 | 130.2 |
| PS | 96 | −0.0325 | 111.4 |
| KS | 38 | −0.0237 | 59.1 |
| DBBF | 46 | −0.0175 | 74.6 |
| TM | 41 | −0.0559 | 49.9 |
| B82 | 40 | −0.0383 | 53.1 |
| HL | 39 | −0.0289 | 56.3 |
| PEG Hb | >120 | | >120 |
| PS/HL | 33 | −0.0182 | 60.5 |
| HS/HL | 40 | −0.0204 | 64.5 |
| PS/DBBF | 33 | −0.0491 | 43.2 |
| PS/PEGHb | >120 | | >120 |

As previously indicated, blood products comprising pentastarch (e.g., PENTASPAN®) and PEGHb optimize viscosity, oncotic pressure, oxygen affinity and oxygen capacity. Of the products listed in Table 14, only PEGHb has all of these properties. Diluting PEGHb with a different non-oxygen-carrying component (e.g., the plasma expander hetastarch) would reduce the resulting blood product's viscosity and oncotic pressure, not change the oxygen affinity, but reduce the oxygen capacity. In contrast, the mixtures resulting from combination of PEG-modified hemoglobin with pentastarch have viscosity and oncotic pressure values very close to that of PEGHb alone.

The examples that follow compare several different blood product mixtures and solutions and summarize the physiological data generated from each set of experiments. The data indicate that preferred substitute blood products incorporate most, if not all, of the above-mentioned properties (i.e., oncotic pressure, viscosity, oxygen affinity and oxygen content).

EXAMPLE 11

Conventional Plasma Expanders

This example specifically compares animal survival and physiological data following exchange transfusions and hemorrhage with two conventional plasma expanders (i.e., non-oxygen-carrying components, hetastarch (HS) and pentastarch (PS) (see Table 14)). The experiments were performed as described in Example 10.

Product Characteristics

Hetastarch is commercially available from Fresenius, and pentastarch was commercially obtained from DuPont Merck. Both products comprise hydroxyethyl starch, but pentastarch's low molecular weight (250,000 Da vs 480,000 Da) is a result of a lower degree of hydroxyethyl substitution (0.45 compared to 0.70). This difference results in higher oncotic pressure for pentastarch and its faster enzymatic degradation in the circulation. Because of its higher oncotic pressure, pentastarch has a greater plasma expanding capability.

Animal Survival

Overall animal survival for the two groups of test animals (pentastarch and hetastarch) and control animals are set forth in Table 15, supra. The data are consistent with the hemodynamic, oxygen transport, and acid-base data. That is, survival in the pentastarch animals is significantly longer than that of the hetastarch animals, but both are shorter than the controls.

Hematocrit and Hemoglobin

Tables 16, 17, and 18 indicate hematocrit, total hemoglobin, and plasma hemoglobin, respectively. In Tables 16–18, "n"=the number of animals in the experiment, "ND"=not determined, "post ET"=immediately following the exchange transfusion, and "60 min"=following the 60 minute hemorrhage.

TABLE 16

Hematocrit

| Solution | n | Baseline | Post ET | 60 Min. |
|---|---|---|---|---|
| Control | 7 | 38.6 ± 0.9 | | 24.8 ± 0.9 |
| PS | 4 | 42.6 ± 1.3 | 18.4 1.0 | 15.0 ± 0.7 |
| LHS | 2 | 4.0 ± 1.2 | 18.3 1.8 | 12.7 ± |
| DBBF | 6 | 39.5 ± 0.7 | 18.5 0.4 | 13.4 ± 0.6 |
| TM | 6 | 42.4 ± 0.9 | 21.8 0.5 | *13.9 ± 0.2 |
| B82 | 4 | 2.7 ± 1.3 | 18.3 1.0 | 14.4 ± 0.6 |
| HL | 4 | 40.7 ± 1.2 | 18.1 1.3 | 12.2 ± 0.8 |
| PEG | 5 | 40.5 ± 1.2 | 15.8 0.4 | 12.9 ± 0.2 |
| Bovine | 1 | 40.0 | 22.0 | #18.2 |
| PS/DBBF | 5 | 40.3 ± 1.1 | 22.2 2.3 | *17.1 ± 2.0 |
| PS/HL | 5 | 43.3 ± 0.9 | 20.2 0.6 | 15.0 ± 1.0 |
| HS/HL | 4 | 40.5 ± 0.4 | 19.0 0.1 | 13.1 ± 0.3 |
| PS/PEG | 2 | 40.2 ± 0.8 | 14.8 0.4 | 12.6 ± 0.4 |

*50 minute sample.
30 minute sample.

TABLE 17

Total Hemoglobin

| Solution | n | Baseline | Post ET | 60 Min. |
|---|---|---|---|---|
| Control | 7 | 13.8 ± 0.3 | | 8.8 ± 0.3 |
| PS | 4 | 15.2 ± 0.4 | 6.8 ± 0.4 | 5.4 ± 0.3 |
| HS | 2 | 14.1 ± 0.9 | 6.6 ± 0.5 | 4.2± |
| DBBF | 6 | 14.0 ± 0.3 | 10.2 ± 0.2 | 7.2 ± 0.4 |
| TM | 6 | 14.8 ± 0.3 | 10.9 ± 0.3 | *74 0.4 |
| B82 | 4 | 14.7 0.4 | 9.2 0.3 | 7.5 0.4 |
| HL | 5 | 14.2 0.2 | 10.8 0.2 | 7.8 0.1 |
| PEG | 5 | 14.5 ± 0.6 | 7.6 0.1 | 6.4 0.1 |
| Bovine | 1 | 14.0 | 9.9 | #8 |
| PS/DBBF | 5 | 13.9 ± 0.4 | 9.1 0.7 | *7.1 ± 0.3 |
| PS/HL | 5 | 13.9 ± 1.5 | 8.8 ± 0.4 | 6.0 ± 0.1 |
| HS/HL | 4 | 14.4 ± 0.2 | 8.6 ± 0.1 | 6.0 ± 0.1 |
| PS/PEG | 2 | 14.0 ± 0.2 | 5.6 0.2 | 5.0 0.2 |

*50 minute sample.
30 minute sample.

TABLE 18

Plasma Hemoglobin

| Solution | n | Baseline | Post ET | 60 Min. |
|---|---|---|---|---|
| Control | 6 | No | 3.9 ± 0.1 | 2.3 ± 0.1 |
| PS | 6 | No | 3.7 0.2 | *2.2 0.1 |
| HS | 4 | No | 3.6 0.2 | 2.4 0.1 |
| DBBF | 4 | No | 4.8 ± 0.1 | 2.6 ± 0.3 |
| TM | 5 | No | 1.9 0.1 | 1.5 0.1 |
| B82 | 5 | No | 1.6 ± 0.4 | *1.3 ± 0.2 |
| PS/HL | 5 | No | 2.1 ± 0.4 | 1.1 ± 0.3 |
| PS/PEG | 2 | No | 1.0 0.0 | 0.8 0.0 |
| Bovine | 1 | No | 2.5 | #1.9 |

The data in Table 16 indicate that both pentastarch and hetastarch hemodilute to a similar degree, as measured by post-exchange hematocrit. However, the hematocrit in the hetastarch animals was significantly lower than in the pentastarch animals after the 60% hemorrhage. Similarly, Table 17 shows that the total hemoglobins were similar in both groups of animals after hemodilution, but the hetastarch animals had significantly lower hemoglobin after the hemorrhage.

Hemodynamics

Compared to controls, both pentastarch- and hetastarch-hemodiluted groups dropped their blood pressure very rapidly after start of the hemorrhage (data not shown). Recovery was faster in the pentastarch animals and was sustained better than in the hetastarch group, but both have significantly lower blood pressure than the controls after the first 40 minutes of hemorrhage.

Both hetastarch and pentastarch groups increased their heart rates in response to the volume loss, but the rise in the hetastarch group was more abrupt than in the pentastarch or control groups (data not shown). Though the practice of the present invention does not require an understanding of this effect, it is most likely due to the more significant plasma volume expansion expected after exchanging with the hyper-oncotic pentastarch. Both test groups raised their blood pressure sooner than the controls during the hemorrhage, probably because of the significantly lower hemoglobin and hematocrit in the exchanged animals.

The parameter dP/dt represents the maximum positive slope of the pulse pressure contour. This parameter is proportional to the onset of the systolic contraction, and is therefore a reflection of the strength, or inotropic action of the heart. In the control animals, dP/dt rose after onset of hemorrhage, as the heart attempts to increase its output. The dP/dt value rose in all three groups, but sooner in the hetastarch group compared to pentastarch group and controls (data not shown). The increase in dP/dt in the pentastarch group was actually very similar to that seen in the controls, suggesting that the plasma volume expansion of the pentastarch animals was beneficial.

Ventilation

Ventilation is reflected by $PO_2$ and $PCO_2$ measurements. The rise in $PO_2$ and fall in $PCO_2$ (data not shown) was more pronounced in the hetastarch animals compared to the pentastarch animals, but both were more significant than in the controls. This is a reflection of compromise in oxygen delivery during hemorrhage in the rank hetastarch>pentastarch>Control. Though the practice of the present invention does not require an understanding of the mechanism, it is probable that both starch products reduce the hemoglobin significantly compared to the control, explaining why both seem to stress the animals more than the controls. Of pentastarch and hetastarch, however, pentastarch affords better compensation to hemorrhage, most likely because of its better plasma expanding ability.

Acid-Base Balance and Lactic Acid

Regarding pH and base excess, the most significant compromise during hemorrhage was seen in the hetastarch animals, which exhibited dramatic drops in pH and base excess (data not shown). The pentastarch animals were slightly more compromised compared to controls. It is noteworthy that the controls actually seemed to compensate fairly adequately to the 60% hemorrhage; specifically, although $PCO_2$ fell and base excess became more negative, the animals were able to maintain their pH essentially constant.

Lactic acid is an accurate indicator of tissue oxygenation. The lactic acid accumulation in the hetastarch animals was significantly greater than in the pentastarch animals, and both groups accumulated more lactic acid than the controls (data now shown). Of note, the lactic acid level plateaued in the controls, suggesting that the rate of production and clearance is equal, another indication of adequate compensation to the hemorrhage.

The results of this example show that in the exchange-transfusion/hemorrhage model utilized, all of the control animals were dead by approximately 130 minutes after start of the hemorrhage. Thus, any perturbation in the oxygen transport system was reflected in a number of measured variables. The results indicate that neither pentastarch or hetastarch was able to compensate for loss of half of the circulating blood volume. However, comparison of the two plasma expanders reveals that pentastarch is clearly superior to hetastarch. Though the rationale for this finding is not required in order to practice the invention, it is believed to be due to the higher oncotic pressure of pentastarch, which thus affords more significant plasma volume expansion in the pentastarch animals compared to the hetastarch group.

EXAMPLE 12

Blood Product Mixtures of Pentastarch and DBBF

This example specifically compares animal survival and physiological data following exchange transfusions and hemorrhage with a blood product mixture (50:50) of pentastarch and DBBF ($\alpha\alpha$-Hb). The experiments were performed as described in Example 10.

Animal Survival

Figure 11:
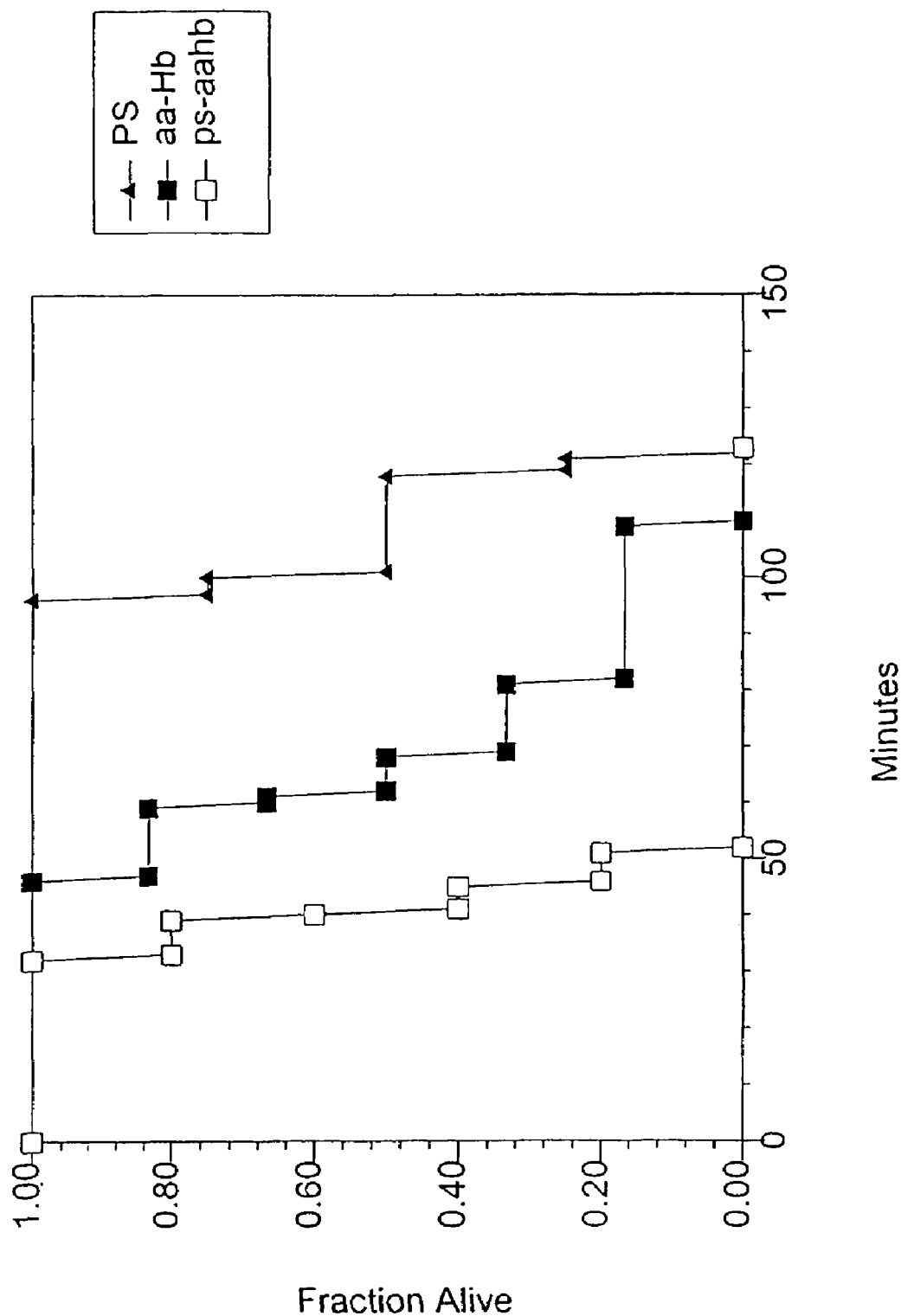
FIG. 11 depicts animal survival following exchange transfusion with pentastarch (▲), αα-Hb (■), and pentastarch+αα-Hb (□) after the initiation of a 60% hemorrhage.

Animal survival of the control animals, pentastarch (PS) alone animals, DBBF ($\alpha\alpha$ hemoglobin) alone animals, and animals administered a pentastarch+$\alpha\alpha$-Hb mixture is shown in FIG. 11. Referring to FIG. 11, (▲) represents pentastarch, (■) represents $\alpha\alpha$-Hb, and (□) represents pentastarch+$\alpha\alpha$-Hb. As indicated in FIG. 11, survival of the $\alpha\alpha$-Hb animals is significantly worse than either the controls or the pentastarch animals, and a mixture of 50/50 $\alpha\alpha$-Hb and pentastarch is even worse. It should also be noted that there was no obvious relationship between survival and hematocrit (see Table 16, supra) or hemoglobin (see Table 17, supra), so survival does not appear to be a linear function of the oxygen carried in the blood.

Mean Arterial Pressure

Mean arterial pressure rose in the PS/$\alpha\alpha$-Hb animals and the $\alpha\alpha$-Hb animals (data not shown). Moreover, even though hemoglobin dose was half in the PS/$\alpha\alpha$-Hb animals, the magnitude of the blood pressure rise was the same. Thus, the presence of PS did not attenuate the hemoglobin-induced hypertension of approximately 20 mm Hg. The fall in blood pressure, however, after starting the hemorrhage, was more abrupt in the PS/$\alpha\alpha$-Hb animals than in any of the other 3 groups. The recovery was somewhat faster, possibly due to the plasma expansion afforded by the presence of pentastarch. Nevertheless, when blood pressure began to fall terminally, it fell very fast, and animals rapidly died. Thus, the rise in blood pressure resulting from the presence of $\alpha\alpha$-Hb hemoglobin does not appear to confer any advantage, and the presence of PS does not attenuate this effect.

Heart Rate

In control animals, heart rate gradually increased after start of the hemorrhage (data not shown). Though the present invention does not require an understanding of the underlying mechanism of this effect, it is most likely due to loss of intravascular volume. This interpretation is supported by the somewhat lower heart rate response seen in the pentastarch animals who, in spite of a lower hemoglobin concentration, did not raise their heart rate to the same degree (data not shown). A different pattern of heart rate response was seen in the $\alpha\alpha$-Hb animals; more specifically, there was an immediate drop in heart rate after starting the exchange transfusion, followed by a gradual rise after starting the hemorrhage (data not shown). The drop cannot be explained by volume changes, since a contraction of the plasma volume would be expected to raise the heart rate, not lower it. More likely, this a direct chronotropic effect on the myocardium. Of note, this depressant effect is lessened when the $\alpha\alpha$-Hb is diluted with pentastarch (data not shown). The PS/$\alpha\alpha$-Hb animals exhibited a brisk rise in heart rate after starting hemorrhage, rapidly reaching approximately 500/min, a rate not reached in the other groups until a later time. Thus, the PS/$\alpha\alpha$-Hb mixture did not seem to offer any advantage over $\alpha\alpha$-Hb alone.

dP/dt

As previously set forth, the dP/dt is the maximum positive slope of the pulse pressure contour. This parameter is proportional to the onset of the systolic contraction, and is therefore a reflection of the strength, or inotropic action of the heart. In the control animals, dP/dt rose after onset of hemorrhage (data not shown). The pentastarch animals showed the same pattern, although the magnitude of the response was less, presumably because these animals had a somewhat increased vascular volume compared to the controls at the onset of hemorrhage. The $\alpha\alpha$-Hb animals never increased their dP/dt (data not shown); in fact, the value dropped rapidly after the onset of hemorrhage, suggesting that one of the normal compensatory mechanisms is disordered. The same observation was made in the PS/$\alpha\alpha$-Hb animals, even though they were expected to have a somewhat greater vascular volume than the $\alpha\alpha$-Hb animals by virtue of the presence of oncotically-active pentastarch.

Ventilation

When oxygen transport is diminished, either because of anemia or hypoxia, a normal physiologic response is to hyperventilate. The result of hyperventilation is a drop in $PCO_2$, since the elimination of $CO_2$ by the lung is a direct function of ventilation. A reciprocal effect is increased $PO_2$, again, because of the greater minute volume of gas being exchanged by the lung. In the control animals, $PCO_2$ dropped after the onset of hemorrhage (data not shown); by comparison, the pentastarch animals also lowered their $PCO_2$ (data not shown), but the effect persisted for a longer period of time and appeared to be more pronounced, probably as a result of the lower hemoglobin concentration in the pentastarch animals compared to the controls. (See Table 17). The $PCO_2$ drop was significantly greater in the $\alpha\alpha$-Hb animals, and still greater in the PS/$\alpha\alpha$-Hb animals. Comparison of the $\alpha\alpha$-Hb and PS/$\alpha\alpha$-Hb animals is interesting, since the former has a higher total hemoglobin concentration, but a lower blood volume. Thus, the addition of PS to the $\alpha\alpha$-Hb did not confer any advantage on the animals and, in fact, appears to have induced greater hyperventilation.

The $PO_2$ changes are the mirror image of the $PCO_2$ response; the greatest rise in $PO_2$ (and drop in $PCO_2$) was seen in the $\alpha\alpha$-Hb and PS/$\alpha\alpha$-Hb animals, while the controls and pentastarch animals had the smallest increase in $PO_2$ (data not shown). Thus, the data are consistent with the belief that reduced oxygen delivery leads to hyperventilation, and the degree of hyperventilation correlates with overall survival.

Acid-Base Status

As hemorrhage progresses and the delivery of oxygen to tissues becomes compromised, lactic acid is produced and pH drops. For the control animals, pH was maintained nearly constant as hemorrhage progressed. Another index of the degree of compensation is the base excess, which is defined as the amount of base that would be required to return plasma pH to 7.4 in the presence of a $PCO_2$ of 40 Torr. in the case of both the controls and PS animals, base excess was not significantly changed from baseline (data not shown). In contrast, $\alpha\alpha$-Hb and, especially, PS/$\alpha\alpha$-Hb produced a marked drop in pH which is not compensated by the brisk hyperventilation (data not shown), and the result was a dramatic drop in base excess (ie., a "base deficit" results). By usual clinical standards, a base excess of −10 mEq/L or less is indicative of poor recovery from hemorrhagic shock.

Finally, lactic acid is a direct measure of the degree of insufficient delivery of oxygen to tissues (i.e., the "oxygen debt"). The accumulation of lactic acid was very significant in both the αα-Hb and PS/αα-Hb animals, the latter rising even more sharply than the former (data not shown). It is also of interest that in the controls and pentastarch animals, there was a rather more modest rise in lactate which then seemed to plateau, as the animals' compensatory mechanisms (increased cardiac output, ventilation) seemed to compensate for the blood loss. However, the continued linear rise of lactic acid in both the αα-Hb and PS/αα-Hb animals indicated progressive, uncontrolled tissue acidosis.

The results discussed above indicate that the use of blood product mixtures comprising αα-Hb as the oxygen-carrying component, even though it provides some plasma hemoglobin, rendered the animals in a more vulnerable position with regard to hemorrhage than either the controls or the animals hemodiluted with pentastarch. The addition of pentastarch to αα-Hb did not compensate for the detrimental effects of αα-Hb and, in fact, worsened oxygen delivery, acidosis and overall survival.

EXAMPLE 13

Blood Product Mixtures of HEMOLINK®/Pentastarch and HEMOLINK®/Hetastarch

Example 8 compared the effects of pentastarch, HEMOLINK®, and a mixture thereof. This example compares a mixture of HEMOLINK®/pentastarch with a mixture of HEMOLINK® and another non-oxygen-carrying component, hetastarch. The experiments of this example, performed as described in Example 10, specifically compare animal survival and physiological data following exchange transfusions and hemorrhage.

As previously indicated, HEMOLINK® (Hemosol) is a polymerized human hemoglobin that has a mean molecular weight of approximately 128,000 Da. Since HEMOLINK® is a polymerized product, an array of molecular sizes is present in the final product. When tested alone, hemodilution with HEMOLINK® did not perform as well as pentastarch, and animals died sooner than those in the control or pentastarch groups. (See, e.g., Example 8). In view of the surprising and positive results with a mixture of pentastarch and PEGHb, additional experiments involving mixtures (50/50) of HEMOLINK® and a non-oxygen-carrying components (hetastarch or pentastarch) were performed in this example.

Figure 12:
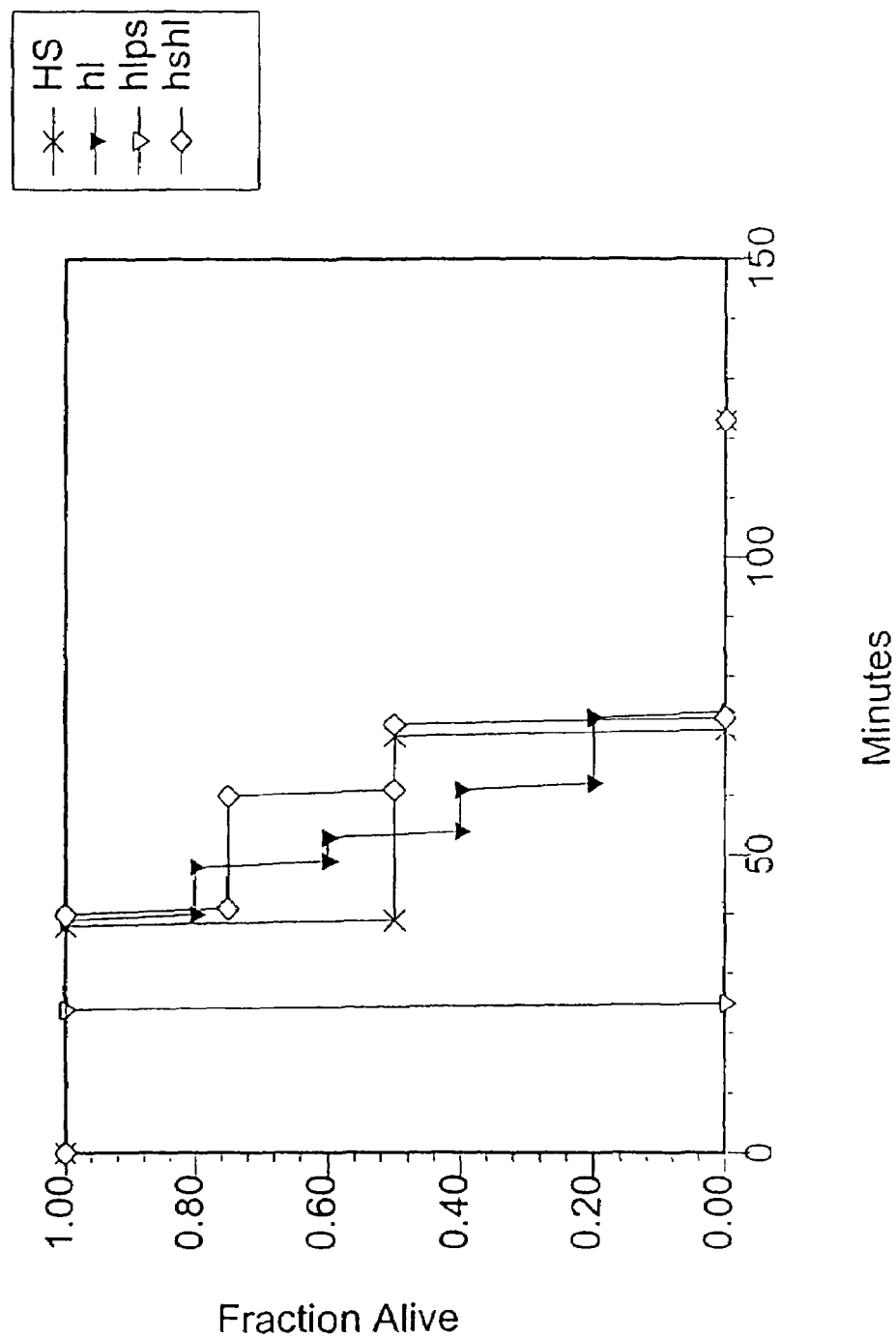
FIG. 12 depicts animal survival following exchange transfusion with hetastarch (×), HEMOLINK®(▼), HEMOLINK®+pentastarch (∇), and hetastarch+HEMOLINK®(◇) and after the initiation of a 60% hemorrhage.

As shown in FIG. 12, exchange transfusion with HEMOLINK® alone reduced survival from a 60% hemorrhage. More specifically, FIG. 12 depicts animal survival following exchange transfusion with hetastarch (x), HEMOLINK® (□), HEMOLINK®+pentastarch (□), and hetastarch+HEMOLINK® (◊) and after the initiation of a 60% hemorrhage.

Mean Arterial Pressure

Exchange transfusion with HEMOLINK® raised mean arterial blood pressure slightly (data not shown), but not as significantly as DBBF (αα-Hb) (Example 12). When the arterial hemorrhage was begun, blood pressure in all four groups (i.e., HEMOLINK® alone; HEMOLINK®/pentastarch; HEMOLINK®/hetastarch; and control) of animals fell abruptly (data not shown). The degree of initial fall in blood pressure was greatest in the HEMOLINK®/hetastarch group (120 to 50 mm Hg) compared to 110 to 80 mm Hg for the controls, 120 to 90 mm Hg for the HEMOLINK®/pentastarch animals, and 120 to 80 mm Hg for the HEMOLINK® alone animals. Thus, as judged by the fall in blood pressure and overall survival, the HEMOLINK®/hetastarch animals, HEMOLINK®, and HEMOLINK®/PENTASPAN® animals (in that order) all seemed to be worse than the controls. Nevertheless, overall survival for the HEMOLINK®/hetastarch and HEMOLINK®/PENTASPAN® animals was not different (Table 15, supra) and only marginally better than the HEMOLINK® alone animals.

The HEMOLINK® and HEMOLINK®/PENTASPAN® animals both raised their heart rates in response to the hemorrhage, but the rise was earlier and steeper than in the controls (data not shown); this indicates less cardiovascular stability in the exchange-transfused animals compared to the controls. Surprisingly, the HEMOLINK®/hetastarch animals dropped heart rate abruptly after starting the hemorrhage; this abnormal response might have indicated severe compromise in these animals compared to the other groups.

An increase in dP/dt was observed in the HEMOLINK® animals after exchange transfusion compared to the controls (data not shown), indicating that the exchange by itself conferred instability on the cardiovascular system. The pentastarch/HEMOLINK® animals demonstrated little, if any, increase in dP/dt, whereas the response in the hetastarch/HEMOLINK® animals was striking, increasing abruptly after initiating the hemorrhage, reaching a peak value of nearly 2000 mm Hg/sec, and then rapidly falling as animals became severely compromised and died (data not shown).

Ventilation and Acid Base Status

The rise in $PO_2$ and fall in $PCO_2$ observed in each of the three experimental groups was greater than the control values, but no distinction can be made between those groups (data not shown).

All experimental groups demonstrates lower pH during the hemorrhage than the control group. The acid-base disturbance was more clearly shown in the base excess, as all three experimental groups become severely acidotic (negative base excess) beginning abruptly after start of the hemorrhage. Finally, lactic acid increase was very significant in all three experimental groups, again confirming the presence of severe acidosis (data not shown).

Previously it was shown that HEMOLINK® did not perform as well as the controls or as well as pentastarch alone; moreover, HEMOLINK® alone and hetastarch alone performed comparably, but neither afforded as much protection as pentastarch alone. As set forth in this example, attempts to improve the performance of HEMOLINK® by mixing it with either pentastarch or hetastarch did not improve the results.

EXAMPLE 14

Blood Product Mixtures of TM Hemoglobin/Pentastarch

This example specifically compares animal survival and physiological data following exchange transfusions and hemorrhage with a blood product mixture (50:50) of pentastarch and TM hemoglobin; trimesic acid (TM) is used to crosslink hemoglobin. The experiments were performed as described in Example 10.

Animal Survival

TM hemoglobin (Hemosol) is a human-hemoglobin derived product of molecular weight approximately 64,000 Da. It has a relatively low oxygen affinity ($P_{50}$ about 35 Torr). Studies using TM hemoglobin alone were not significantly different from those with DBBF (αα-Hb) alone. (See Example 12). All animals that received TM hemoglobin alone or in combination with pentastarch died within 60 minutes after start of hemorrhage (only one animal was tested using a mixture of TM hemoglobin and pentastarch, and it died at 60 minutes following initiation of hemorrhage).

Mean Arterial Pressure, Heart Rate and dP/dt

Exchange transfusion resulted in a moderate rise in mean arterial blood pressure of the single animal tested using TM hemoglobin/pentastarch. Pressure abruptly fell after start of the hemorrhage, but then recovered rather quickly; however as the hemorrhage progressed, when the mean arterial pressure began to fall again, the animal died very suddenly (data not shown).

There was a slight fall in heart rate after the exchange transfusion with either TM hemoglobin or the TM hemoglobin/pentastarch mixture. After a delay of about 20 minutes, the heart rate rose during hemorrhage in both groups.

Regarding the dP/dt, in contrast to many of the other hemoglobin preparations, TM hemoglobin/pentastarch or TM hemoglobin alone did not lead to an increase in dP/dt. Rather, a steady fall occurred starting after the hemorrhage was initiated (data not shown).

Ventilation and Acid-Base Status

As noted in previous examples, $PO_2$ and $PCO_2$ change in mirror image, reflecting the hyperventilation that accompanies diminished oxygen transport as hemorrhage progresses. The rise in $PO_2$ and fall in $PCO_2$ observed in both of the experimental groups was greater than the control values (no distinction can be made between those groups; data not shown).

In regards to arterial pH acid and base, both experimental groups demonstrated lower pH during the hemorrhage than the control group; base excess determinations showed that both experimental groups became severely acidotic (negative base excess) beginning abruptly after start of the hemorrhage (data not shown). Finally, lactic acid increase was very significant in both experimental groups (data not shown), again confirming the presence of severe acidosis.

As previously indicated (see Table 15), TM hemoglobin did not perform as well as the controls or as well as pentastarch. TM hemoglobin and pentastarch/TM hemoglobin performed comparably, but neither afforded as much protection as pentastarch alone. The attempts to improve the performance of TM hemoglobin by mixing it with pentastarch, reported in this example, did not improve the results. TM hemoglobin has a low $O_2$ affinity compared to other hemoglobin derivatives studied, and the results reported above indicate that this low affinity did not confer advantage over other cross-linked hemoglobins whose other physical properties are the same (e.g., DBBF).

EXAMPLE 15

Modified Hemoglobins

As set forth above, mixtures of polyethylene glycol-modified bovine hemoglobin and pentastarch lead to increased animal survival when compared to mixtures comprising other non-oxygen-carrying components. In order to determine whether these results were due to the mixture or to the bovine hemoglobin itself, an experiment was performed evaluating purified bovine hemoglobin. In addition, experiments were performed with β82 Hemoglobin, a product which has a high oxygen affinity, to determine whether this product alone might be superior to the mixtures of an oxygen-carrying component and a non-oxygen-carrying component contemplated for use with the present invention. As with the previous examples, the experiments of this example specifically compare animal survival and physiological data following exchange transfusions and hemorrhage using the experimental protocol described in Example 10.

Bovine Hemoglobin

Briefly, when the animal was exchange-transfused with bovine hemoglobin, there was only a transient rise in mean arterial blood pressure, followed by a steady fall (data not shown). When the hemorrhage started, mean arterial pressure fell precipitously, and the animal died approximately 30 minutes after start of the hemorrhage (data not shown).

The heart rate in this animal did not rise significantly when hemorrhage started but there was a modest rise terminally, a few minutes before the animal died. The dP/dt remained constant, in contrast to controls in which this parameter always rose in response to hemorrhage. Finally, regarding pH and acid-base status, the animal severely hyperventilated, as indicated by a rise in $PO_2$ and a drop in $PCO_2$. Accordingly, there was a very precipitous fall in pH and base excess and a sharp rise in lactic acid (data not shown).

β82 Hemoglobin

82 Hemoglobin (Hemosol) is a derivative of human hemoglobin that is crosslinked between the β chains (in contrast to DBBF [αα-Hb]). This product has high oxygen affinity, but low viscosity and oncotic pressure.

When animals were exchange-transfused with β82 Hemoglobin, there was a very transient, but pronounced, rise in blood pressure; the magnitude of the rise was approximately the same as that seen with αα-Hb, but the mean arterial pressure rapidly returned to the pre-infusion level (data not shown). When hemorrhage began, blood pressure rapidly fell, and animals died by approximately 70 minutes. Thus, overall survival was not better than αα-Hb hemoglobin, and less than either the controls or the pentastarch animals.

Heart rate did not rise significantly either after exchange or after hemorrhage, nor did dP/dt. The animals did have pronounced hyperventilation (increase in $PO_2$ and fall in $PCO_2$). Severe acidosis was shown by a dramatic drop in pH, base excess, and rise in lactic acid (data not shown).

Thus, the experiments with the modified hemoglobin products of this example did not lead to superior results than those obtained when mixtures of PENTASPAN® and PEGHb were employed.

EXAMPLE 16

Evaluation of Various Hemoglobin Solutions

In this Example, three hemoglobin solutions were evaluated (See, Table 19), including: 1) Purified human hemoglobin $A_o$ (Hb-$A_o$); 2) αα-hemoglobin, human hemoglobin cross-linked with bis(3,5-dibromo salicyl)fumarate; 3) PEG-hemoglobin, bovine hemoglobin surface-modified with polyethylene glycol. The PEG units have a molecular weight of 5,000 Da.

Human red blood cells were drawn from healthy volunteers into heparin anticoagulant, washed 3 times in 0.9% NaCl by gentle centrifugation, and resuspended in 0.1 M Bis-tris Cl buffer, pH 7.4. The hemoglobin concentration of all solutions and red cell suspensions was approximately 3 mM (heme). The methemoglobin was always less than 2–4% of total hemoglobin. The test solutions were equilibrated to the appropriate gas concentrations and 37° C. using a tonometer (e.g., model 2000, Instrumentation Laboratories, Lexington, Mass.). Human serum albumin (HSA) was purchased commercially.

The test methods used included the following protocols, the results of which are shown in Table 19. While this Example provides methods to determine various characteristics of a test preparation, it is not intended that the present invention be limited to these particular protocols. Indeed, those of skill in the art know additional methods that would be suitable for making these determinations.

Oxygen Equilibrium Binding Curves:

Cell-free hemoglobin-oxygen equilibrium curves were measured by coupling diode array spectrophotometry with enzymatic deoxygenation of oxyhemoglobin solutions (Vandegriff et al., Anal. Biochem., 256:107–116 [1998]). The protocatechuic acid (PCA)/protocatechuic acid 3,4-dioxygenase (PCD) enzyme system consumes one mole of $O_2$ for each mole of PCA converted to product.

Reactions were carried out 0.1 M bis-Tris propane (Sigma), 0.1 M Cl$^-$, and 1 mM EDTA at pH 7.4 and 37° C. Hemoglobin samples were diluted to a concentration of approximately 60 μM (in heme) in air-equilibrated, temperature-equilibrated buffer containing a small amount of catalase (e.g., 0.2 to 0.5 μM). The final hemoglobin concentration was determined by the extinction coefficient at 523 nm ($\epsilon_{523}$=7.12$^{-1}$ mM). Substrate (PCA) was added at a concentration of 1 mM. A volume of this reaction solution was used to completely fill the reaction cell to eliminate any gas phase present prior to addition of enzyme. The cuvette was sealed using a gas-tight teflon stopper fitted with a micro-oxygen electrode (Microelectrodes, Inc., Londonderry, N.H.) inserted through an o-ring imbedded in the stopper. The electrode was immersed in the solution to a position just above the light path of a Milton Roy 3000 diode array spectrophotometer (SLM Instruments, Inc., Urbana, Ill.). The temperature was controlled using a Peltier controller in the reaction cell holder, and the solution was mixed using a micro-stir bar spun by a stirring motor in the reaction cell holder. The deoxygenation reaction was initiated by addition of enzyme (PCD) (0.05 to 0.1 units/ml).

The spectral change of hemoglobin during enzymatic deoxygenation was measured in the visible range from 480 to 650 nm at every ~0.35 nm. Polarographic determination of $PO_2$ was measured using a Clark-type oxygen electrode, giving a voltage change in proportion to the change in oxygen concentration. The electrode was calibrated each day by immersing the electrode in water bubbled either with air to determine the 100%-air voltage or with pure $N_2$ to set the zero point. During the hemoglobin desaturation reaction, voltages from the $O_2$ electrode were collected at a sampling rate of 10 Hz.

The spectral and $O_2$-electrode-voltage data were converted into files for analysis using the MATLAB technical-computing program (The Mathworks, Natick, Mass.). The voltage output from the $O_2$ electrode was converted to mm Hg based on the barometric pressure and the water vapor pressure at the temperature of the experiment. An average $PO_2$ value was calculated from 50 data points during each 5-second interval that corresponds in time to the collection of each spectrum.

The spectral matrix was analyzed using a multicomponent decomposition algorithm. The program returns the fractions of each base spectrum (oxy-, deoxy-, and methemoglobin) which combined from the measured spectrum being evaluated. Fractional saturation was calculated as the ratio of oxyhemoglobin to the total of oxy-plus deoxyhemoglobin. Fitted values for the Adair constants $a_1$–$a_4$) were determined by least-squares analysis with uniform weighting. Values for P50 and the Hill coefficient(n) were calculated from the fitted Adair constants (i.e., the values shown in Table 19).

Oxygen equilibrium curves for red blood cell suspensions were measured at pH 7.4 and 37° C. by the gas exchange method using a Hemox-Analyzer® (TCS Medical Products, Huntingdon Valley, Pa.).

COP

COP was measured using a Wescor 4420 colloid osmometer (Logan, Utah) with a 30,000 molecular weight cut-off membrane. The osmometer was calibrated prior to measurement of each hemoglobin sample with 5% albumin as recommended by the manufacturer. Measurements were performed at room temperature, which ranged from 20–23° C. Values reported in Table 19 are for hemoglobin concentrations of 5 g/dl.

Viscosity

Viscosity measurements are performed using a capillary viscometer (Reinhardt, 1984). The device uses the Hagen-Poiseuille law as its operating principle which defines flow (Q) in terms of capillary radius (r), pressure change along the capillary (dP/dx) and viscosity (η).

$$Q=(\pi r^4 dP)/(8\eta dx)$$

This expression can be separated into two components, the shear stress (L is the capillary length) and the shear rate, where the shear stress and rate are:

Shear Stress=$(r/2\Delta L)\Delta P$
Shear Rate=$(4/\pi r^3)Q$
Viscosity η=Shear Stress/Shear Rate Based on the geometry of the capillary, all parameters were known, except ΔP and Q. Thus, these were the two variables measured. Fluid was placed in the syringe pump (Harvard Apparatus, model 975, S. Natick, Ma.) and flow started. A differential pressure transducer (Validyne Engineering, model MP-45-14, Northridge, Calif.) was connected to the ends of a 10 cm glass capillary tube with an inside diameter of 508 μm (Vitro Dynamics, Rockway, N.J.) through a T valve. As fluid was driven through the tube, the transducer sensed the pressure at each T valve point. The transducer was arranged so that the output is the ΔP between the two T valve points. The signal was amplified (Validyne model CD12) and recorded on a strip chart.

Flow (Q) was measured by use of a calibrated flow tube. Viscosity was calculated from ΔP and Q. The capillary viscometer was both statically and dynamically calibrated, while the pressure transducer was calibrated statically with a head pressure of saline; a dynamic calibration was accomplished with water. The solutions were heated to 37° C. and placed in the viscometer. Measurements in the example used a shear rate of 160 s$^{-1}$. The values reported in Table 19 represent the measurements for hemoglobin concentrations of 5 g/dl.

TABLE 19

Properties Of The Test Solutions

|  | RBC | Ao | PEG-Hb | αα-Hb |
|---|---|---|---|---|
| $a_1$ | $1.48 \times 10^{-2}$ | $4.01 \pm 0.82 \times 10^{-2}$ | $1.47 \pm 0.39 \times 10^{-1}$ | $2.22 \pm 0.26 \times 10^{-2}$ |
| $a_2$ | $8.53 \times 10^{-4}$ | $1.74 \pm 0.44 \times 10^{-3}$ | $4.27 \pm 0.20 \times 10^{-2}$ | $9.51 \pm 0.19 \times 10^{-4}$ |
| $a_3$ | $4.95 \times 10^{-8}$ | $5.95 \pm 5.95 \times 10^{-13}$ | $2.43 \pm 1.91 \times 10^{-4}$ | $1.34 \pm 0.69 \times 10^{-11}$ |
| $a_4$ | $1.07 \times 10^{-6}$ | $2.48 \pm 0.57 \times 10^{-5}$ | $1.48 \pm 0.13 \times 10^{-4}$ | $1.05 \pm 0.13 \times 10^{-6}$ |
| P50 (mmHg) | 32.8 | 15.1 | 10.2 | 33.8 |
| n | 2.59 | 2.97 | 1.38 | 2.43 |
| viscosity (cp) (5 g/dl) | 1.4 | 0.9 | 3.4 | 0.9 |
| COP (mm Hg) (5 g/dl) | — | 14 | 79 | 11 |
| Radius (nm) | — | 2.7[1] | 14.1[1] | 3.1[1] |

[1] Vandergriff et al., Biophys. Chem., 69: 23–30 [1997].

Artificial Capillary Experiments

Figure 15:
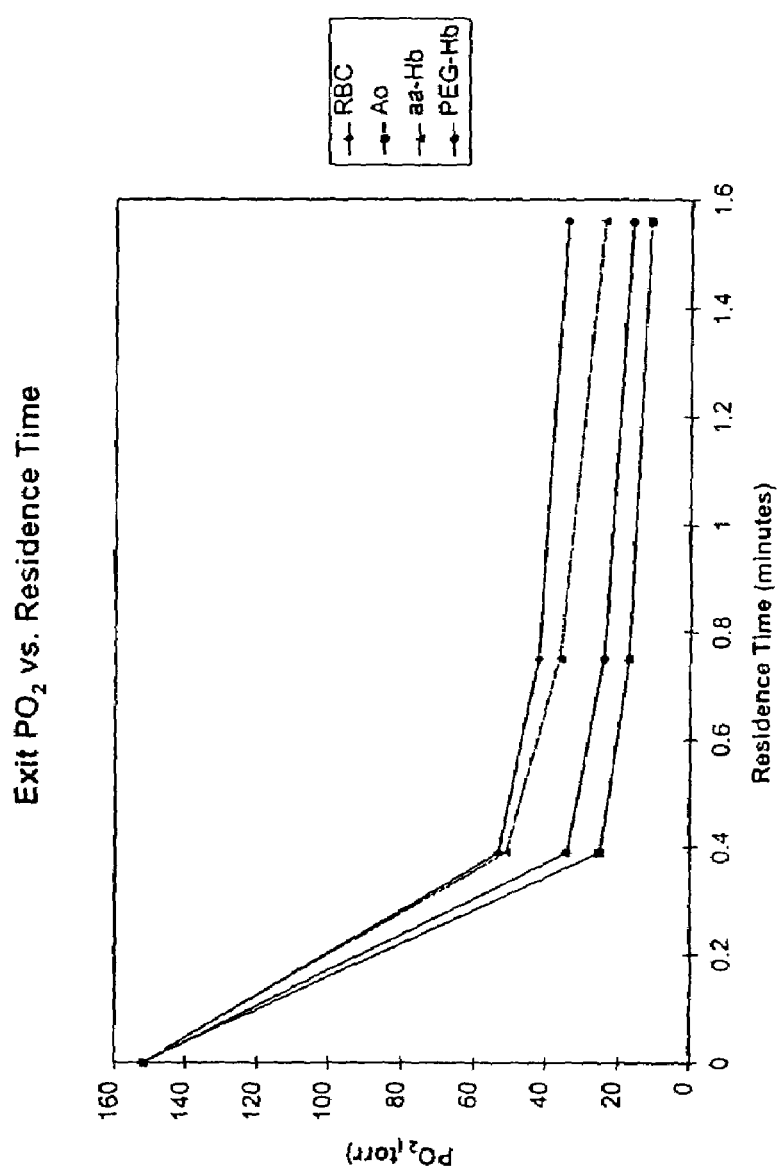
FIG. 15. is a graph showing the exit $PO_2$ compared to the residence time of red blood cells, $A_o$ hemoglobin, αα-hemoglobin, and PEG-Hb.
Figure 16:
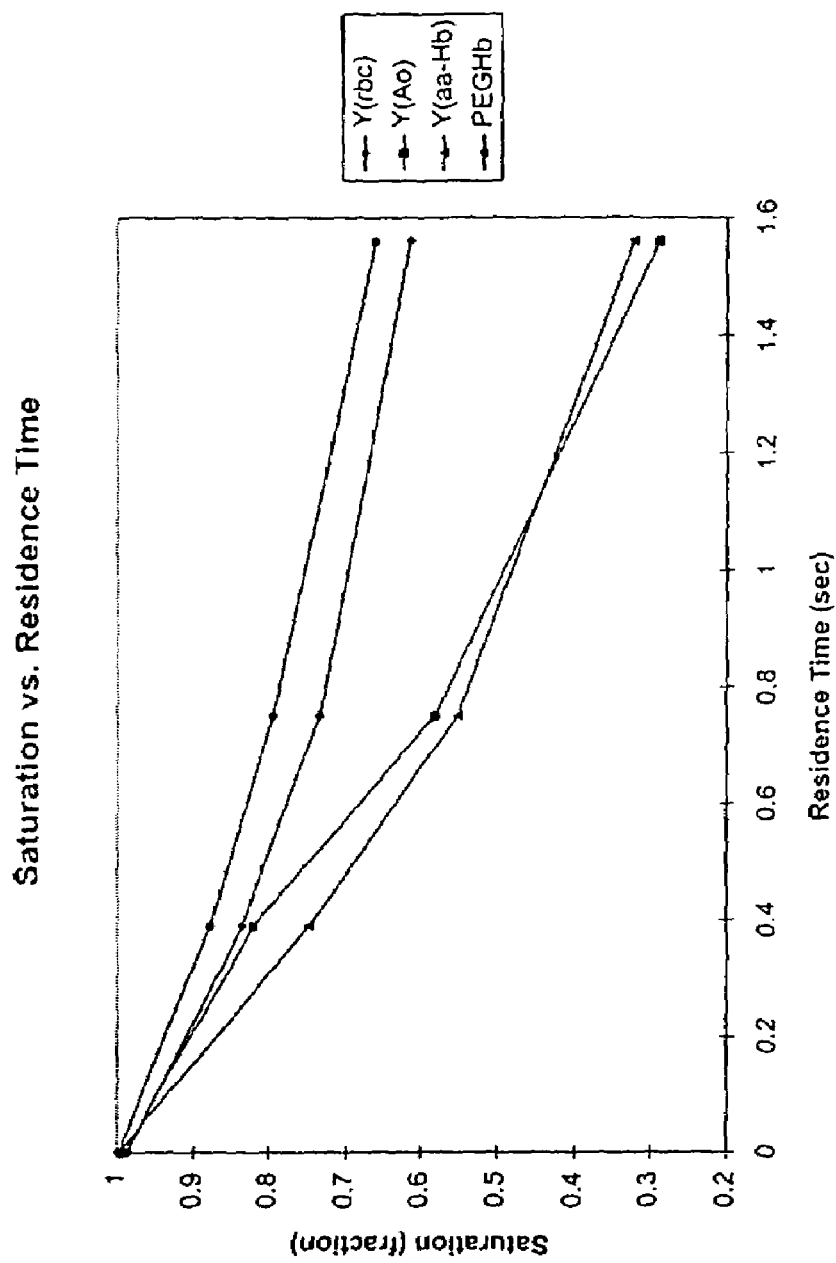
FIG. 16. is a graph showing the saturation compared with the residence time of red blood cells, $A_o$ hemoglobin, αα-hemoglobin, and PEG-Hb.

Exit PO$_2$ values versus residence times are shown in FIG. 15. At any given flow rate, the lowest exit PO$_2$ value is seen for Hb-A$_o$ followed by PEG-Hb, αα-Hb, and RBCs with the highest exit PO$_2$ values. The final saturation of hemoglobin in the artificial capillary (FIG. 6) was calculated from the Adair constants given in Table 19. PEG-Hb showed the least desaturation over time at any flow rate. This was closely paralleled by the RBC profile. Hb-A$_o$ and αα-Hb both showed much greater degrees of desaturation.

Figure 17:
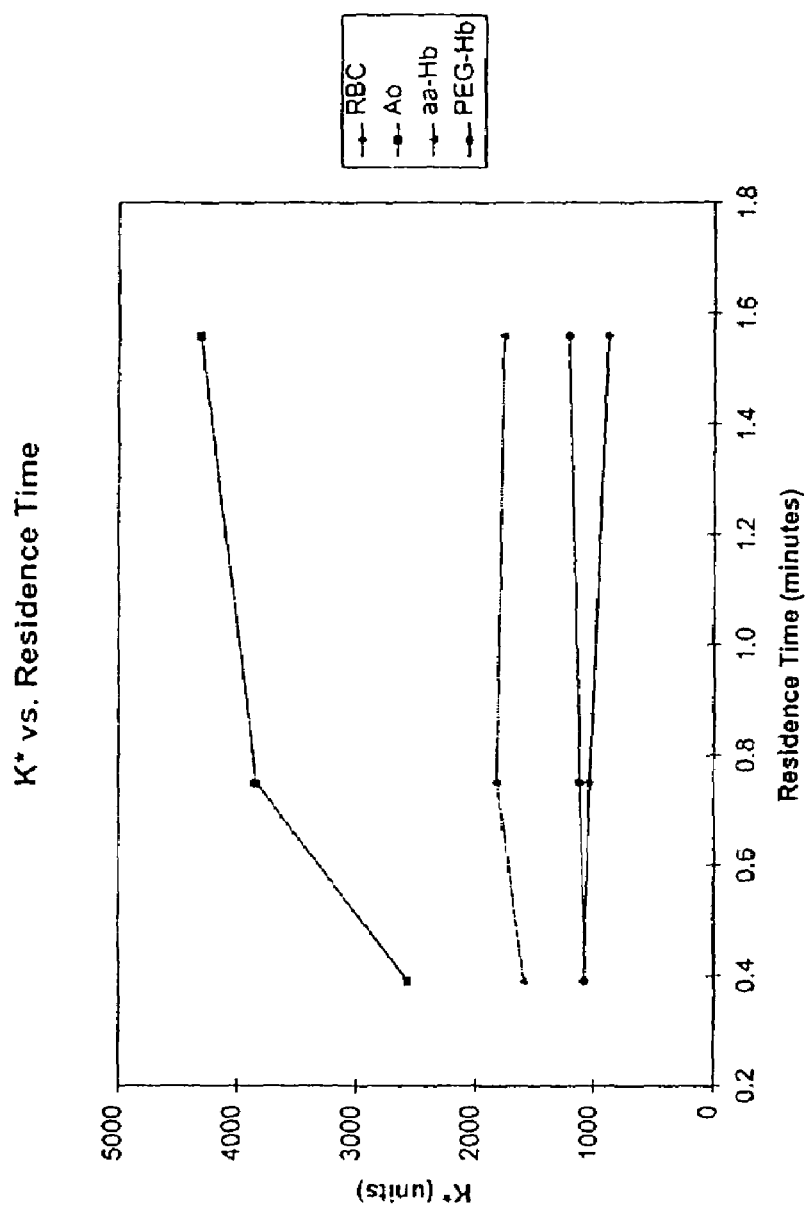
FIG. 17 is a graph showing the K* compared to the residence time of red blood cells, $A_o$ hemoglobin, αα-hemoglobin, and PEG-Hb.

The finite element analysis adjusts values for the lumped diffusion parameter, K*, until the exit PO$_2$ equals the experimental value. The final fitted values for K* as a function of residence time are shown in FIG. 17. PEG-Hb and RBCs gave similar values for K* from 900–1200 μM/min/Torr. The K* values for Hb-A$_o$ and αα-Hb are higher than for RBCs because of the absence of intraluminal resistances for cell-free solutions. This effect is negated in the cell-free PEG-Hb solution, which has a K* value equal to that for RBCs at the fastest flow rate and which is only slightly higher than RBCs at the slowest flow rate. This is due to at least two physical properties of the PEG-Hb solutions (See Equation 2, above): (1) its higher viscosity compared with the tetrameric solutions, due to its larger molecular size; and (2) its high O$_2$ affinity.

Animal Experiments

Male Sprague-Dawley rats (210–350 g, Charles River Labs) were anesthetized with 250 μl of a mixture of ketamine (71 mg/ml), acepromazine (2.85 mg/ml), and xylazine (2.85 mg/ml). Polyethylene catheters (PE-50) were placed into the abdominal aorta via the femoral artery to allow rapid withdrawal of arterial blood. A second catheter was placed in the contralateral femoral artery to monitor blood pressure, and a third catheter was placed in one of the femoral veins for infusion of test materials. Catheters were tunneled subcutaneously, exteriorized through the tail, and flushed with approximately 100 μL of normal saline. Animals were allowed to recover from the procedure and remained in their cages for 24 hours before being used in experiments. One femoral artery catheter was connected, through a stopcock, to a pressure transducer (UFI model 1050, Morro, Calif.), and arterial pressure was sampled continuously at 100 Hz using a MP100WSW data collection system (BIOPAC Systems, Inc., Goleta, Calif.). The data were stored in digital form for subsequent off-line analysis.

Figure 18:
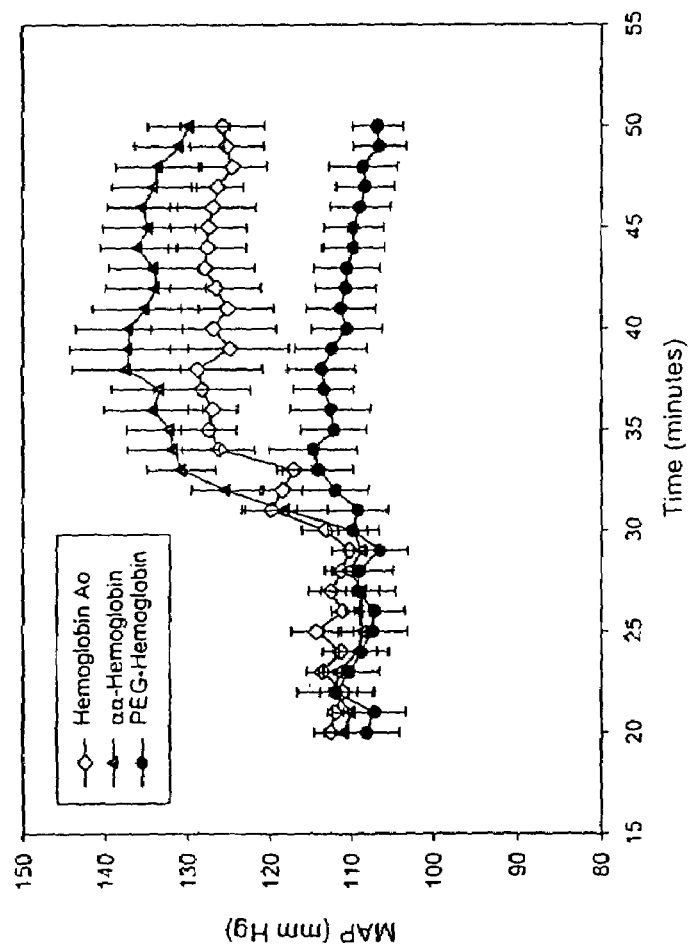
FIG. 18 is a graph showing the MAP over time for $_o$ hemoglobin, αα-hemoglobin, and PEG-Hb.
Figure 19:
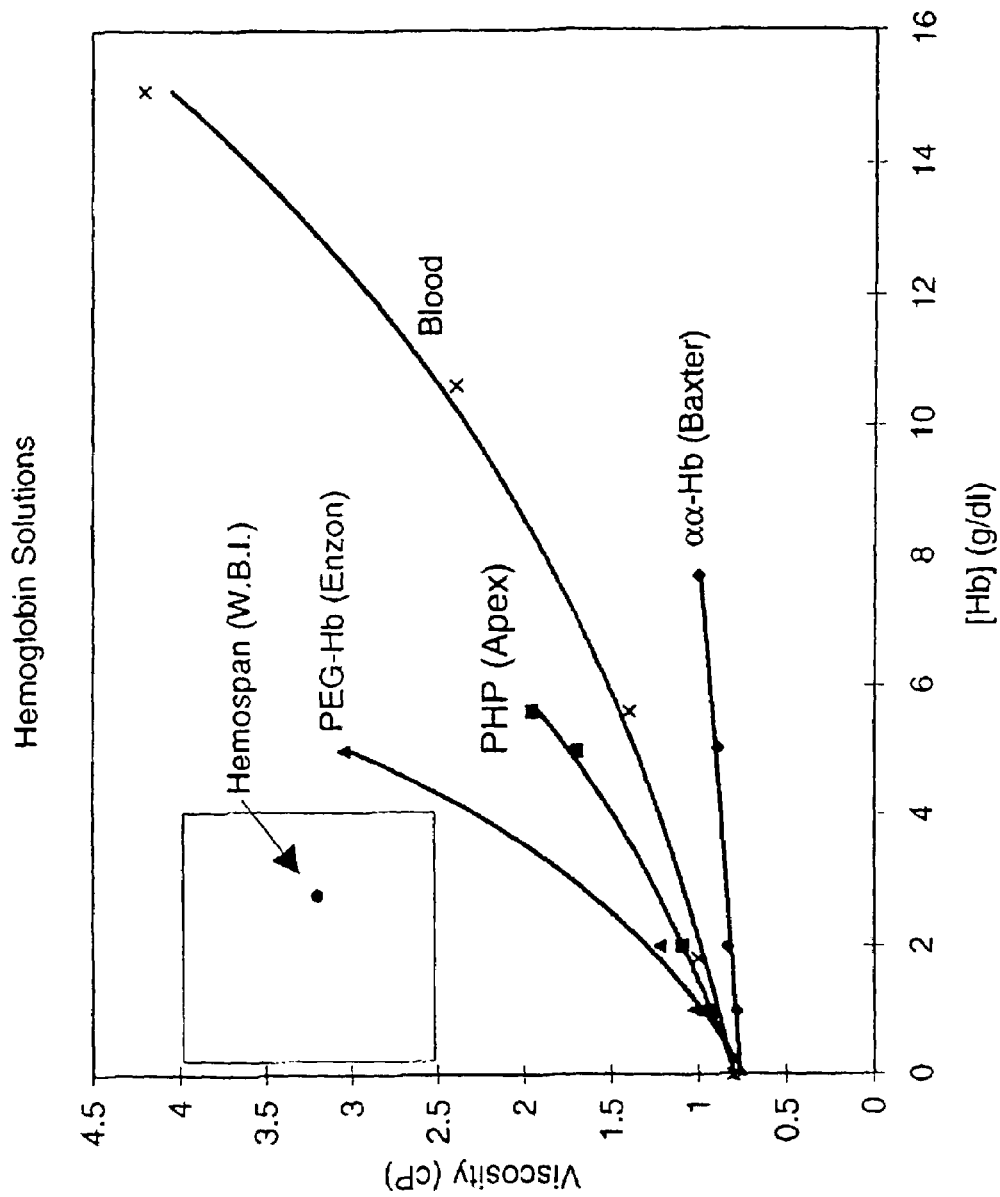
FIG. 19 is a graph showing the hemoglobin concentration and viscosity of various hemoglobin solutions.

Mean arterial pressures before and during the exchange transfusion are shown in FIG. 18. All solutions demonstrated significant vasoactivity except the PEG-hemoglobin, whose K* value is essentially identical to that of red blood cells (see FIG. 17).

Based on the data obtained in these experiments, it is contemplated that autoregulation occurs as a result of oversupply of oxygen due to facilitated diffusion by cell-free oxygen carriers. The amount of O$_2$ delivered should be the greatest for those solutions that show the greatest vasoactivity. In vivo experiments of 50% exchange transfusion in a rat are consistent with this theory in that the increase in mean arterial pressure corresponds roughly with the estimated diffusion constant, K*. Thus K* appears to be the key parameter to use to optimize the characteristics of a potential red cell substitute.

EXAMPLE 17

Other Hemoglobin Preparations

In this Example, additional hemoglobin preparations are described. These preparations may be modified to provide blood substitutes with the desirable properties of high oxygen affinity, high oncotic pressure, and relatively high viscosity (i.e., at least half that of blood).

A. Preparation of Human Hemoglobin A$_o$

In this experiment, the human hemoglobin A$_o$ of Christensen et al. (Christensen et al., J. Biochem. Biophys. Meth. 17: 143–154 [1988]) is prepared.

One unit of outdated, packed cells is washed three times in 500 ml plastic centrifuge bottles with sterile 0.9% saline. The wash solution and the buffy coat are removed with aspiration. The packed cells are mixed with 2.5 volumes of distilled water and centrifuged at 20,000×g for 1 hour. The supernatant is removed and passed through a mixed-bed ion-exchange resin (Bio-Rex RG501-X8, Bio-Rad, Richmond, Calif.) in a column. The iso-ionic effluent is passed through 0.22 µm filters (Millipore Millistack 40, Bedford, Mass.) into sterile containers.

For larger quantities of stroma-free hemoglobin: 8 units of packed cells are washed as above and hemolysis occurs in the cold, overnight. The lysate is transferred into 600 ml transfer packs (Fenwal 4B2024, Deerfield, Ill.) and spun for 6 hours at 3500×g. Approximately ⅓ of the supernatant hemoglobin solution is then removed with a plasma extractor and passed through the mixed-bed resin until the conductivity is ~15 µmhos. This process requires 1 kg of resin which is most conveniently packed into three columns. The solutions are again placed into transfer packs and centrifuged for 4 hours at 3500×g. The supernatants are filtered through a 0.22 µm disposable filter unit (Millipore Millistack, MSG05CHZ), and the filtrate is collected into sterile transfer packs and stored at 4 C for chromatography. Long-term storage is best achieved by freezing, in bulk, at −80° C.

Stroma-free hemoglobin solutions containing 10–20 g of hemoglobin are equilibrated with 0.05 M Tris-HCl at pH 8.5. This can be done as usual by dialysis or by buffer exchange and gel exclusion columns. However, since these solutions are isoionic, it is more convenient to merely dilute them with an equal volume of 0.1 M Tris-HCl at pH 8.5. Chromatography is performed with a preparative HPLC (Waters Delta-Prep 3000). The sample (~250–500 ml, 4–10 g/dl) is applied to a stainless steel column prepacked with QMA-Acell (Waters), previously equilibrated with 1–2 liters of buffer A (0.05 M Tris-HCl, pH 8.5) at a flow rate of 80 m/min. The chromatogram is developed with a linear gradient of 0.05 M Tris-HCl, pH 6.5, as the reserve (buffer B) at the same flow rate. The pH change is linear from 10% to 90% buffer B, during which all hemoglobin species are eluted. Separations are complete in 50 minutes at which time the pH of the effluent buffer is 7.2. Buffer B is the run for an additional 10 minutes to insure complete elution of the samples, and the column is re-equilibrated with 1 liter buffer A preparatory to a subsequent separation. It is possible to process up to 20 g on one column; however, this appears to be an overload. The column is purged daily with 1 liter of 0.1 M Tris-HCl, pH 7.4, in 0.1 M NaCl. On standing, it is equilibrated with 70% ethanol.

Peak detection using the preparative cell (2.1 mm pathlength) is at 510 nm and/or 600 nm. The latter wavelength is necessary for the higher concentrations and to amplify the signal due to methemoglobin. The major fraction of $Hb-A_o$ is collected to avoid the collection of methemoglobin at the leading edge and the contamination of the minor hemoglobin components at the trailing edge. The fraction is collected into a 2 liter sterile transfer pack placed in an ice bucket and transferred aseptically into a sterile 2 liter Amicon concentrator (Model 2000B, Danvers, Mass.) equipped with a TM10 membrane (10,000 Da cut-off) filter and the volume reduced to about 10% of the eluate volume at 4° C.

B. Cross-Linking Reactions to Lower P50

In this experiment, various cross-linking methods are tested for their ability to lower P50. In one experiment, the method of Walder et al. (Walder et al. Biochem., 18:4265–4270 [1979]) to produce bis(3,5-dibromosalicyl) fumarate (DBBF) and bis(3,5-dibromosalicyl) succinate (DBBS) (β82-β82) is used. Chemical modifications of human hemoglobin are carried out in 6 g/dl solutions of cell-free oxyhemoglobin in 0.05 M sodium phosphate, or in 0.05 M Bistris-HCl, pH 7.2. Incubations are for 2 hours at 37° C. in a water bath shaker. Reactions are terminated by quenching with glycine.

In another experiment, the method of Manning and Manning (Manning and Manning Biochem., 27:6640–6644 [1988]), in which hemoglobin in the R state is cross-linked with glycolaldehyde. In this experiment, the hemoglobin concentration varied from 45 to 360 µM in 50 mM potassium phosphate buffer, pH 7.3. HbCO is used. Glycolaldehyde is added to a final concentration of 50 mM. The cross-linking is performed at room temperature for 4.5 hours, and the hemoglobin derivative is then dialyzed extensively against 50 mM Tris-acetate, pH 7.3.

In yet another experiment, diisothiocyanatobenzenesulfonate (DIBS) is used to cross-link hemoglobin, according to the method of Manning et al. (Manning et al., PNAS 88:3329–3333 [1991]). Hemoglobin solutions (200 µM in the deoxygenated state, usually 3–5 µmoles) are treated with a 10-fold molar excess of the crosslinking agent DIBS. The solution is incubated at 25° C. in 0.1 M potassium phosphate, pH 7.2, for 15 min. The reaction is terminated by adding glycylglycine in 30-fold molar excess; a further incubation for 15 min. is then performed. The solution is dialyzed at 4° C. against the buffer used for the subsequent chromatographic step. The crosslinked hemoglobin (total 200–250 mg) is applied to a Whatman DE-52 column (2×30 cm) and eluted with a linear gradient of 50 mM Tris acetate from pH 8.3 to pH 6.3 (500 ml of each). For removal of the most adherent components, the column is further eluted with 500 ml of the pH 6.3 buffer. Recovery of hemoglobin from the column is 80–95%. For preparative purposes, the cross-linked hemoglobin is passed through a mixed bed resin.

In another experiment, the method of Kluger et al. (Kluger et al., Biochem., 31:7551–7559 [1992]) is used to cross-link hemoglobin with trimesoyl tris(methyl phosphate) (β82-β82). In this experiment, chemical modifications of hemoglobin are done using hemolysate diluted with 0.1 M Bis-Tris-HCl buffer at pH 7.2 to a final concentration of hemoglobin tetramer of 1 mM Hb. The final concentration of cross-linking reagent is 2 mM in 0.1 M buffer. During the initial phases of this study, the reactions are kept at 35° C. for 2–3 hours with hemoglobin in the CO form. To improve yield and to destroy any viral contaminants, the reactions are carried out at 60° C. Reagent is infused at room temperature into the 60° C. hemoglobin solution over a period of 30–60 min with a total reaction time of up to 3 hours. Reagents and low molecular weight byproducts are then removed by gel filtration with Sephadex G-25 columns.

In yet another experiment, dicarboxylic acid bis(methyl phosphates) (fumaryl & isophthalyl) (β82-β82) is used according to the method of Jones et al. (Jones et al., Biochem., 32:215–223 [1993]). Chemical modifications of hemoglobin are done using hemolysate diluted with 0.1 M bis-tris-HCl buffer at pH 7.2 to 1 mM Hb (tetramer) and cross-linking reagent at between 2 mM and 5 mM. The temperature of the reaction is either 35° C. or 60° C., and the duration of the reaction is 2–3 hours. At the higher temperature, the cross-linking reagent is added slowly by infusion over ½ to 2 hours. The reactions are run with hemoglobin in the carbon monoxide form (HbCO). The cross-linking reagents are removed by gel filtration through Sephadex G-25.

C. Hemoglobin Conjugates

In this set of experiments, hemoglobin conjugates are produced using various methods.

1. Hemoglobin Conjugated to Polyoxyethylene

First, 1 ml of a solution containing 1.0 M dibasic phosphate ($Na_2HPO_4$) and 1.0 M bicarbonate ($NaHCO_3$) are added to 10 ml of a 9 g/dl hemoglobin solution at 4° C. with gentle stirring. Then, 1 g of N-hydroxysuccinimidyl ester of methoxypoly(ethylene glycol) propionic acid, molecular weight 5,000 Da (M-SPA-5000, Shearwater Polymers, Huntsville, Ala.) is added to the solution over a 2 minute period with continued stirring. Temperature and pH are monitored throughout the reaction. Addition of the activated polyoxyethylene caused a decrease in solution pH. Approximately 10 mg amounts of solid sodium carbonate ($Na_2CO_3$) are added to the mixture to maintain the pH in the range 8.5–9.5. After 4 hours, the reaction mixture is transferred into 30,000 MW dialysis bags (Spectra/Por, Spectrum Medical Industries, Houston, Tex.) and extensively dialyzed against 0.1 M phosphate buffer, pH 7.4.

2. Hemoglobin Conjugated to Polyoxyethylene

In this experiment, the method of Leonard and Dellacherie (Leonard and Dellacherie, Biochim. Biophys. Acta 791: 219–225 [1984]) is used.

Activated polyethylene glycol, monomethoxypolyoxyethylenesuccinimidyl ester (MPSE), MW=5,000 Da, is reacted with stroma-free oxyhemoglobin. 1.5 ml of 10 g/dl hemoglobin solution are added to 2 ml 0.1 M phosphate buffer, water, or 0.1 M NaCl solution. When necessary, pH is adjusted to the desired value (5.7–7.8) by adding small amounts of 0.1 M NaOH or 0.1 M HCl. Then MPSE is added (20–30 mol MPSE per mol hemoglobin tetramer). The reaction mixtures are stirred at 6° C. for 2 hours and then analyzed by gel permeation chromatography on AcA 44 Ultrogel (linear fractionation range 10,000–130,000; exclusion limit 200,000) in 0.05 M phosphate buffer (pH 7.2) at 6° C. The reactions are considered complete when the free hemoglobin peak disappeared from the gel permeation chromatograms.

3. Hemoglobin-Polyethylene Glycol Conjugate

In this experiment, the method of Zalipsky et al. (Zalipsky et al., In Polymeric Drugs and Drug Delivery Systems (Dumm, R. L. and Ottenbrite, R. M., eds) pp. 91–100, American Chemical Society, Washington, D.C. 91–100 [1991]) is used.

A. Methoxypoly(ethylene glycol)-N-succinimidyl carbonate (SC-PEG), MW 2,000–6,000 Da (1 g, ~0.2 mmol) is added to a stirred solution of bovine oxyhemoglobin (0.1 g, ~1.5×10⁶ mol) in 0.1 M sodium phosphate buffer, pH 7.8 (60 ml). Sodium hydroxide (0.5 N) is used to maintain pH 7.8 for 30 minutes. The excess free PEG is removed by diafiltration using 50 mM phosphate buffered saline.

B. Methoxypoly(ethylene glycol)-N-succinimidyl carbonate (SC-PEG), MW 2,000–6,000 Da (1 g, ~0.2 mmol) is added to a stirred solution of bovine oxyhemoglobin (0.1 g, ~1.5×10⁻⁶ mol) in 0.1 M sodium borate buffer, pH 9.2. Sodium hydroxide (0.5 N) is used to maintain pH 9.2 for 30 minutes. The excess free PEG is removed by diafiltration using 50 mM phosphate buffered saline.

4. Hemoglobin-Polyethylene Glycol Conjugate

In this experiment, the methods of Xue and Wong are used (Xue and Wong, Meth. Enz., 231: 308–323 [1994]) to produce hemoglobin-polyethylene glycol conjugates.

First, activation of PEG: Bis(succinimidyl succinate) is performed. PEG (200 g; 0.059 mol, average 3400 MW; Nippon Oil and Fats Co. Ltd., Tokyo, Japan) is dissolved in 200 ml of dimethylformamide at 100° C., and 15 g of succinic anhydride (0.15 mol) is added. The mixture is stirred for 3 hours at 100° C. The dimethylformamide solution is cooled to room temperature and poured into 1 liter of ethyl ether. The resulting PEG ester of succinic acid is filtered through a glass filter and washed with ethyl ether. The ester is then dried under vacuum conditions at 40° C. The weight of the product is about 197 g (93% yield).

To activate the succinyl groups on PEG, 197 g of the PEG ester of succinic acid (0.055 mol) is dissolved in 200 ml of dimethylformamide, after which 13 g of N-hydroxysuccinimide (0.11 mol) and 23 g of dicyclohexylcarbodiimide (0.22 mol) are added. The solution is stirred vigorously overnight at 30° C. The precipitate of dicyclohexylurea is filtered out and the filtrate is poured into 1 liter of ethyl ether. The polyethylene glycol bis(succinimidyl succinate) formed is isolated, washed with ethyl ether repeatedly, and dried under vacuum conditions at 40° C. The weight of the product is about 196 g, representing a yield from PEG of 87%.

The purity and the degree of imidylation of polyethylene glycol bis(succinimidyl succinate) may be estimated by nuclear magnetic resonance using tetramethylsilane as standard (0 ppm) and chloroform-$d_1$ as solvent. Similar procedures may be used for the electrophilic activation of monomethoxypolyethylene glycol.

Next, the activated PEG is conjugated to hemoglobin, with the following procedure being carried out at 4° C. First, 0.95 g (0.25 mmol) of polyethylene glycol bis(succinimidyl succinate) is added to 100 ml of a 0.25 mM Hb solution in 0.1 M sodium phosphate, pH 7.4 and the reaction continued for 1 hour. The solution is concentrated by ultrafiltration on an Amicon XM100 membrane. An electrolyte solution is then added and the concentration process repeated. By repeating this concentration procedure three times, unreacted PEG and other low molecular weight compounds are removed.

Then, the PEG-Hb is stabilized by taking advantage of the ester bond between PEG and succinic acid in PEG-Hb, which is labile to hydrolysis. One approach to increase the stability of the bond between PEG and Hb is to remove the labile ester linkage between the polyethylene moiety and the terminal carboxyls by oxidizing both terminal alcoholic groups of PEG to carboxylic groups through the use of a metal catalyst, to yield-carboxymethyl-ω-carboxymethoxylpolyoxyethylene, which is activated and coupled to pyridoxalated Hb as in the case of PEG. The resultant conjugate is designated "stabilized hemoglobin."

In addition, monomethoxypolyoxyethlylene-hemoglobin is produced. PEG has two hydroxyl groups at the two termini. When these are derivatized into functional groups capable of reacting with Hb, the presence of two reactive groups on the same polymer makes possible crosslinking reactions. Such cross-linking is abolished by blocking one of the two termini, as in the case of monomethoxypolyoxyethylene (MPOE).

To produce MPOE, 80 g (4 mmol) of MW 5000 MPOE from Aldrich (Milwaukee, Wis.) is dissolved in tetrahydrofuran (300 ml) and treated with naphthalene sodium under nitrogen at room temperature for 3 hours. Then BrCH$_2$COOC$_2$H$_5$ (1.4 ml; 12 mmol) is added dropwise with stirring. After 4 hours of reaction, the ethyl ester obtained is precipitated with ether, dried, dissolved in water, and saponified with 0.1 N NaOH at 55° C. for 24 hours to yield MPOE-carboxylic acid (MPOE-O—CH$_2$COOH). The solution is then acidified with 1 N HCl down to pH 2.5, and the polymer taken up with chloroform. After several washings with water, the organic layer is dried over MgSO$_4$ and treated with charcoal. The MPOE-carboxylic acid is precipitated with dry ether, filtered, and dried under vacuum. This run of operations is repeated until the potentiometric titration gives a constant value for the quantity of fixed COOH.

The MPOE-carboxylic acid (5 g; 1 mmol) is dissolved in dry ethyl acetate (60 ml) and activated by N-hydroxysuccinimide (0.15 g; 1.25 mmol) and dicyclohexylcarbodiimide (0.26 g; 1.25 mmol) at 30° C. for 15 hours. Dicyclohexylurea is removed by filtration and the polymer precipitated with dry ether is taken up with chloroform and crystallized from this solution by dropwise addition of ether at 0° C. This procedure is repeated several times until the spectrophotometric analysis of succinimidyl groups gave a constant value.

Coupling to hemoglobin is performed at 5° C. by diluting 1.5 ml of a 10 g/dl hemoglobin solution with 2 ml 0.1 M phosphate buffer, pH 5.8, and 300 mg of MPOE-carboxylic succinimidyl ester is added under stirring. The reaction mixture is stirred at 6° C. for 2 hours and analyzed by gel permeation chromatography on Ultrogel AcA 34 (linear fractionation range MW 20,000–350,000; exclusion limit 750 000) in 0.05 M phosphate buffer(pH 7.2) at 6° C.

5. Hemoglobin-Dextran Conjugate

In this experiment, hemoglobin-dextran conjugates are produced according to the various methods of Kue and Wong (Xue and Wong, Meth. Enz., 231: 308–323 [1994]).

Synthesis by Alkylation

In this method, the dextran (Dx) is first derivatized with cyanogen bromide and diaminoethane to contain a free amino group, which is acylated with bromoacetyl bromide. The bromoacetyl function in turn alkylates the sulfhydryl of the β93 cysteine on Hb:

Dx+CNBR+diaminoethane→aminoethyl-Dx

Aminoethyl-Dx+bromoacetyl bromide→Dx-NHCOCH$_2$Br

Dx-NHCOCH$_2$Br+HS-Hb→Dx-NHCOCH$_2$—S-Hb

In a typical preparation, 1.5 g of cyanogen bromide is dissolved in 15 ml of acetonitrile and added to 10 g of dextran (MW 20,000) in 375 ml of water. The pH is maintained at 10.8 for 5 min by the addition of 1 M NaOH; the pH is then lowered to about 2.0–2.5 with concentrated HCl. After stirring for 1 min, 15 ml of diaminoethane is added along with sufficient HCl to prevent the pH from exceeding 9.5. The final pH is adjusted to 9.5. After standing overnight at 4° C., the mixture is thoroughly dialyzed against distilled water using a Millipore (Marlborough, Mass.) Pellicon dialyzer and lyophilized. The aminoethyl-Dx so obtained is dissolved in 250 ml of 0.1 M sodium phosphate, pH 7.0, and 15 ml of bromoacetyl bromide is added through a Pasteur pipette with a finely drawn capillary tip, accompanied by vigorous stirring over a period of 2 hours. Throughout, the pH is maintained at 7.0 with the use of a pH-stat and addition of 1 M NaOH. Afterward, the mixture is dialyzed thoroughly against distilled water and is lyophilized to yield about 7 g of the Dx-NHCOCH$_2$Br (Br-dextran). The bromine content of the Br-dextran is in the range of 9–11 glucose residues per bromine atom.

To couple hemoglobin to dextran, 3.3 g of Br-dextran is dissolved in 100 ml of 6 g/dl hemoglobin solution in 0.1 M sodium bicarbonate, pH 9.5. The coupling reaction is allowed to proceed with constant mixing at 4° C. To determine the yield of Dx-NHCOCH$_2$—S-Hb (Dx-Hb), 0.1 ml of the reaction mixture is applied to a Sephadex G-75 column equilibrated with 0.05 M phosphate buffer, pH 7.5, and eluted with the same buffer, at a flow rate of 40 ml/hr. The hemoglobin content of the eluant fractions is determined by absorbance at 415 nm, and the proportions of the faster migrating Dx-Hb peak and the slower migrating Hb peak were given by the areas under these peaks. After 2 days the formation of the Dx-Hb conjugate is essentially complete.

Synthesis by Dialdehyde

Ten ml of a 12% aqueous solution of sodium periodate is added to 100 ml of a 0.10% aqueous solution of dextran, and the mixture is left overnight in the dark at 4° C. A 3% solution of sodium bisulfite is added until the mixture turned brown and then, once again, colorless. The mixture is dialyzed against distilled water to yield the dextran dialdehyde solution. It is then added to 2 volumes of 3 g/dl stroma-free hemoglobin in 0.3 M sodium bicarbonate buffer, pH 9.5; coupling of hemoglobin to dextran is allowed to proceed overnight at 4° C. The Dx-Hb complex formed is separated from uncoupled hemoglobin by means of chromatography on a Sephadex G-75 column.

Coupling of Hb to Dx-dialdehyde is pH dependent. When coupling is performed by dissolving 100 mg Dx-dialdehyde in 1 ml of 0.6 M sodium borate buffer and mixing with 1.8 ml of 10 g/dl Hb at 6° C., many labile imine linkages are formed at pH<9.6, and the conjugates have a high molecular weight, ranging to above 100,000. At higher pH, the major product has a lower molecular weight range (70,000>MW>100,000) and likely consists of a 1:1 complex between Dx and Hb, which only slowly converts to higher molecular weight forms. When this conjugate is formed at pH 9.8 and reduced at pH 7.2 for 30 min with excess NaBH$_4$ (2 mol per mole of initial aldehyde) dissolved in 1 mM NaOH, only the α chain of hemoglobin is found to be modified by Dx. Coupling of Hb to Dx-dialdehyde also proceeds much more rapidly at higher pH, requiring less than 1 hour for completion at pH 10 and only 1.5 hours at pH 9.7, but 6 hours at pH 9.5 and 23 hours at pH 9.1. When prepared at pH 9.75, the oxygen P50 for Dx-Hb is 10.1 mm Hg when the conjugate is allowed to form for 1 hour prior to NaBH$_4$ reduction, 9.5 mm Hg when allowed to form for 4 hours, and 8.1 when allowed to form for 18 hours.

6. Hemoglobin Conjugation to SF-DX and P-Dx

In this experiment, hemoglobin is conjugated with SF-DX and P-Dx. Dextran-sulfate (SF-Dx) and dextran-phosphate (P-Dx) (MW 40,000) are treated with sodium periodate to generate the dialdehydyl derivatives, which are in turn coupled to the amino groups on hemoglobin and are further stabilized by reduction with sodium borohydride, as described above in the synthesis of Dx-Hb from Dx-dialdehyde.

7. Hemoglobin Conjugation to Dextran-Benzene Hexacarboxylate (Dx-BHC)

In this experiment, hemoglobin is conjugated with dextran-benzene hexacarboxylate (Dx-BHC). Aminopropyl-Dx is prepared 35 by dissolving 5 g of dextran in 7.5 ml of 25% aqueous $Zn(BF_4)_2$ and 5 ml of water. Epichlorohydrin (25 ml) is added with vigorous stirring; the mixture is allowed to react for 3 hours at 80° C. and subsequently overnight at room temperature. The polymer is precipitated by pouring the solution dropwise into acetone, filtered, and dried under reduced pressure. The resulting dextran derivative has the structure of Dx-O—$CH_2CH(OH)CH_2Cl$. This product (4.1 g containing 3% Cl) is purified by repeated dissolution in water and precipitation by acetone and methanol. The chlorine atom is subsequently replaced by an amino group by dissolving the compound in 60 ml of $H_2O$ and 20 ml of 14 M aqueous ammonia. The solution is stirred for 20 hours at room temperature and then poured dropwise into 1 liter of methanol. The resulting precipitate of aminopropyl-Dx (3-amino-2-hydroxypropyl ether of dextran) is filtered, washed with acetone, and dried under reduced pressure. The yield at this stage is about 3.5 g.

Benzene hexacarboxylic acid is coupled to aminopropyl-Dx to form Dx-BHC through the use of 1-(3-dimethylaminopropyl)-3-ethylcarbodiimide hydrochloride (EDCl) as condensing agent. Because benzene hexacarboxylic acid has six carboxylic acid groups, reaction with an amino group on aminopropyl-Dx still leaves it with up to five carboxylic acid groups. One of these may be linked to an amino group on Hb through further use of the water-soluble EDCl as condensing agent.

8. Hydroxyethyl Starch-Hemoglobin-Conjugate

In this experiment, the method of Xue and Wong, (Xue and Wong, Meth. Enz., 231: 308–323 [1994]) is used to produce hydroxyethyl starch-hemoglobin conjugates.

To prepare for conjugation to hemoglobin, the hydroxyethyl starch (Hs) is first converted to aminoethyl-Hs. In a typical preparation, 1.5 g of cyanogen bromide is dissolved in 15 ml of acetonitrile and added to 500 ml of 2% Hs solution. The pH of the solution is maintained at 10.8 for 5–10 min by the addition of 1 M NaOH solution. The pH is then lowered to 2.0–2.5 with concentrated HCl, and 10 ml of diaminoethane is added along with additional HCl to prevent the pH from exceeding 9.5. The final pH is adjusted to 9.5 and the solution is allowed to stand overnight at 4° C. before being dialyzed against deionized water. The ratio of cyanogen bromide/diaminoethane to Hs can be varied, allowing the synthesis of aminoethyl-Hs in which from 7 to 20% of the glucose residues in the starting polymer are substituted.

Aldehyde-substituted Hs is prepared by reaction of the aminoethyl-Hs with glutaraldehyde. In a typical reaction, 500 ml of dialyzed solution of aminoethyl-Hs is treated with 2 g of sodium bicarbonate to give a solution 2% in Hs and approximately 0.05 M in bicarbonate. Then 5 ml of 50% glutaraldehyde solution is added to the solution, which is stirred at room temperature for 2 hours before dialysis.

Hemoglobin is employed as a freeze-dried solid under carbon monoxide. This is reconstituted under argon using deoxygenated deionized water at 4° C. to give a solution with approximately 2.5 g Hb per ml. In a typical reaction, 500 ml of dialyzed solution of the aldehyde-substituted Hs is treated with sodium bicarbonate to give 500 ml of solution approximately 2% in Hs and 0.1 M in bicarbonate, hemoglobin solution (25 ml) is added and the reaction is stirred at room temperature for 4 hours, after which time gel filtration on Sephadex G-150 indicates that no unmodified hemoglobin remains. Sodium borohydride (1.0 g) is then added to the solution, which is stirred for a further 2 hours at room temperature. The Hs-Hb is dialyzed using an Amicon (Danvers, Mass.) ultrafiltration unit with a 100,000 molecular weight cutoff cartridge to enable the removal of any trace of unmodified hemoglobin. Glucose (10 g) is added to the solution prior to freeze-drying and storage under carbon monoxide at 4° C.

9. An Alternative Method for Producing Hydroxyethyl Starch-Hemoglobin Conjugates In this experiment, another method described by Xue and Wong (Xue and Wong, Meth. Enz., 231: 308–323 [1994]) was used to produce hydroxyethyl starch-hemoglobin conjugates.

Hydroxyethyl starch-hemoglobin-conjugate (Hs-Hb) can be synthesized from Hs-dialdehyde as follows. 0.03 equivalents of Hs are dissolved in 250 ml of water and treated with 0.028 mol of sodium periodate for 12 hours at 5° C. in the dark. The solution is dialyzed until ion free. The percent oxidation may be determined using a calorimetric method. The solution is buffered to pH 8.0 by addition of sodium bicarbonate, cooled to 5° C., and treated with 5 g of carbonmonoxyhemoglobin. The reaction is allowed to proceed for 18 hours at room temperature or until gel filtration indicates complete modification of hemoglobin. The solution is dialyzed against 1% ammonium carbonate and freeze-dried in the presence of glucose.

10. Hemoglobin-Inulin Conjugate

In this experiment, a method described by Xue and Wong (Xue and Wong, Meth. Enz., 231: 308–323 [1994]) is used to produce hemoglobin-inulin conjugates.

To synthesize the inulin-hemoglobin (In-Hb) conjugate, inulin is first succinylated by reacting with succinic anhydride in N,N-dimethylformamide at 100° C. for 2 hours. Subsequently, the succinylated inulin is linked to N-hydroxysuccinimide at room temperature overnight using dicyclohexylcarbodiimide as condensation agent in N,N-dimethylformamide. Hemoglobin is allowed to react with a 10-fold molar excess of the N-hydroxysuccinimide-activated inulin in 0.1 M Tris buffer, pH 7.0, at 4° C. for 1 hour to yield In-Hb, which is purified with an Amicon PM30 membrane filter until the unreacted inulin and other low molecular weight compounds are removed.

By controlling the succinic anhydride/inulin ratio, the number of N-hydroxysuccinimide-activated succinyl groups on the inulin can be varied. A low density of such groups gives rise to a 82,000 MW In-Hb conjugate, whereas higher densities produce cross-linked In-Hb ranging up to above 300,000 MW.

11. An Alternative Method to Produce Hemoglobin-Inulin Conjugates

In this experiment, the method of Iwasaki et al. (Iwasaki et al., Biochem. Biophys. Res. Comm., 113: 513–518 [1983]) is used to produce hemoglobin-inulin conjugates.

The N-hydroxysuccinimidyl ester of inulin was reacted with oxyhemoglobin in 0.1 M tris buffer (pH 7.0) at 4° C. for one hour. The reaction mixture was analyzed with a JASCO Trirotor HPLC apparatus equipped with a TSK G3000 SW column. The modified hemoglobin solution was purified with an Amicon PM 30 membrane filter until the unreacted inulin and other low molecular weight compounds are no longer detected.

12. Hemoglobin-Polyvinylpyrrolidone Conjugate

In this experiment, the method of Xue and Wong (Xue and Wong, Meth. Enz, 231: 308–323 [1994]) was used to produce hemoglobin-polyvinylpyrrolidone conjugates.

Synthesis of Activated PVP

First, 50 g of polyvinylpyrrolidone (PVP) (MW 25,000–35,000) is dissolved in 1 liter of 0.25 N NaOH and heated at 140° C. for 42 hours under nitrogen in an autoclave to bring about partial hydrolysis. It is then adjusted to pH 5 with concentrated HCl and ultrafiltered through an Amicon UM10 membrane to remove salts. Water is removed through azeotropic distillation with benzene, and the extent of hydrolysis is determined by titration of the secondary amino groups. To blockade these amino groups, 50 g of the partially hydrolyzed PVP is dissolved in 300 ml of dichloromethane/dimethylformamide (1:1) and mixed with 0.5 M of acetic acid anhydride. It is left at room temperature for 1 hour and refluxed for 4 hours. Evacuated to about 100 ml, the solution is added dropwise into ethyl ether under strong stirring. The acetylated PVP precipitate is filtered, washed with ether, and dried to constant weight under vacuum over phosphorus pentoxide.

To activate its carboxyl groups, 50 g of acetylated PVP dissolved in 500 ml of dichloromethane/dimethylformamide (1:1) is mixed at 0° C. with 15.47 g of N-hydroxysuccinimide followed with a solution of 27.75 g dicyclohexylcarbodiimide in 50 ml of dichloromethane. The solution is stirred at 0° C. for 14 hours before centrifugation to remove the dicyclohexylurea. The supernatant solution (about 300 ml) is added dropwise into 5 liters of cold ether under strong stirring. The white precipitate is filtered, washed repeatedly with ether, and dried in the cold over phosphorus pentoxide.

Binding of Hemoglobin to Activated PVP

Hemoglobin (27 g) is dissolved in 1 liter of 5% sodium carbonate and treated at 4° C. with 40 g of activated PVP for 24 hours with stirring. The preparation is lyophilized and redissolved in 300 ml of distilled water. After a 20-fold volume diafiltration, it is again lyophilized.

From the above, it should be evident that the present invention provides optimal blood substitute compositions comprising mixtures of oxygen-carrying and non-oxygen carrying plasma expanders and methods for the use thereof. These compositions and methods allow for the production of relatively inexpensive products that are more effective than currently available compositions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in hematology, surgical science, transfusion medicine, transplantation, or any related fields are intended to be within the scope of the following claims.

I claim:

1. A method of treating a human patient with an oxygen carrier, comprising the step of administering an aqueous cell-free composition, wherein said composition comprises a polyalkylene oxide surface modified hemoglobin without intramolecular crosslinking, wherein said polyalkylene oxide surface modified hemoglobin has an oxygen affinity greater than or equal to whole blood, and wherein said composition has an oxygen capacity less than whole blood, a viscosity at least half that of blood, and an oncotic pressure higher than that of plasma.

2. The method of claim 1, wherein the patient is suffering from a condition selected from the group consisting of septic shock, ischemia, chronic anemia, sickle cell anemia, stroke, disseminated intravascular coagulation, hypovolemic shock and hypoxia.

3. The method of claim 1, wherein the patient is suffering from septic shock.

4. The method of claim 1, wherein the patient is suffering from a stroke.

5. The method of claim 1, wherein the patient is suffering from chronic anemia.

6. The method of claim 1, wherein the patient is suffering from sickle cell anemia.

7. The method of claim 1, wherein the patient is suffering from disseminated intravascular coagulation.

8. The method of claim 1, wherein the patient is suffering from hypovolemic shock.

9. The method of claim 1, wherein the patient is suffering from ischemia of the heart or brain.

10. The method of claim 9, wherein the ischemia is caused by a heart attack or cerebrovascular event.

11. The method of claim 1, wherein the patient is suffering from hypoxia.

12. The method of claim 11, wherein the hypoxia is caused by exposure to high altitudes.

13. A method of performing hemodilution on a human patient comprising the steps of removing a volume of blood and replacing the volume with an aqueous cell-free composition, wherein said composition comprises a polyalkylene oxide surface modified hemoglobin without intramolecular crosslinking, wherein said polyalkylene oxide surface modified hemoglobin has an oxygen affinity greater than or equal to whole blood, and wherein said composition has an oxygen capacity less than whole blood, a viscosity at least half that of blood, and an oncotic pressure higher than that of plasma.

* * * * *